(12) United States Patent
Sherts et al.

(10) Patent No.: US 6,213,940 B1
(45) Date of Patent: Apr. 10, 2001

(54) SURGICAL RETRACTOR INCLUDING COIL SPRING SUTURE MOUNT

(75) Inventors: Charles R. Sherts, Westport; David A. Nicholas, Trumbull; David Farascioni, Bethel; Keith Ratcliff, Newtown; Peter W. J. Hinchliffe, New Haven; Cathy Aranvi, Easton, all of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/388,716

(22) Filed: Sep. 2, 1999

Related U.S. Application Data

(62) Division of application No. 08/801,052, filed on Feb. 14, 1997, now Pat. No. 5,967,973, which is a continuation of application No. 08/717,591, filed on Sep. 23, 1996, now abandoned.
(60) Provisional application No. 60/016,325, filed on Apr. 26, 1996.

(51) Int. Cl.[7] ............................................... A61B 1/32
(52) U.S. Cl. .................................... 600/231; 600/233
(58) Field of Search .................................. 600/233, 232, 600/227, 231; 606/233, 232

(56) References Cited

U.S. PATENT DOCUMENTS

| Re. 34,150 | 12/1992 | Santilli et al. . |
|---|---|---|
| 497,064 | 5/1893 | Vanmeter . |
| 1,157,202 | 10/1915 | Bates . |
| 1,400,616 | 12/1921 | McCrory . |
| 1,706,500 | 3/1929 | Smith . |
| 1,707,689 | 4/1929 | Sloan . |
| 1,839,726 | 1/1932 | Arnold . |
| 1,919,120 | 7/1933 | O'Connor et al. . |
| 1,963,173 | 6/1934 | Morin . |
| 2,053,868 | 9/1936 | Grosso . |
| 2,384,304 | 9/1945 | Helfrick . |
| 2,473,266 | 6/1949 | Wexler . |
| 2,594,086 | 4/1952 | Smith . |

(List continued on next page.)

FOREIGN PATENT DOCUMENTS

| 0246086 | 11/1987 | (EP) . |
|---|---|---|
| 0 336 526 | 10/1989 | (EP) . |
| 1005345 | 12/1951 | (FR) . |
| 2102681 | 2/1983 | (GB) . |
| 116547 | 6/1918 | (IN) . |
| WO 8904145 | 5/1989 | (WO) . |
| WO9221296 | 10/1992 | (WO) . |

*Primary Examiner*—Jeffrey A. Smith

(57) ABSTRACT

Apparatus and method for surgery is disclosed which includes a retractor having a substantially planar base defining an opening for overlying an operative site on a patient, and at least one retractor blade slidably mounted to the base. The base is positioned on the patient such that the opening therein overlies the operative site. The operative site is percutaneously accessed, and obstructing tissue is retracted by engaging the tissue with the retractable blade. A surgical instrument is provided which in engageable with the base and operable at the operative site through the opening in the base. A surgical procedure is carried out through the opening in the base with the surgical instrument.

3 Claims, 46 Drawing Sheets

U.S. PATENT DOCUMENTS

| | | |
|---|---|---|
| 2,623,517 | 12/1952 | Barlow et al. . |
| 2,701,562 | 2/1955 | Michael et al. . |
| 3,070,088 | 12/1962 | Brahos . |
| 3,129,706 | 4/1964 | Reynolds, Jr. . |
| 3,168,093 | 2/1965 | Gauthier . |
| 3,384,077 | 5/1968 | Gauthier . |
| 3,463,144 | 8/1969 | Hammond . |
| 3,509,873 | 5/1970 | Karlin et al. . |
| 3,522,799 | 8/1970 | Gauthier . |
| 3,680,546 | 8/1972 | Asrican . |
| 3,724,449 | 4/1973 | Gauthier . |
| 3,747,592 | 7/1973 | Santos . |
| 3,858,578 | 1/1975 | Milo . |
| 3,965,890 | 6/1976 | Gauthier . |
| 3,998,217 | 12/1976 | Trumbull et al. . |
| 4,010,741 | 3/1977 | Gauthier . |
| 4,048,987 | 9/1977 | Hurson . |
| 4,165,746 | 8/1979 | Burgin . |
| 4,190,042 | 2/1980 | Sinnreich . |
| 4,226,228 | 10/1980 | Shin et al. . |
| 4,254,763 | 3/1981 | McCready et al. . |
| 4,281,366 | 7/1981 | Wurster et al. . |
| 4,337,762 | 7/1982 | Gauthier . |
| 4,421,107 | 12/1983 | Estes et al. . |
| 4,421,108 | 12/1983 | Cabrera et al. . |
| 4,424,724 | 1/1984 | Bookwalter et al. . |
| 4,430,991 | 2/1984 | Darnell . |
| 4,457,300 | 7/1984 | Budde . |
| 4,467,791 | 8/1984 | Cabrera et al. . |
| 4,492,229 * | 1/1985 | Grunwald . |
| 4,562,832 | 1/1986 | Wilder et al. . |
| 4,597,030 | 6/1986 | Brody et al. . |
| 4,605,990 | 8/1986 | Wilder et al. . |
| 4,627,421 * | 12/1986 | Symbas et al. . |
| 4,726,356 | 2/1988 | Santilli et al. . |
| 4,744,363 | 5/1988 | Hasson . |
| 4,745,908 | 5/1988 | Wardle . |
| 4,747,395 | 5/1988 | Brief . |
| 4,765,311 | 8/1988 | Kulik et al. . |
| 4,782,819 | 11/1988 | Adair . |
| 4,796,846 | 1/1989 | Meier et al. . |
| 4,813,401 | 3/1989 | Grieshaber . |
| 4,829,985 | 5/1989 | Couetil . |
| 4,848,323 | 7/1989 | Marijnissen et al. . |
| 4,852,552 | 8/1989 | Chaux . |
| 4,856,518 | 8/1989 | McFadden . |
| 4,865,019 | 9/1989 | Phillips . |
| 4,867,404 | 9/1989 | Harrington et al. . |
| 4,870,952 | 10/1989 | Martinez . |
| 4,921,326 | 5/1990 | Wild et al. . |
| 4,932,395 | 6/1990 | Mehdizadeh . |
| 4,949,707 | 8/1990 | Levahn et al. . |
| 4,988,355 | 1/1991 | Leveen et al. . |
| 5,000,163 | 3/1991 | Ray et al. . |
| 5,003,434 | 3/1991 | Gonser et al. . |
| 5,025,779 | 6/1991 | Bugge . |
| 5,049,153 | 9/1991 | Nakao et al. . |
| 5,052,373 | 10/1991 | Michelson . |
| 5,052,374 | 10/1991 | Alvarez-Jacinto . |
| 5,067,477 | 11/1991 | Santangelo . |
| 5,088,472 | 2/1992 | Fakhrai . |
| 5,100,430 | 3/1992 | Avellanet et al. . |
| 5,133,727 | 7/1992 | Bales et al. . |
| 5,167,223 * | 12/1992 | Koros et al. . |
| 5,228,451 | 7/1993 | Bales et al. . |
| 5,231,974 | 8/1993 | Giglio et al. . |
| 5,238,002 | 8/1993 | Devlin et al. . |
| 5,254,130 | 10/1993 | Poncet et al. . |
| 5,284,130 | 2/1994 | Ratliff . |
| 5,299,563 | 4/1994 | Seton . |
| 5,306,234 | 4/1994 | Johnson . |
| 5,325,866 | 7/1994 | Kryzyzanowski . |
| 5,336,221 | 8/1994 | Anderson . |
| 5,337,735 | 8/1994 | Salerno . |
| 5,346,504 | 9/1994 | Ortiz et al. . |
| 5,351,168 | 9/1994 | Easley . |
| 5,354,311 | 10/1994 | Kambin et al. . |
| 5,375,481 | 12/1994 | Cabrera et al. . |
| 5,380,338 | 1/1995 | Christian . |
| 5,386,489 | 1/1995 | Stokes . |
| 5,400,774 | 3/1995 | Villalta et al. . |
| 5,411,481 | 5/1995 | Allen et al. . |
| 5,419,339 | 5/1995 | Palmer . |
| 5,447,149 | 9/1995 | Kikawada et al. . |
| 5,450,293 | 9/1995 | Hoffman . |
| 5,452,395 | 9/1995 | Schichman et al. . |
| 5,500,918 | 3/1996 | Pileski et al. . |
| 5,503,617 | 4/1996 | Jako . |
| 5,514,077 | 5/1996 | Rabban . |
| 5,520,610 | 5/1996 | Giglio et al. . |
| 5,520,611 | 5/1996 | Rao et al. . |
| 5,520,678 | 5/1996 | Heckele et al. . |
| 5,535,754 | 7/1996 | Doherty . |
| 5,571,136 | 11/1996 | Weaver . |
| 5,578,056 | 11/1996 | Pauldrach . |
| 5,580,147 | 12/1996 | Salerno . |
| 5,602,948 | 2/1997 | Currie . |
| 5,624,432 | 4/1997 | Angelchik . |
| 5,667,472 | 9/1997 | Finn et al. . |
| 5,667,473 | 9/1997 | Finn et al. . |
| 5,667,478 | 9/1997 | McFarlin et al. . |
| 5,755,660 | 5/1998 | Tyagi . |
| 5,823,956 | 10/1998 | Roth et al. . |
| 5,829,447 | 11/1998 | Stevens et al. . |
| 5,855,614 | 1/1999 | Stevens et al. . |
| 5,857,965 * | 1/1999 | Rootman et al. .................... 600/233 |
| 5,947,896 * | 9/1999 | Sherts et al. ......................... 600/229 |
| 5,967,973 * | 10/1999 | Sherts et al. ......................... 600/233 |
| 5,976,080 * | 11/1999 | Farascioni ........................ 600/231 X |

* cited by examiner

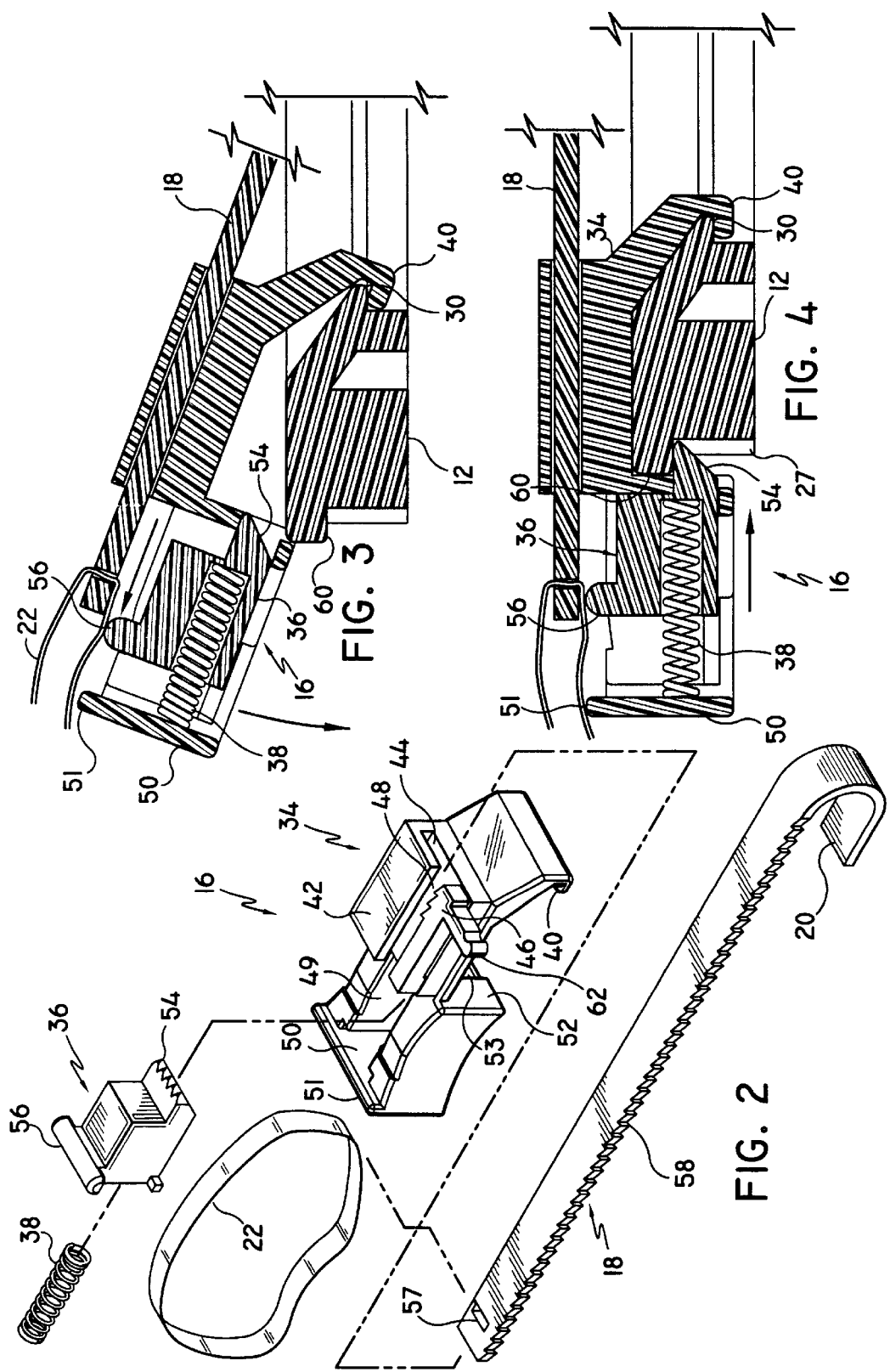

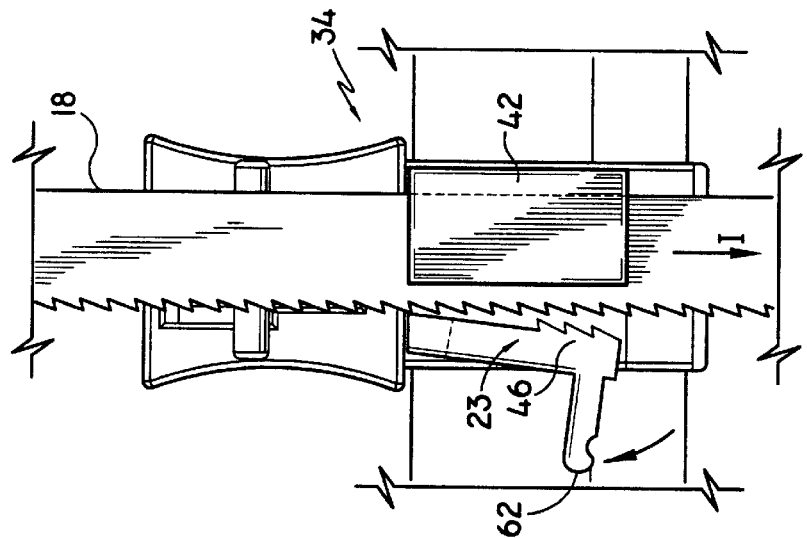
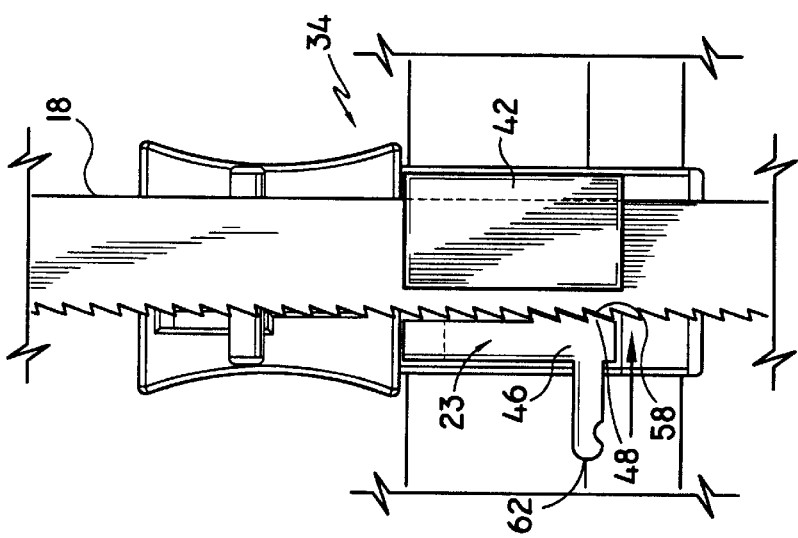
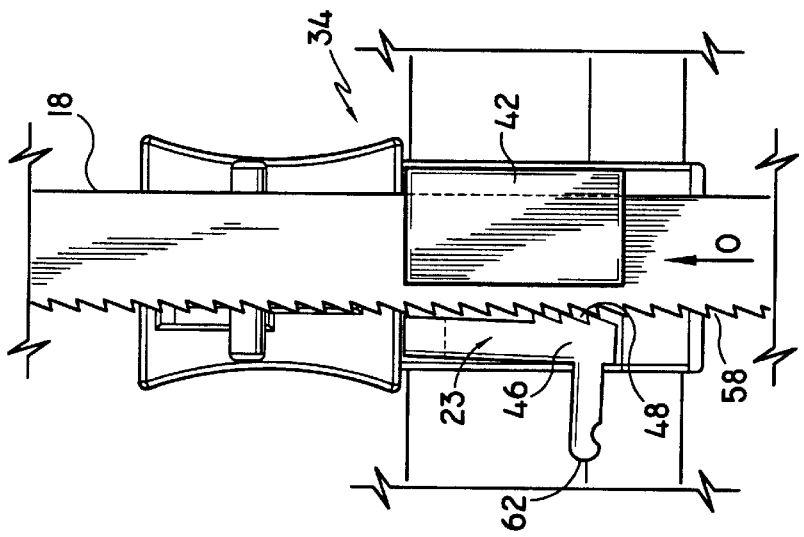

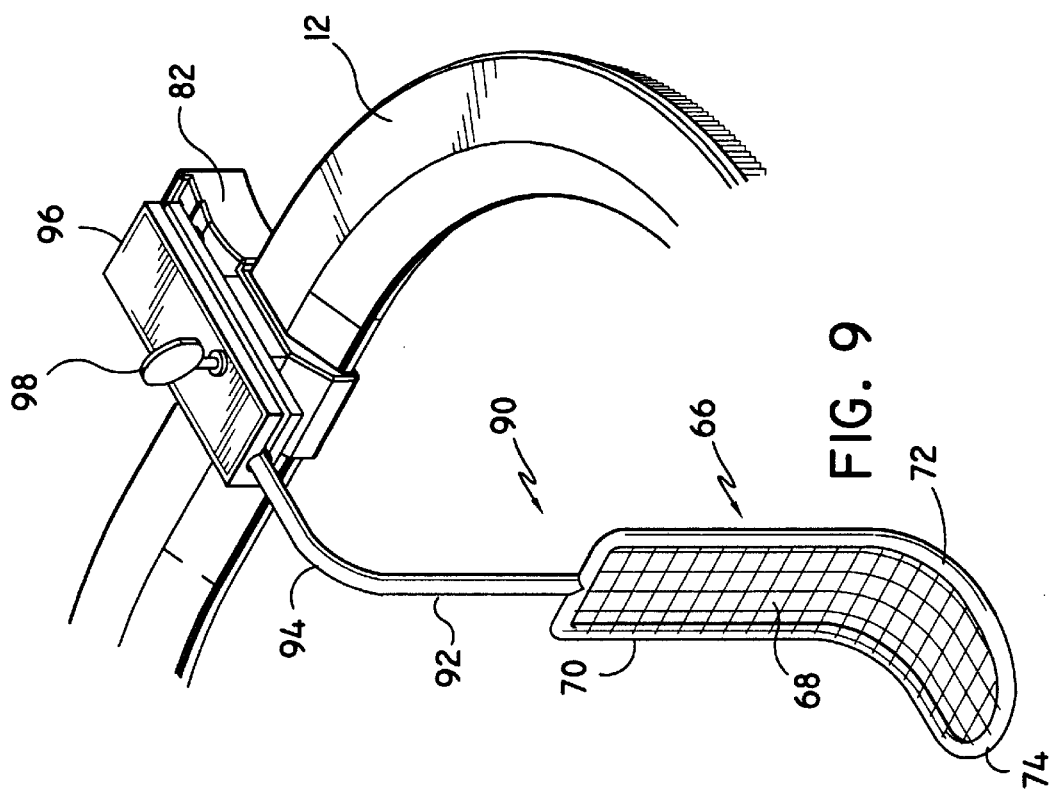
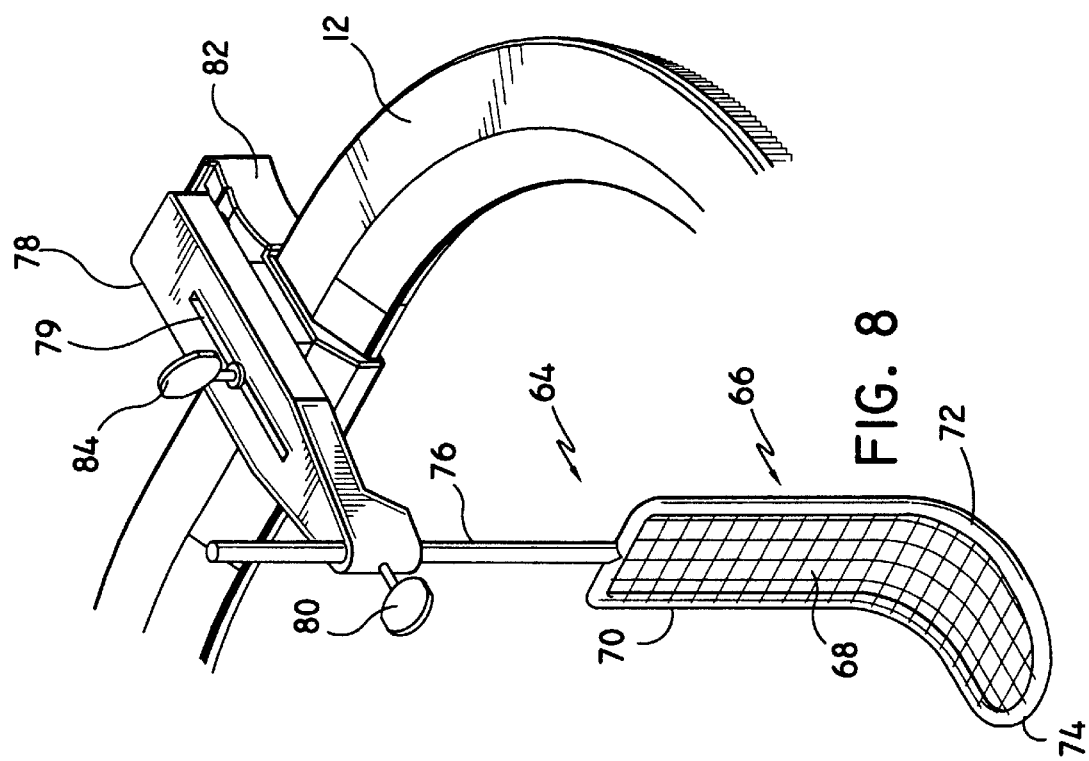

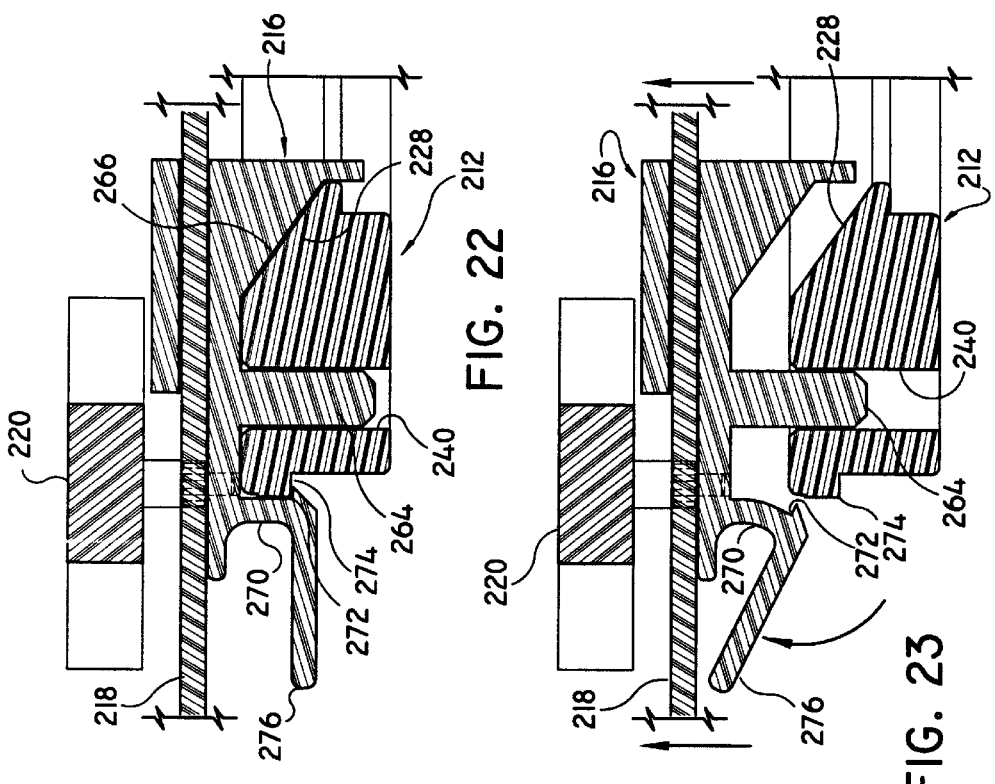
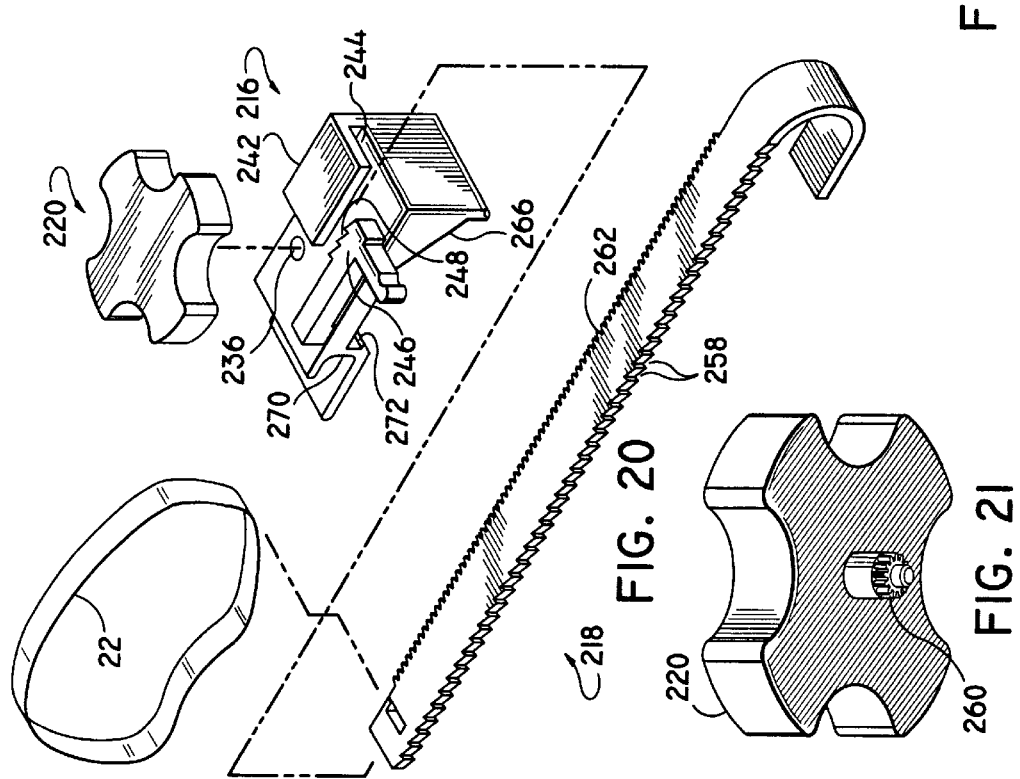

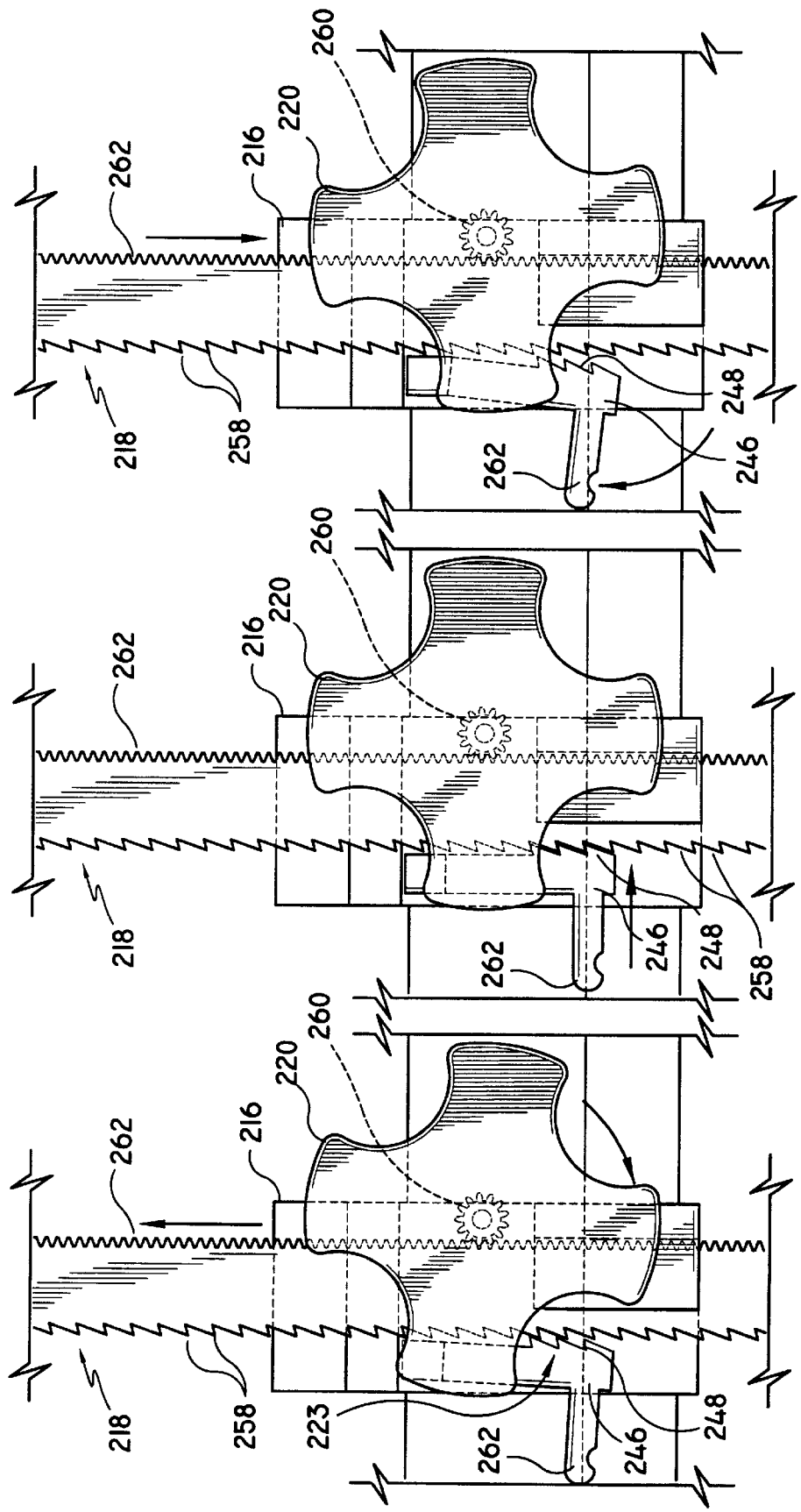

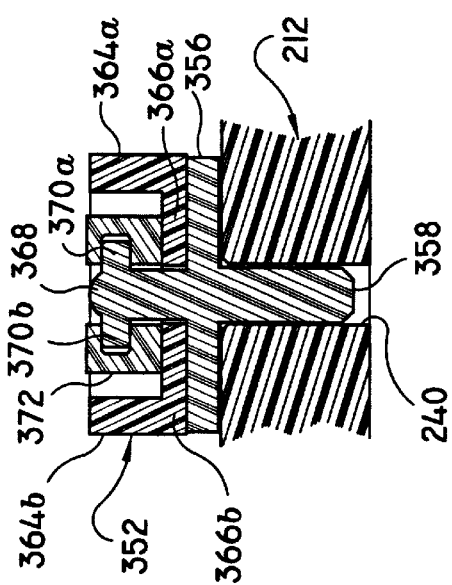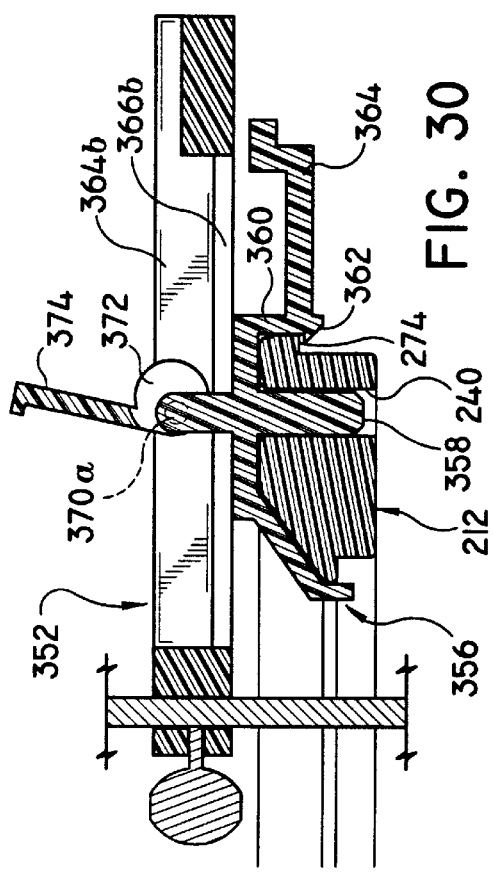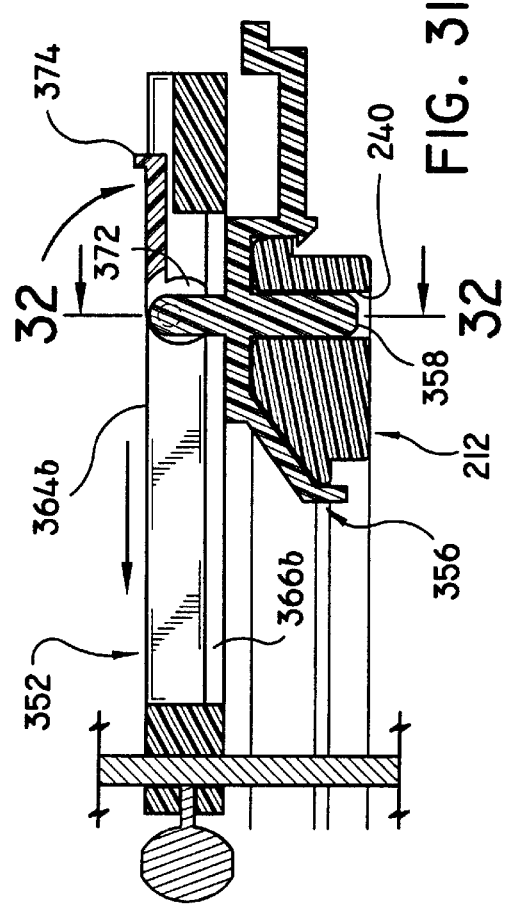

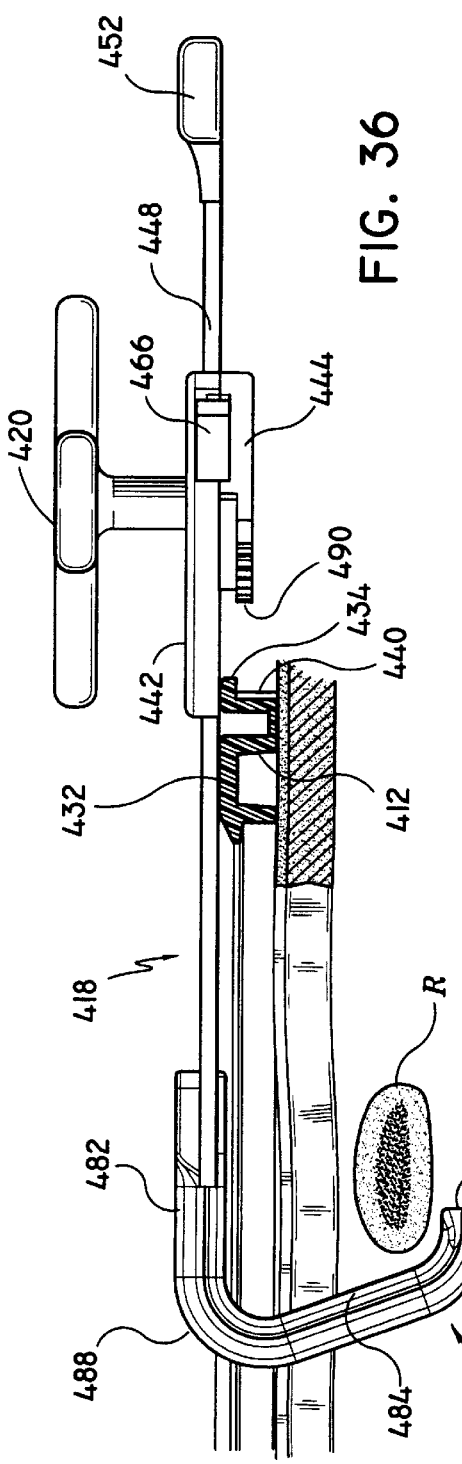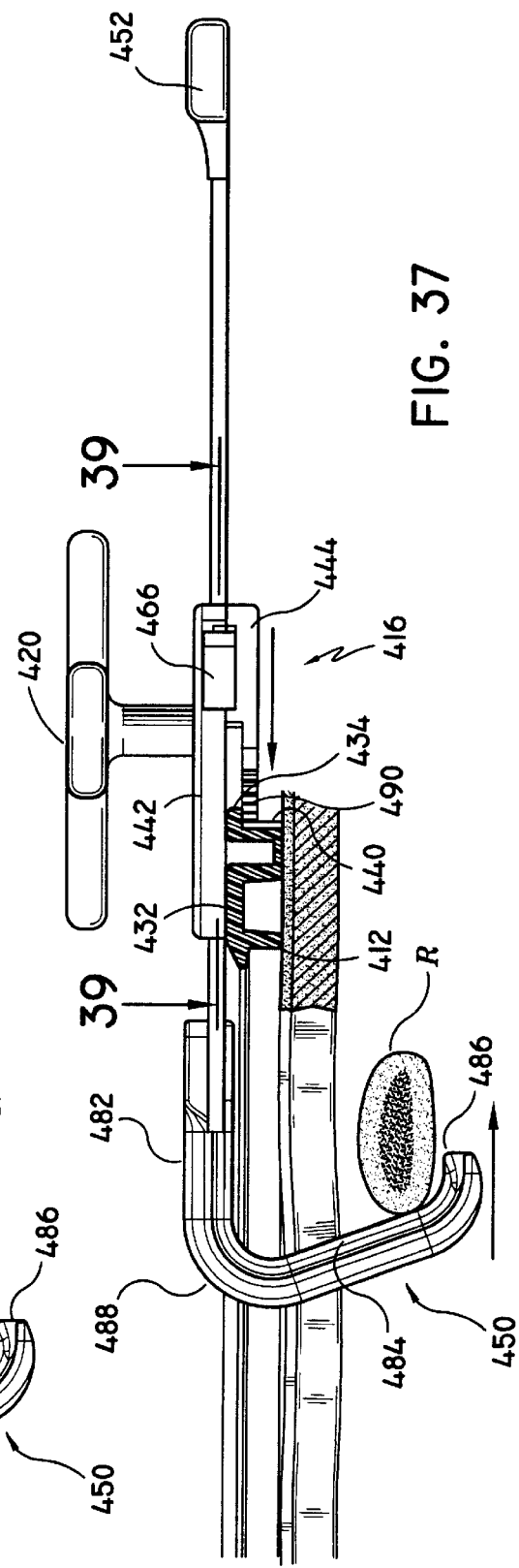

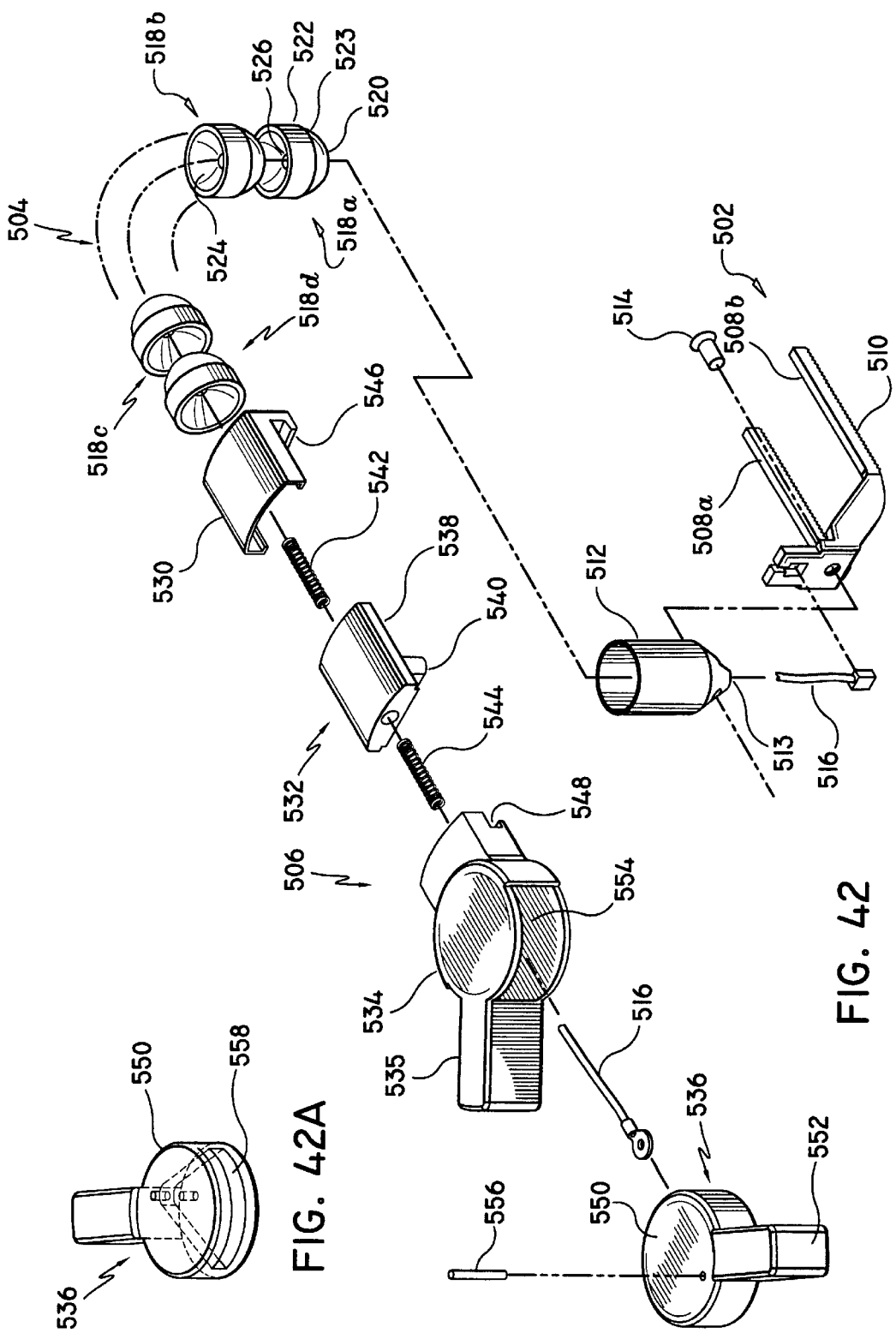

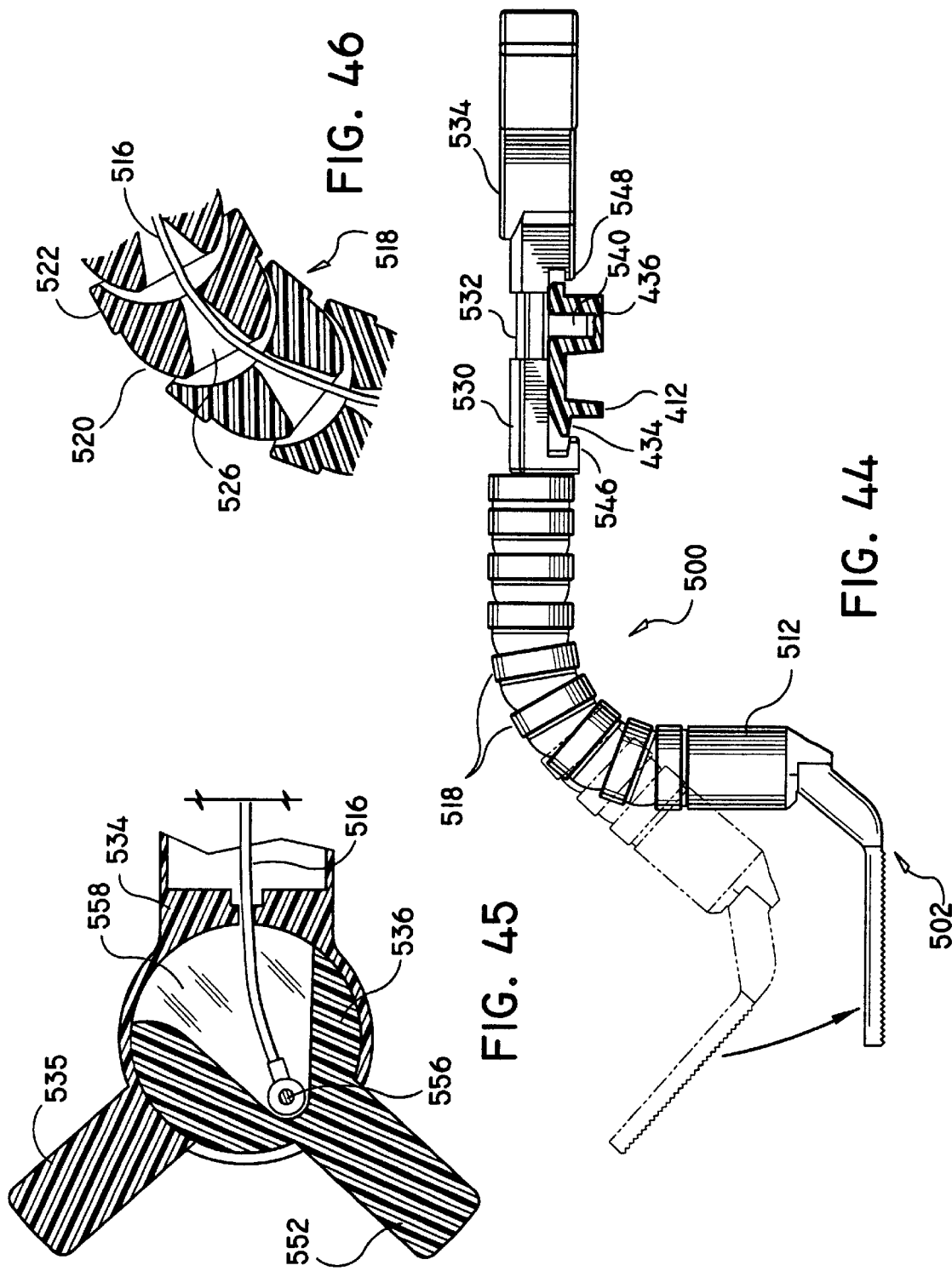

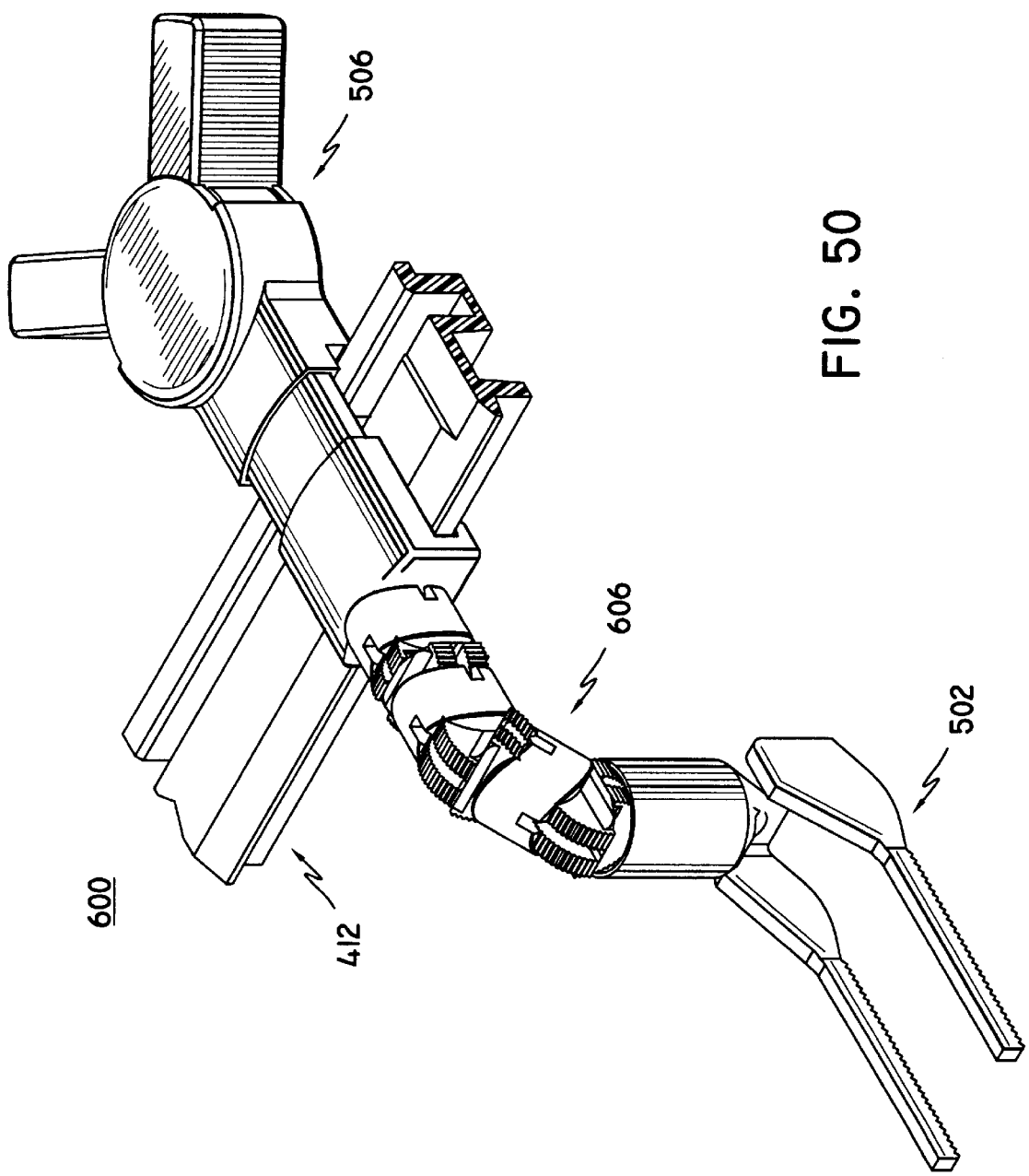

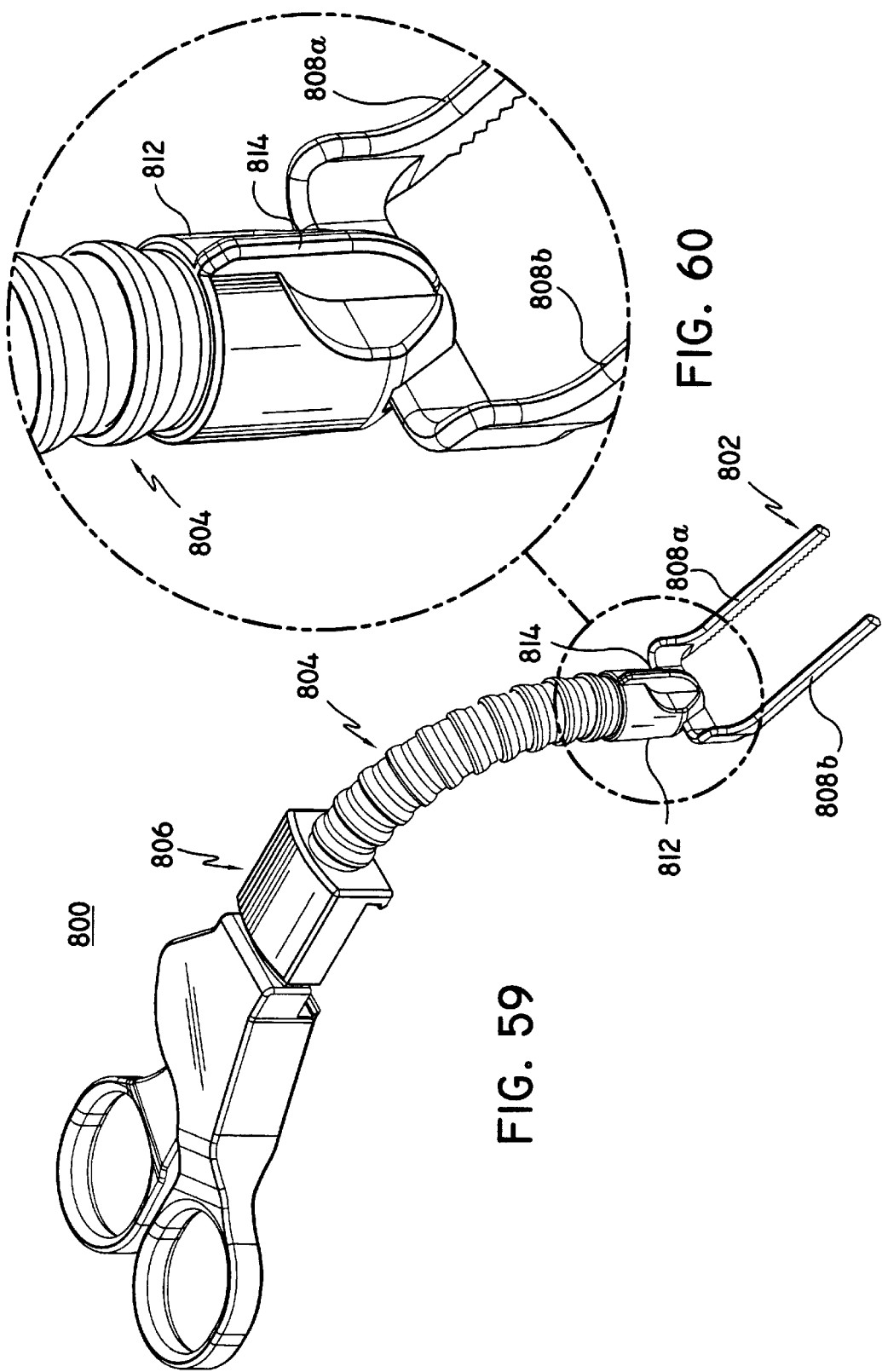

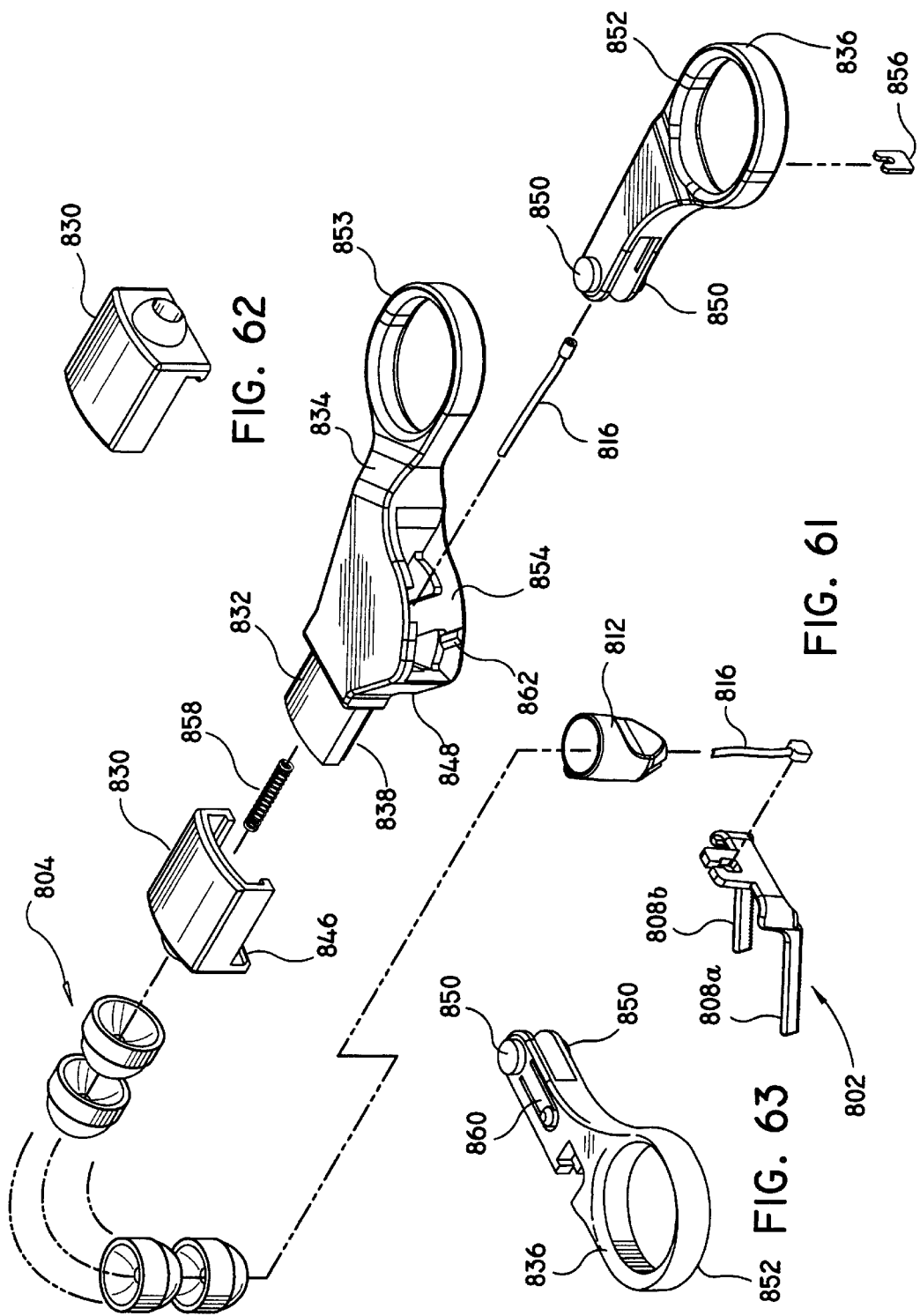

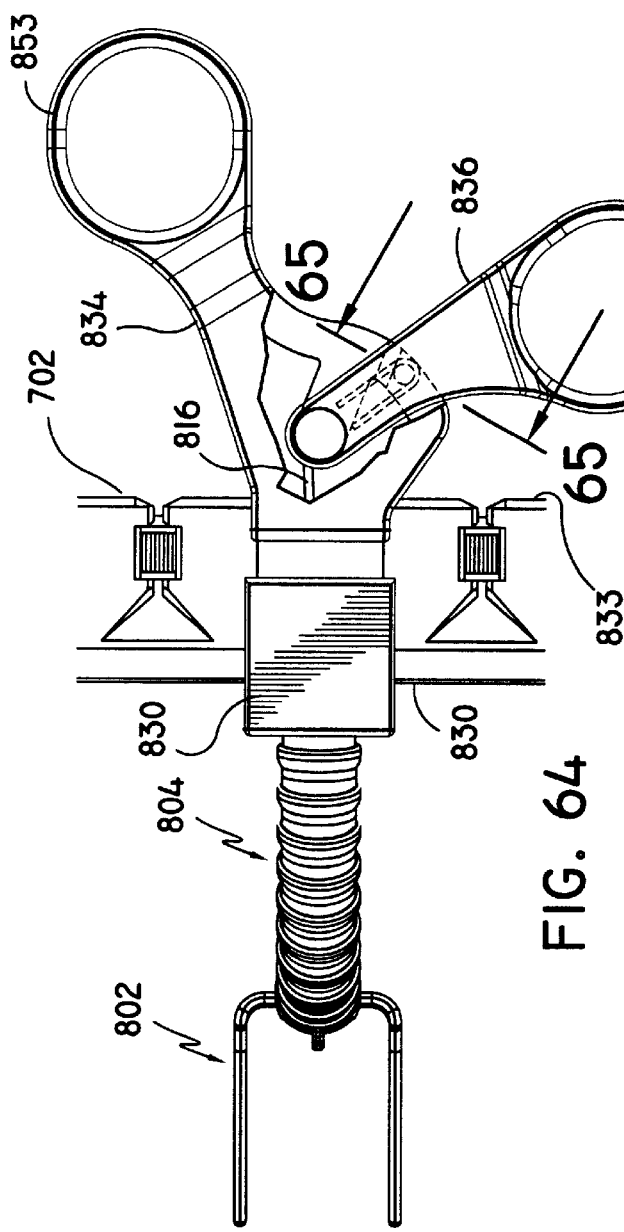
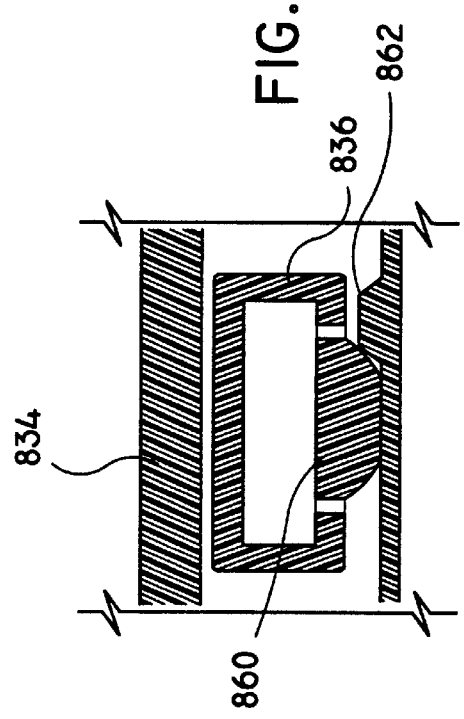
FIG. 64
FIG. 65

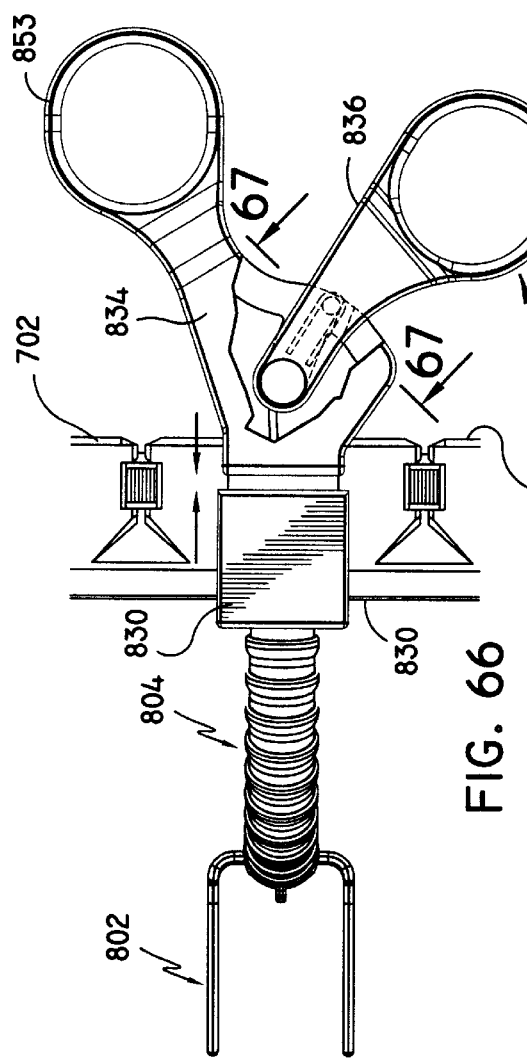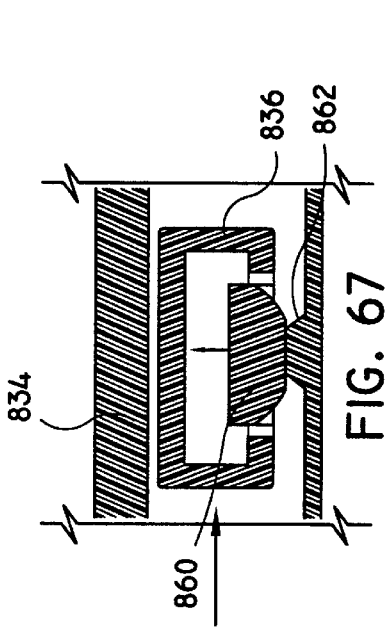
FIG. 66
FIG. 67

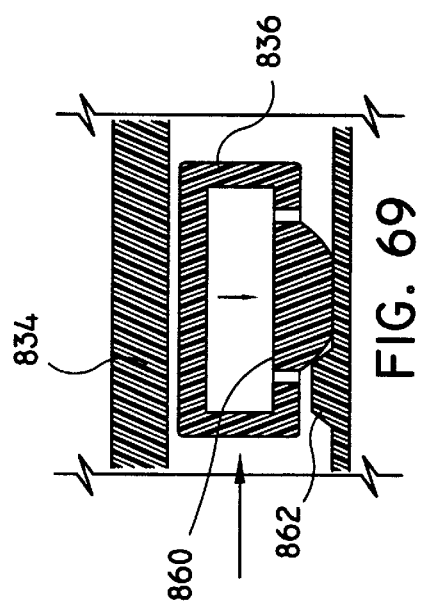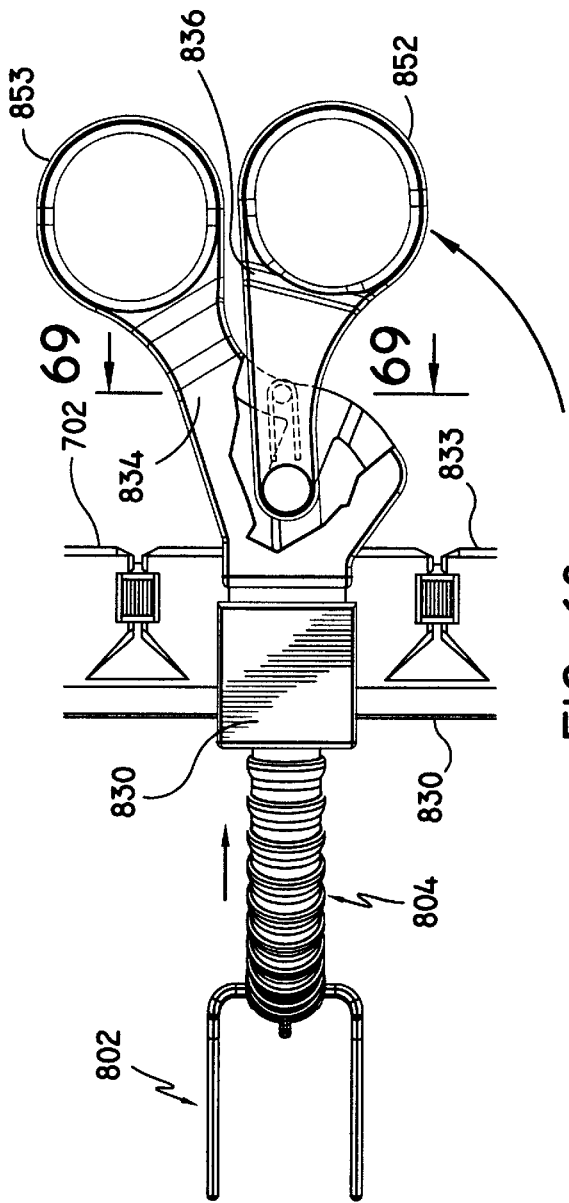

SURGICAL RETRACTOR INCLUDING COIL SPRING SUTURE MOUNT

This application is a divisional of commonly assigned, application Ser. No. 08/801,052 filed Feb. 14, 1997 by Charles R. Sherts et al., now U.S. Pat. No. 5,967,973 which application is a continuation of application Ser. No. 08/717,591 filed Sep. 23, 1996, now abandoned, which application claims priority from Provisional application Ser. No. 60/016,325, filed Apr. 26, 1996.

BACKGROUND

1. Technical Field

The subject disclosure relates to minimally invasive surgical procedures and apparatus, and more particularly to an instrument and method for performing surgery associated with the thoracic cavity.

2. Background of Related Art

The diagnosis and treatment of coronary disease and related conditions typically requires access to the heart, blood vessels and associated tissue. Such procedures include cardiopulmonary bypass, valve repair and replacement, and treatment of aneurysms. Access to the patient's thoracic cavity may be achieved by a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extended and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating window. The retractor includes a rigid frame and a translation frame slidably connected to the rigid frame. Lower and upper blades are rotatably mounted to the rigid frame and the translation frame respectively.

Once access to the thoracic cavity has been achieved, surgery on the heart may be performed. Such procedures typically require that the heart beat be arrested while maintaining circulation throughout the rest of the body. Cardioplegic fluid, such as potassium chloride (KCl) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta. Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is a complicated procedure requiring that the desired vessels be properly located and accessed. The progression of the guide wires and catheters must be closely monitored to determine proper placement. Furthermore, the introduction of catheters forms punctures in the blood vessels that must be subsequently closed, and there is an increased risk of trauma to the interior walls of the vessels in which the catheters must pass.

Therefore, a need exists for an apparatus and procedure which provides access to the thoracic cavity without causing extensive trauma to the patient. A procedure is needed to at least locally stabilize a predetermined area of the heart surface that is relatively simple to perform and incorporates instruments that are simple and reliable. Furthermore, an apparatus and procedure is needed which provides a stable framework for supporting additional instruments which may be used during these procedures.

SUMMARY

The present disclosure is directed to instruments for and methods of surgery. A retractor is provided which has a substantially planar base defining an opening for overlying an operative site on a patient, and at least one retractor blade slidably mounted to the base.

The base is positioned in the patient such that the opening therein overlies the operative site, and the operative site is percutaneously accessed through the opening. Obstructing tissue is retracted with one or more retractor blades to create an opening to provide access for the surgical procedure. A surgical instrument is provided which is engageable with the base and operable at the operative site. A surgical procedure is carried out through the opening in the base with the surgical instrument.

In a preferred embodiment, the retractor blade includes a ratchet assembly, and the method includes fixing the position of the retractor blade with respect to the base with the ratchet assembly.

The retractor blade may also include an integral blowing, irrigation or suction assembly operably positioned adjacent the blade to remove blood, fluid, etc. In another embodiment, a light assembly may be incorporated to illuminate designated portions of the surgical field.

A heart manipulator is disclosed for use in conjunction with the retractor and is releasably mountable on the base. The heart manipulator assists in atraumatically holding and positioning the heart to facilitate access thereto. In a preferred embodiment the heart manipulator includes a loop shaped frame which supports a mesh cradle.

A heart stabilizer instrument is also disclosed. This instrument is preferably configured to be mounted to the base portion and has a heart contacting surface. The heart may be contacted with the heart contacting surface to stabilize the position of a predetermined portion of the heart surface. A heart stabilizer instrument may be provided which is mounted to the base portion and movable with respect thereto. The predetermined portion of the heart surface is substantially stabilized by applying pressure thereto. In a preferred embodiment, the heart stabilizer instrument includes structure configured to compress the coronary artery, and the step of stabilizing a predetermined portion of the heart surface includes applying pressure to the coronary artery with the heart stabilizer instrument. The position of the heart stabilizing device may be locked with respect to the base.

The base may be provided to the hospital and/or surgeon in a kit form including one or more retractors. The kit may also advantageously include a heart manipulator and/or heart stabilizing device.

The surgical method may further include providing an actuator associated with the retractor blade and configured to effect linear movement of the retractor blade.

These and other features of the surgical retractor and method for heart surgery will become more readily apparent to those skilled in the art from the following detailed description of preferred embodiments of the subject disclosure.

BRIEF DESCRIPTION OF THE DRAWINGS

Various embodiments of the subject surgical apparatus are described herein with reference to the drawings wherein:

FIG. 2 is an enlarged perspective view with parts separated of a retractor blade assembly of the surgical retractor of FIG. 1;

FIG. 3 is an enlarged cross-sections view of a portion of the retractor blade assembly, illustrating the mounting of the retractor blade assembly on the base;

FIG. 4 is an enlarged cross-sectional view taken along line 4—4 of FIG. 1 of the retractor blade assembly mounted to the base;

FIG. 5 is an enlarged top view, illustrating the radially inward movement of the retractor blade with respect to the base;

FIG. 6 is an enlarged top view, illustrating the ratchet on the retractor blade in engagement with the pawl member associated with the base;

FIG. 7 is an enlarged top view, illustrating the pawl member associated with the base moved out of engagement with the retractor blade assembly;

FIG. 8 is a perspective view of one embodiment of a heart manipulator mounted to a base;

FIG. 9 is a perspective view of a heart manipulator mounted to the base and constructed in accordance with another embodiment;

FIG. 20 is an enlarged perspective view with parts separated of the retractor blade assembly;

FIG. 21 is an enlarged perspective view from below of the retraction knob, illustrating the pinion gearing disposed thereon;

FIG. 22 is an enlarged cross-sectional view of the retractor blade assembly mounted to the base;

FIG. 23 is an enlarged cross-sectional view of the retractor blade assembly in the process of being mounted to the base;

FIG. 24 is an enlarged top view illustrating the radially outward translation of the retractor blade;

FIG. 25 is an enlarged top view of the pawl member associated with the base in engagement with the retractor blade;

FIG. 26 is an enlarged top view, illustrating the pawl member moved out of engagement with the retractor blade;

FIG. 30 is an enlarged cross-sectional view of the mounting assembly of the heart stabilizer instrument of FIG. 29 in an unlocked position;

FIG. 31 is an enlarged cross-sections view of the mounting assembly of the heart stabilizer instrument of FIG. 29 in a locked position;

FIG. 32 is a cross-sectional view taken along line 32—32 of FIG. 31 illustrating the mounting to the base;

FIG. 36 is an enlarged side cross-sectional view of the retractor blade assembly, illustrating the positioning adjacent a rib and the mounting of the retractor blade assembly on the base;

FIG. 37 is an enlarged side cross-section view of the retractor blade assembly mounted to the base and in the process of retracting a rib;

FIG. 42 is a perspective view with parts separated of the heart stabilizer instrument of FIG. 41;

FIG. 42A is a perspective view of the toggle member, illustrating the cable mounting configuration;

FIG. 44 is a side view in partial cross-section of the heart stabilizer instrument in an unlocked configuration;

FIG. 45 is an enlarged cross-sectional view of the toggle mechanism in an unlocked configuration;

FIG. 46 is an enlarged cross-sectional view of a portion of the articulating arm, illustrating the cable in a loose configuration corresponding to the unlocked configuration of FIGS. 44–45;

FIG. 50 is an perspective view of a heart stabilizer instrument mounted to the base in accordance with another embodiment of the present disclosure;

FIG. 59 is a perspective view of another embodiment of a heart stabilizer instrument of FIG. 59, illustrating a positioning flange formed thereon;

FIG. 60 is an enlarged perspective view of a portion of the heart stabilizer instrument of FIG. 59, illustrating a positioning flange formed thereon;

FIG. 61 is a perspective view with parts separated of the heart stabilizer instrument of FIG. 59;

FIG. 62 is a perspective view of the mounting flange member of the heart stabilizer instrument of FIG. 59;

FIG. 63 is a perspective view of the movable handle of the heart stabilizer instrument of FIG. 59;

FIG. 64 is a top plan view in partial cross-section of the heart stabilizer instrument of FIG. 59 with the movable handle in the unlocked unstressed position;

FIG. 65 is a cross-sectional view taken along line 65–65 of FIG. 64, illustrating the relative position of the handle spring member;

FIG. 66 is a top plan view in partial cross-section of the heart stabilizer instrument of FIG. 59 with the movable handle in the locked unstressed position;

FIG. 67 is a cross-sectional view taken along line 67—67 of FIG. 66, illustrating the relative position of the handle spring member;

FIG. 68 is a top plan view in partial cross-section of the heart stabilizer instrument of FIG. 59 with the movable handle in the locked and stressed position;

FIG. 69 is a cross-sectional view taken along line 69—69 of FIG. 68, illustrating the relative position of the handle spring member;

DETAILED DESCRIPTION OF PREFERRED EMBODIMENTS

The preferred embodiments of the apparatus disclosed herein will be discussed in terms of procedures and apparatus for heart surgery. However, the subject disclosure should not be limited to an apparatus for use in conjunction with such heart surgery, but may find application in surgery wherein access to the surgical site is achieved through a small incision and retraction of the surrounding tissues and/or bone is desired.

Figure 1:
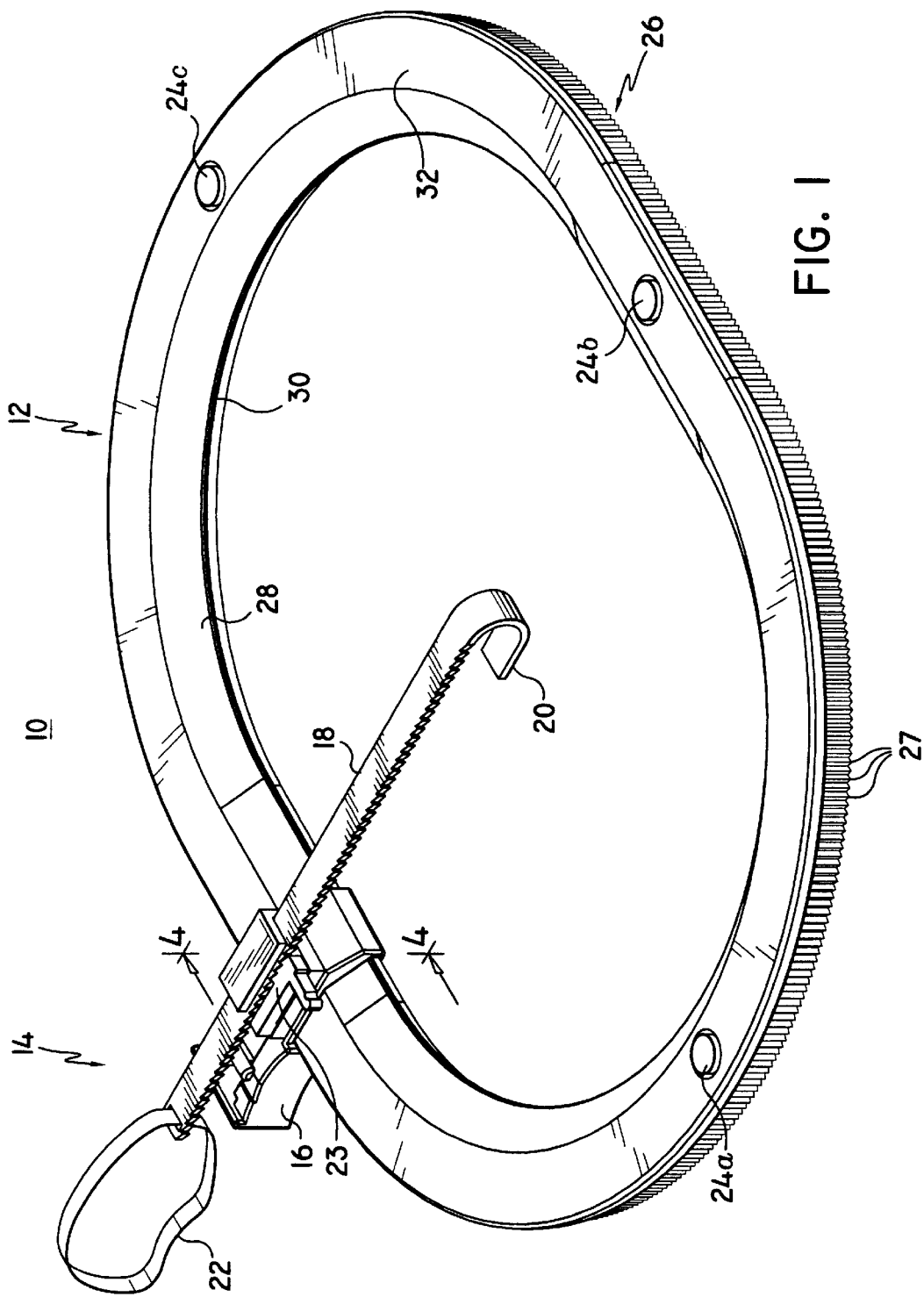
FIG. 1 is a perspective view of a surgical retractor constructed in accordance with a first embodiment of the subject disclosure.

Referring now in detail to the drawings in which like reference numbers identify similar or identical elements, a first embodiment of the surgical retractor of the subject disclosure is illustrated in FIG. 1, and is designated generally by reference numeral 10. Surgical retractor 10 has base 12 and retractor blade assembly 14, including mounting assembly 16 and retractor blade 18. As will be described below, base 12 in this embodiment is configured to be placed on the chest of a patient surrounding an incision. Retractor blade 18 includes hook 20 configured for atraumatically engaging a rib. Strap 22 assists the surgeon in drawing the retractor blade 18 radially outward and retracting a rib therewith. One-way ratchet assembly 23 on mounting assembly 16 retains retractor blade 18 in position. Base 12 is also configured to receive surgical instruments for mounting thereon, as will be described below.

Base 12 preferably has a closed shape, such as an oval configuration as shown, or a circle, polygon, or the like. Base 12 is sized suficiently large in order to enclose sufficient area to provide access to the operative site. The bottom portion of base 12 is preferably configured to permit placement directly on the skin of the patient with the base substantially flush with the patient's skin. Suture mounts 24a, 24b, 24c may be provided at several locations on the base 12 to permit suture tie down of internal tissue structures such as the pericardial sac. Outer periphery 26 of base 12 includes a series of outwardly extending teeth 27 formed thereon to provide additional stability to the positioning of mounting assembly 16 and other instruments on base 12. Base 12 also includes a beveled inner surface 28 with an inner lip 30, and top surface 32. Base 12 has a low profile when placed on the body. Base 12 is rigidly supported by pressure from retractor blade assembly 14 on the ribs in three or four locations. Preferably, three retractor blade assemblies are disposed on base 12 at 120° apart. Retractor blade assemblies may be disposed 90° apart.

Turning now to FIG. 2, mounting assembly 16 permits quick and stable mounting of the retractor blade assembly to base 12. Mounting assembly 16 includes mounting bracket 34, retainer block 36, and retainer spring 38. Gripping flange 40 on mounting bracket 34 is configured to engage inner lip 30 of base 12 (FIGS. 3 and 4). Sleeve 42 forms an open-sided channel 44 for sliding reception of retractor blade 18. Pawl member 46 is formed on mounting bracket 34 and has a series of engaging teeth 48 which communicate with the open side of channel 44 for engaging retractor blade 18, as will be described below. Mounting bracket 34 defines a cavity 49 for mounting retainer block 36 therein. Cavity 49 is partially defined by outer retainer wall 50 with upper flange 51 and by inner wall 52 having aperture 53. Retainer block 36 is radially slidable within cavity 49 and is biased inward by retainer spring 38 such that engagement teeth 54 on retainer block 36 protrude through aperture 53, to engage teeth 27 provided on periphery 26 of base 12. Retainer block 36 also includes handle 56 which permits the surgeon to move retainer block 36 towards retainer wall 50 against the bias of retainer spring 38, in order to disengage teeth 54 from base 12.

Retractor blade 18 includes curved hook 20 on a distal end portion and slot 57 on a proximal end portion to receive flexible assist strap 22 therethrough. A series of ratchet teeth 58 are provided on an edge of retractor blade 18 and engage teeth 48 of pawl member 46 when retractor blade 18 is disposed in channel 44 of mounting bracket 34.

As illustrated in FIGS. 3–4, mounting assembly 16 is mounted to base 12 in a simple, one-handed operation. FIG. 3 illustrates retainer block 36 displaced towards retainer wall 50 against the normal bias of retainer spring 38. Handle 56 of retainer block 36 facilitates approximation of retainer wall 50 with flange 51 of retainer wall 50. Mounting assembly 16 is lowered onto base 12 at an angle as shown such that gripping flange 40 engages inner lip 30 of base 12. Engagement teeth 54 are angled to permit camming over outer lip 60. FIG. 4 illustrates mounting assembly 16 into position with respect to base 12, upon which retainer block 36 is released, which thereby returns inward towards base 12 under the normal bias of spring 38. Engagement teeth 54 pass under outer lip 60 and engage teeth 27 on periphery 26 of base 12.

Turning to FIGS. 5–7, the progression of retractor blade 18 with respect to mounting bracket 34 is illustrated. Ratchet assembly 23 includes pawl 46 on mounting bracket 34 and teeth 58 on retractor blade 18. Pawl 46 is normally biased towards retractor blade 18. Pawl teeth 48 and retractor blade teeth 58 are each configured with a sloping portion and a straight portion. This permits retractor blade 18 to be progressively displaced in a radially outward direction as indicated by arrow "O" in FIG. 5. As illustrated in FIG. 6, radially inward displacement of retractor blade 18 is prevented by engagement of pawl teeth 48 and retractor blade teeth 58 under the normal bias of pawl 46. The arrangement of teeth, as shown in FIGS. 5–6 permits retraction of a rib or other body structure and prevents slipping of or loss of retraction force exerted by retractor 18. As illustrated in FIG. 7, retractor blade 18 is permitted to displace radially inward as indicated by arrow "I" when pawl tab 62 is rotated clockwise causing it to move away from retractor blade 18 against its normal bias by actuation of tab 62. Unrestricted movement of retractor blade 18 is permitted in both radially inward and radially outward directions when tab 62 is moved to the position of FIG. 7.

Figure 14:
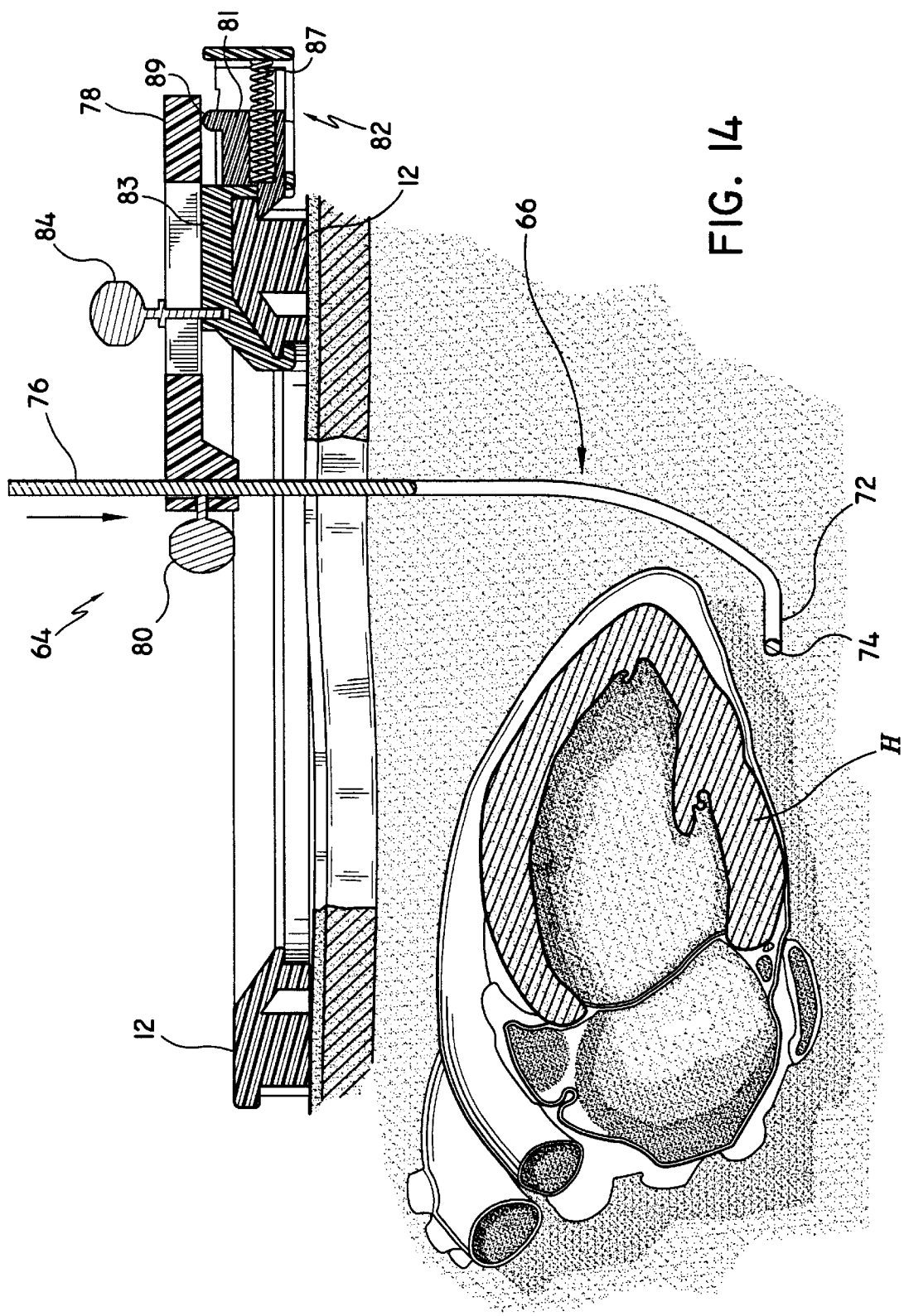
FIG. 14 is an enlarged side view in cross-section, illustrating a heart manipulator mounted to the base and spaced from the heart.

FIG. 8 illustrates a heart manipulator 64 for use in conjunction with surgical retractor 10 and for mounting on base 12. Heart manipulator 64 includes loop shaped frame 66 that supports mesh surface 68. Frame 66 and mesh surface 68 together form a heart contacting surface for manipulating the heart therewith. Preferably, frame 66 includes upright portion 70, generally horizontally extending portion 72 and atraumatic curved end portion 74, which provide a surface for engaging and manipulating the heart. Frame 66 is supported by mounting bar 76 which is slidably received in support bracket 78 for height adjustment. Set screw 80 secures mounting bar 76 with respect to support bracket 78. Radial positioning of support bracket 78 and heart manipulator 64 is achieved by slidable mounting of support bracket 78 on mounting assembly 82 which mounts to base 12 in a manner substantially similar to that of mounting assembly 16 described above with respect to FIGS. 3–4. Set screw 84 secures the radial position of heart manipulator 64 with respect to mounting assembly 82. More particularly, support bracket 78 has an elongated slot 79 formed therein which enables bracket 78 to slide radially with respect to set screw 84 and mounting assembly 82. As shown in FIG. 14, mounting assembly 82, like mounting assembly 16, has a mounting bracket 83 which engages inner lip 30 of base 12, retainer block 81, and retainer spring 87. Handle 89 of retainer block 81 enables the engagement and disengagement of mounting assembly 82 in the same manner as mounting assembly 16 described above.

Turning to FIG. 9, a heart manipulator 90 is shown in accordance with another preferred embodiment. Loop frame 66 and mounting assembly 82 are substantially as described above with respect to heart manipulator 64 in FIG. 8. Mounting bar 92 supports frame 66 and has substantially right angled bend 94 for slidable insertion in support bracket 96. Radial position of heart manipulator 90 is achieved by sliding mounting bar 92 with respect to support bracket 96 and secured thereto by set screw 98. Although height adjustment of heart manipulator 90 is not provided, access to the operative site is enhanced by the one-piece design of mounting bar 92.

Figure 10:
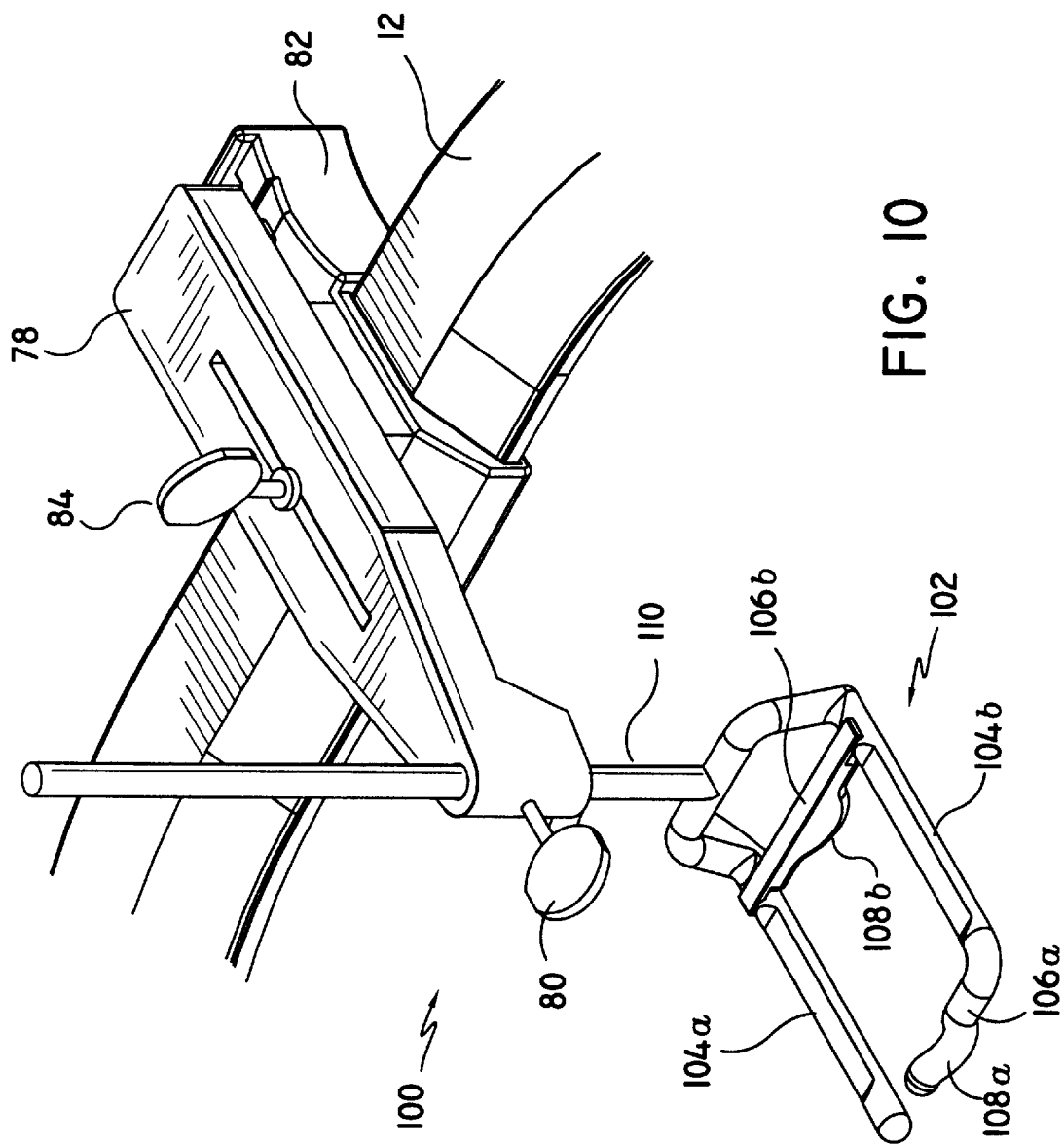
FIG. 10 is an enlarged perspective view of a heart stabilizer instrument mounted to the base.

FIG. 10 illustrates a heart stabilizer instrument 100, configured to apply pressure to the coronary artery to reduce blood flow in the artery to allow anastomosis to the coronary artery and to reduce movement of the heart muscle between legs 104a, 104b in order to enable the surgeon to perform cardiovascular surgery. Heart stabilizer instrument 100 is mounted to base 12 by mounting assembly 82, substantially as described above. Heart stabilizer instrument 100 includes frame 102 supporting legs 104a and 104b and transverse bars 106a and 106b. Protrusion 108a is formed on transverse bar 106a, and protrusion 108b is formed on transverse bar 106b. Protrusions 108a and 108b have an atraumatic convex heart contacting surface and permit the exertion of localized pressure on the coronary artery when frame 102 is compressed on the surface of the heart. Mounting bar 110 is slidably received in support bracket 78 and secured with respect thereto by set screw 80. Radial positioning of heart stabilizer instrument 100 with respect to mounting assembly 82 is secured by a coupling means, such as set screw 84.

Figure 11:
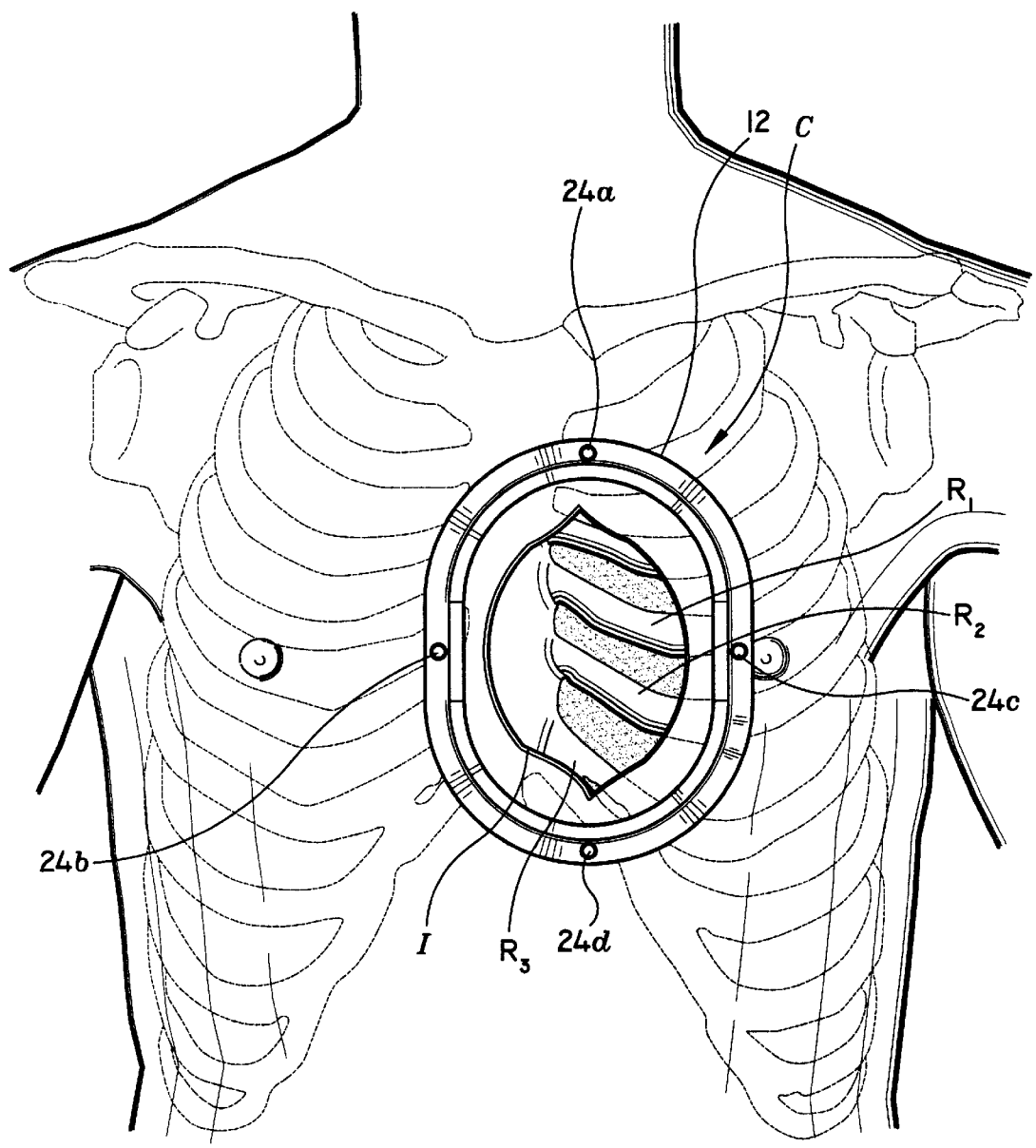
FIG. 11 is a top view in reduced scale of the base portion positioned on the patient's chest.

Turning now to FIG. 11, the operation of the surgical retractor 10 will now be described. Conventional surgical techniques are used to determine the location of the incision I accessing the chest cavity C. Base 12 is placed on the chest of the patient with the opening overlying the operative site. Incision I is made, exposing several ribs $R_1$, $R_2$, and $R_3$.

Figure 12:
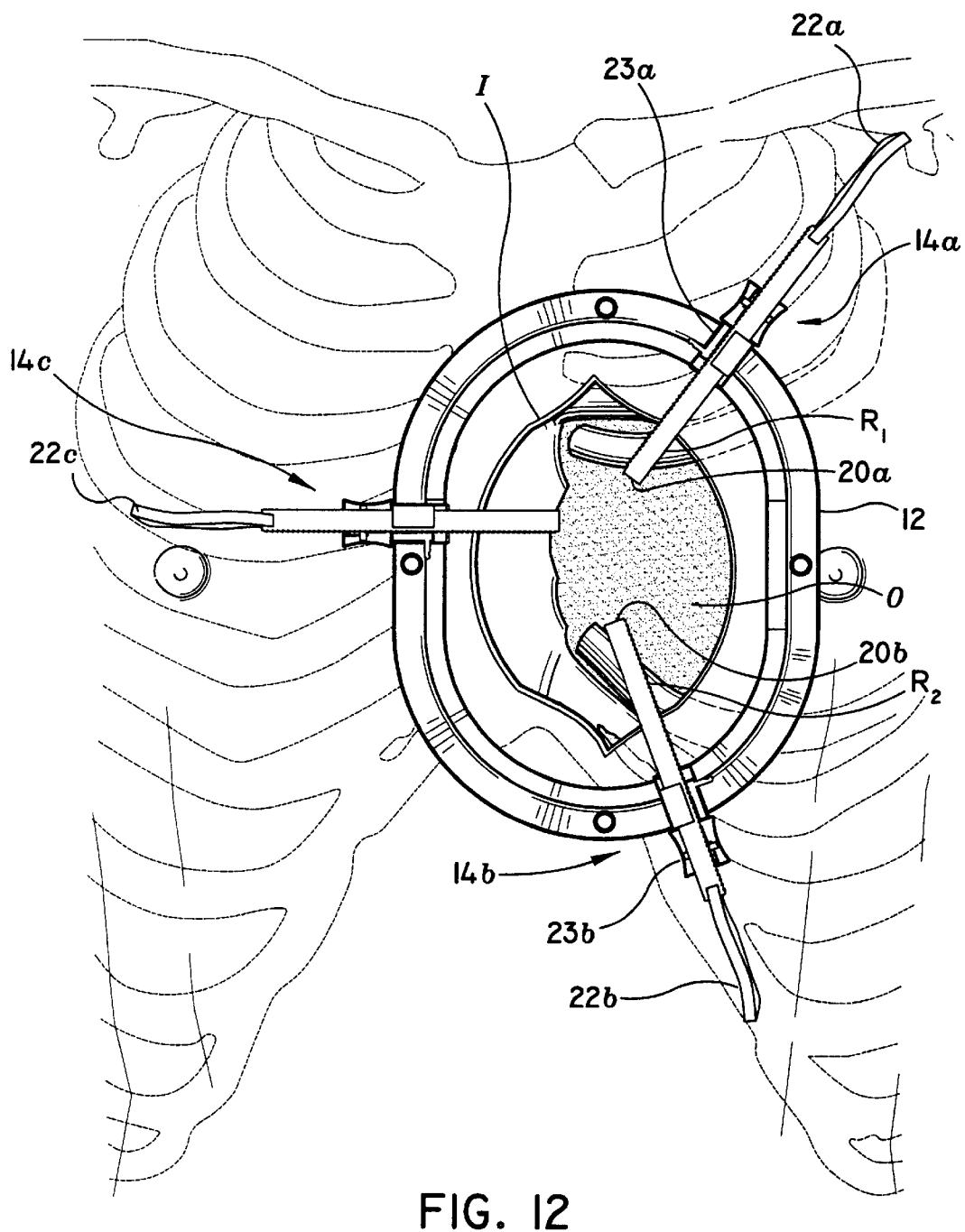
FIG. 12 is a top view, illustrating retractor blade assemblies mounted to the base portion and retracting the patient's ribs.

As illustrated in FIG. 12, retractor assemblies 14a, 14b, and 14c are mounted to base 12 at various location. Hook 20a is positioned around a rib $R_1$. Assist strap 22a is used to provide a grip for the surgeon to deflect and retract rib $R_1$ by pulling retractor blade 18 radially outward. One way ratchet assembly 23a maintains retractor blade 18 and consequently rib $R_1$ in position. Rib $R_2$ is retracted in a substantially identical manner by hook 20b on retractor assembly 14b. Additional retractors are mounted and used to retract ribs until a sufficiently large opening O in chest cavity C is defined in order to provide access to the heart. Although three retractors are shown, it is contemplated that a fewer number or a greater number of retractors could be utilized, and these retractors can be mounted anywhere along base 12 in order to perform their function. For example, the sternum and the fourth and fifth ribs can be spread apart to create a window. Alternatively, the fourth and fifth ribs are cut from the sternum and spread to create a larger window. Alternatively, a fifth rib can be cut, and the sternum and the fourth and sixth ribs are spread.

Base 12 is at least partially held in position over the operative site by tension created in retracting the ribs by retractor blades 18. Internal tissue structures may be tied down utilizing sutures passing through securement points 24a, 24b, 24c and 24d.

Figure 13:
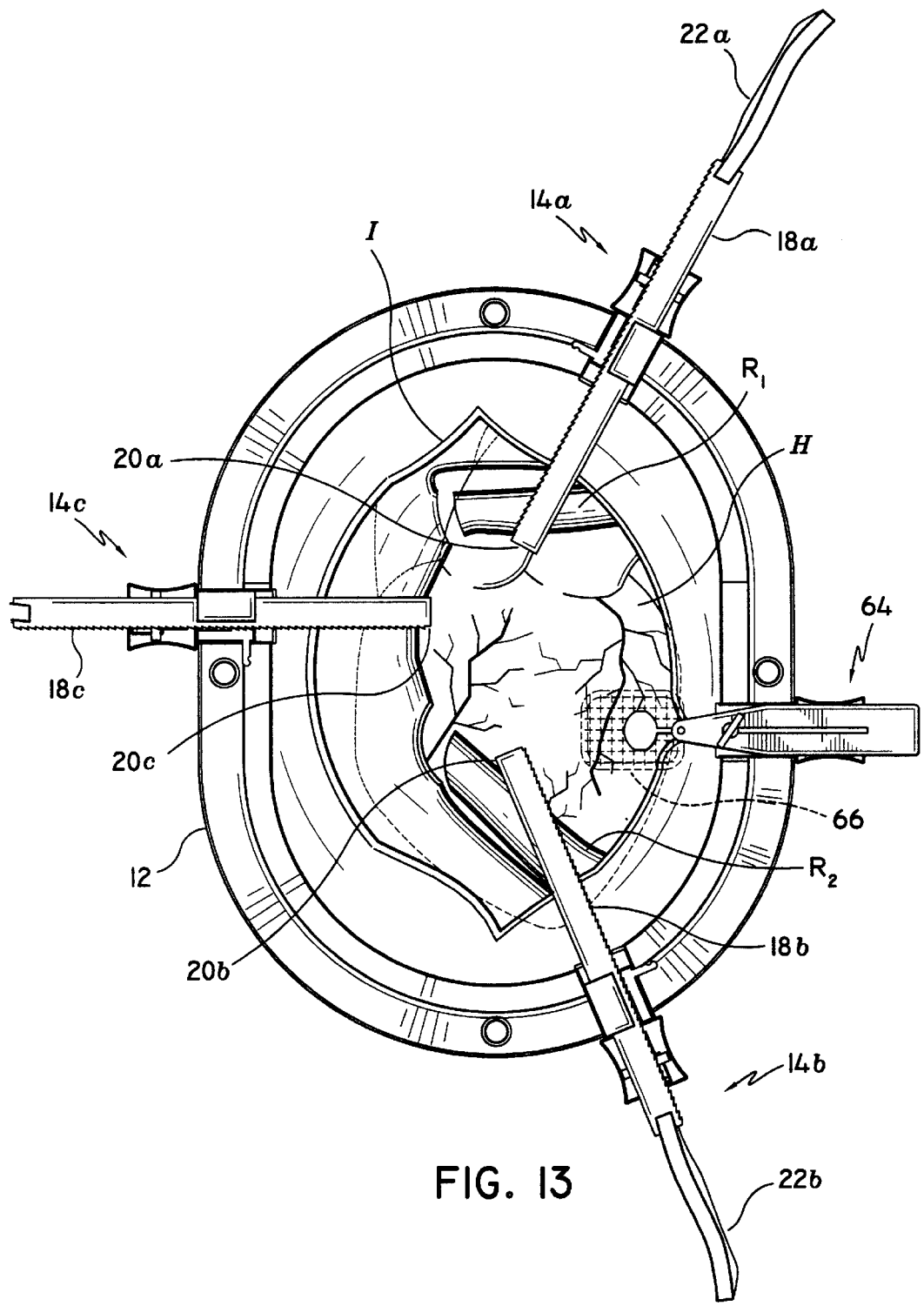
FIG. 13 is a top view, illustrating a heart manipulator in position adjacent the patient's heart.
Figure 15:
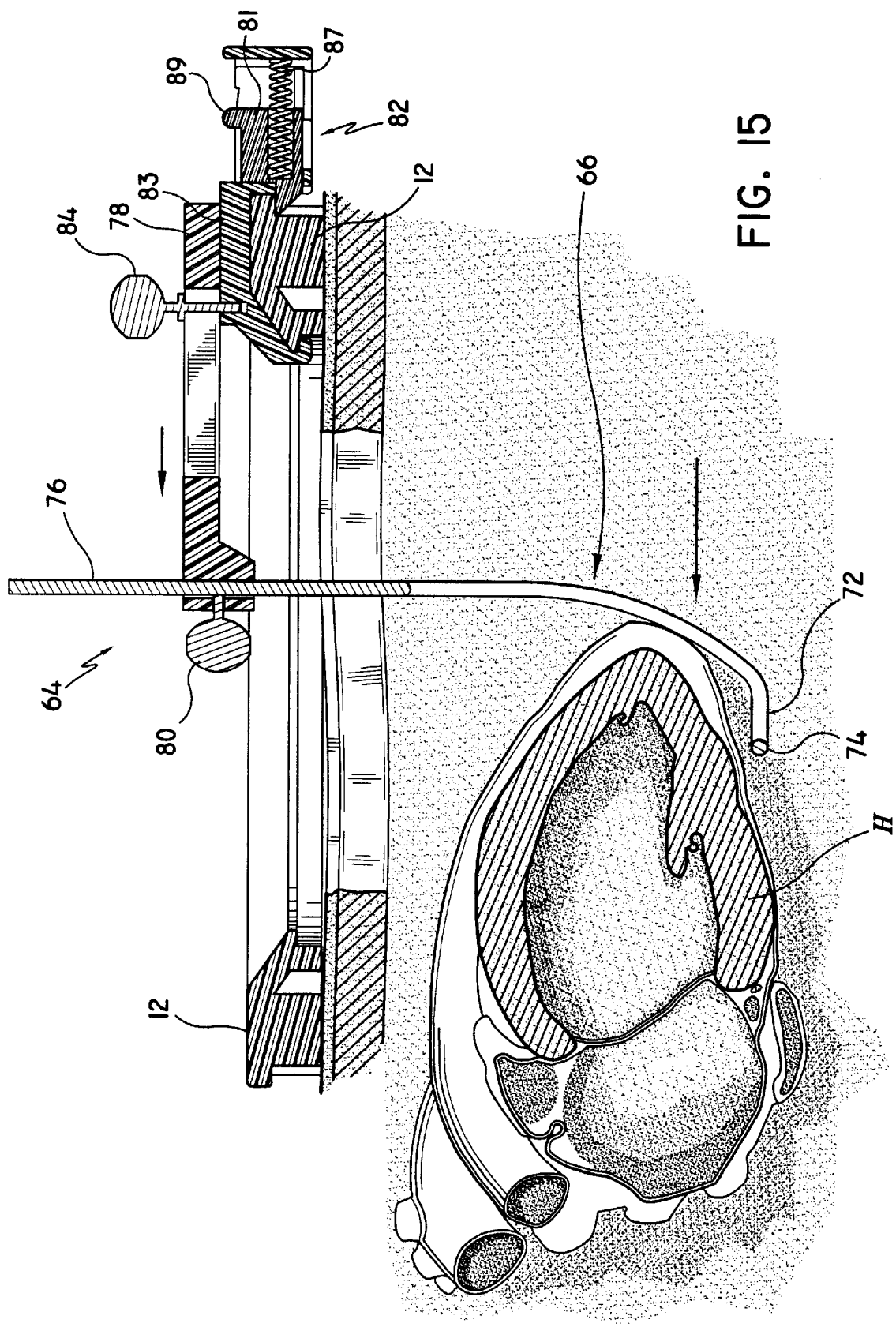
FIG. 15 is an enlarged side view in cross-section, illustrating a heart manipulator in contact with the heart.

Turning now to FIG. 13, heart manipulator 64 is mounted to base 12 in order to manipulate the position of heart H to facilitate the surgery. With reference to FIG. 14, heart manipulator 64 is positioned in the chest cavity adjacent heart H. Frame 66 and mounting bar 76 can be lowered and fixed by a set screw 80 such that horizontal portion 72 and curved end portion 74 are positioned slightly underneath heart H. As illustrated in FIG. 15, heart manipulator 64 is displaced radially inward and against heart H by loosening set screw 84 and sliding mounting bar 92 in the direction of the arrow. When sufficient pressure is placed on the heart to substantially fix its position, heart manipulator 64 is secured by the tightening of set screw 84.

Figure 16:
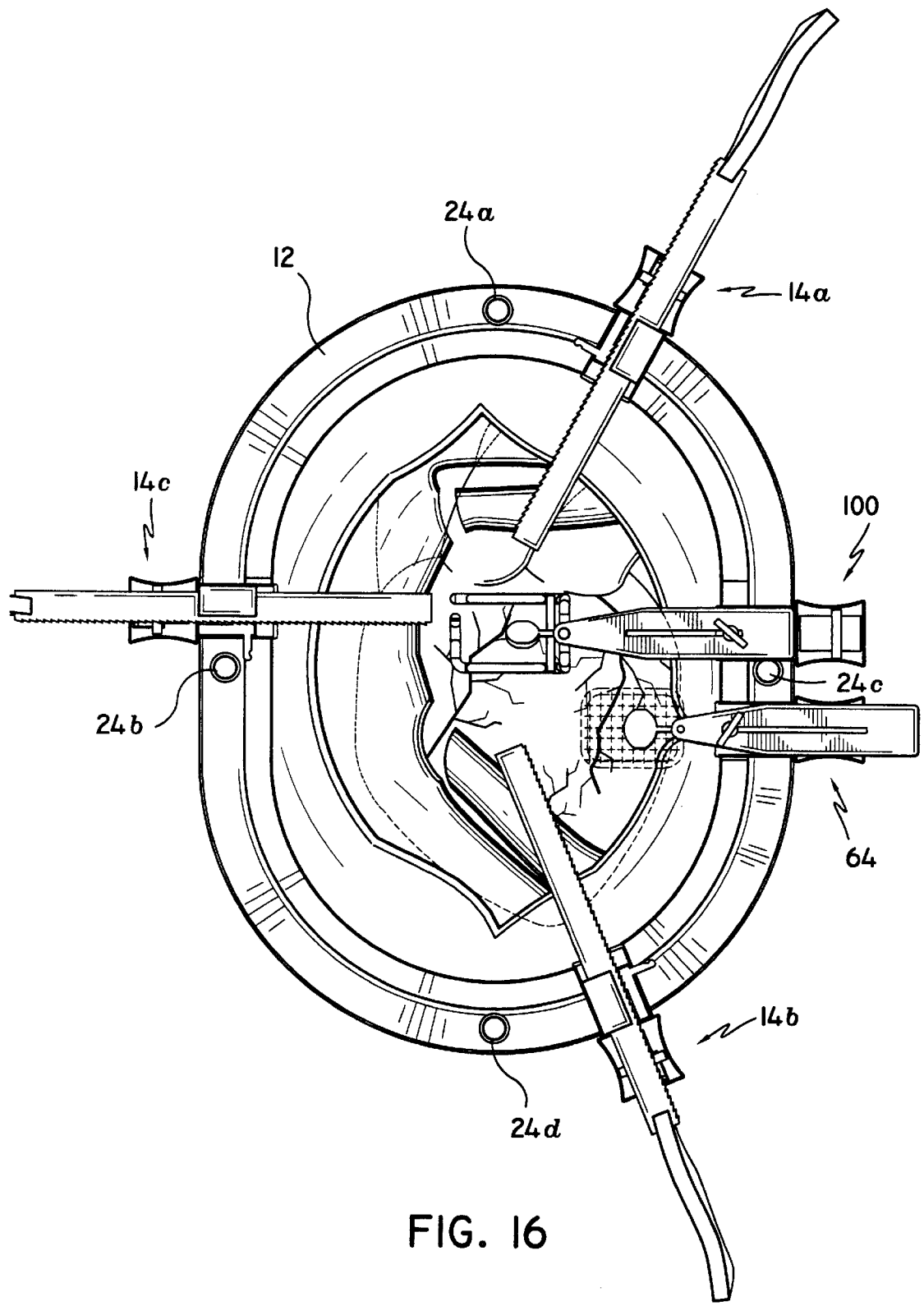
FIG. 16 is a top view, illustrating the heart stabilizer instrument of FIG. 10 mounted to the base.
Figure 17:
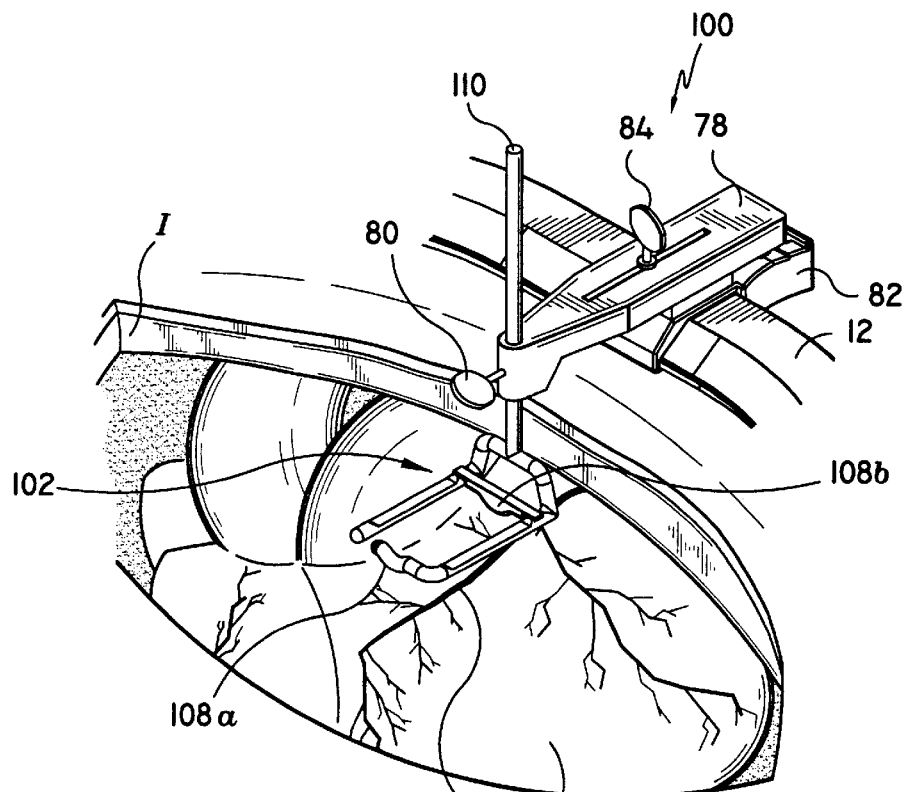
FIG. 17 is a perspective view of the heart stabilizer instrument of FIG. 10 mounted to the base and spaced from the heart.

With the heart manipulated to the desired position, FIG. 16 illustrates the mounting of heart stabilizer instrument 100 to base 12. As illustrated in FIG. 17, heart stabilizer instrument 100 is positioned over heart H and more particularly, over coronary artery A. The radial positioning of instrument 100 is accomplished by relative movement of support bracket 78 with respect to mounting assembly 82.

Figure 18:
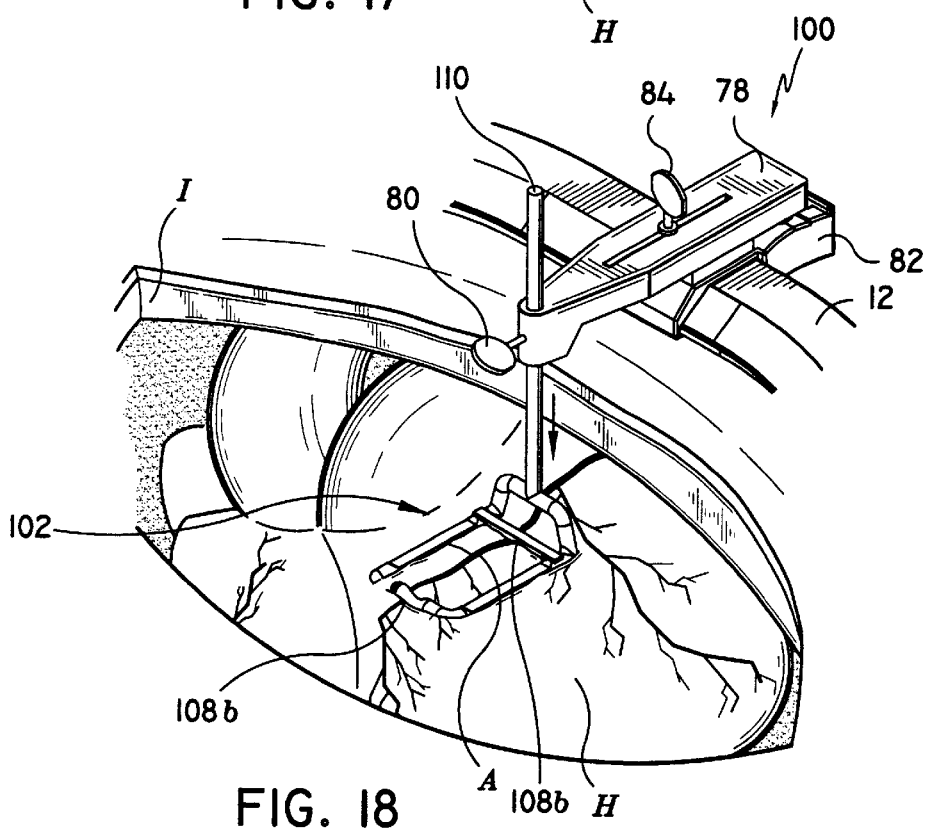
FIG. 18 is a perspective view of the heart stabilizer instrument of FIG. 10 in contact with the heart.

As illustrated in FIG. 18, frame 102 and mounting bar 110 are lowered with respect to support bracket 78 such that frame 102 applies direct pressure on heart H. Protrusions 108a and 108b localize this pressure to substantially restrict the flow of blood from coronary artery A and 104a and 104b reduce movement of the surface of the heart muscle to facilitate the surgery. Heart movement is restricted by virtue of the leg pressure and the anti-slip texture of the legs 104a and 104b. The position of instrument 100 may be locked with respect to the base as set forth in detail below.

Figure 19:
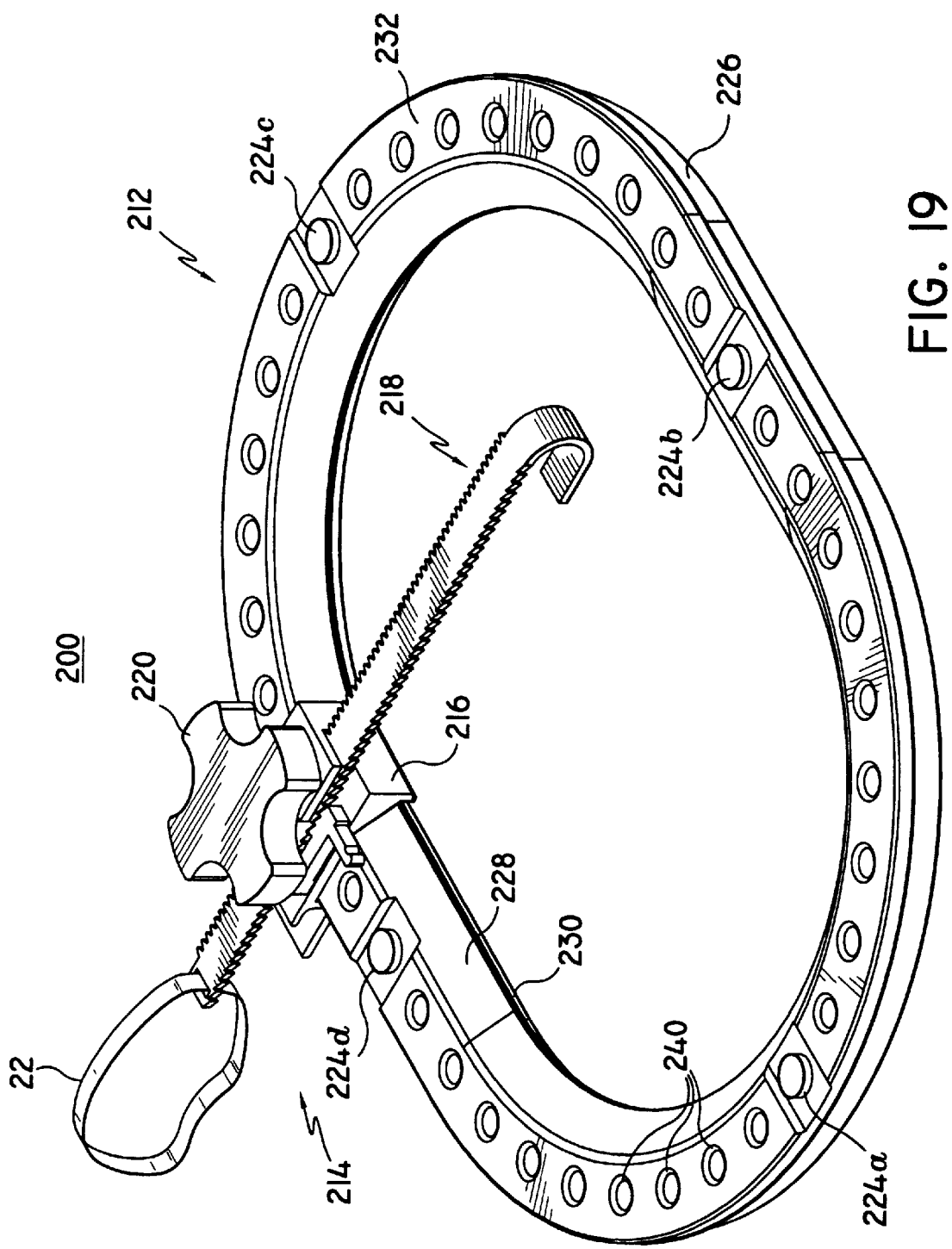
FIG. 19 is a perspective view of a surgical retractor assembly and base constructed in accordance with another embodiment of the subject disclosure.

Turning now to FIGS. 19–33, another preferred embodiment of the surgical retractor is disclosed at reference numeral 200. Instrument 200 operates substantially as described above with regard to instrument 10, with the differences described hereinbelow. In particular, FIG. 19 illustrates surgical retractor 200 having base 212 and retractor blade assembly 214, which includes mounting bracket 216, retractor blade 218 and retraction knob 220. The provision of retraction knob 220 enables the surgeon to achieve additional mechanical advantage in retracting a rib.

Base 212 includes suture mounting portions 224a, 224b, 224c and 224d for securing base 212 adjacent the surgical site. Base 212 further includes beveled inner surface 228 with inner lip 230 and top surface 232 in which a series of cylindrical recesses or openings 240 are defined.

As illustrated in FIG. 20, mounting bracket 216 includes sleeve 242 defining open-sided channel 244 for sliding reception of retractor blade 218. Pawl member 246 has a series of ratchet teeth 248 configured to engage ratchet teeth 258 on retractor blade 218 when blade 218 is slidably inserted in channel 244.

Retraction knob 220 is rotatably positioned in aperture 236 in mounting bracket 216. With reference to FIG. 20 in conjunction with FIG. 21, retraction knob 220 includes pinion gear 260 which cooperates with rack 262 provided on retractor blade 218. As will be described below, rotation of knob 220 provides additional mechanical advantage in cooperation with one-way ratchet mechanism 23 to retract and/or advance retractor blade 218.

As illustrated in FIGS. 22–23, retractor blade assembly 214 is mounted to base 212 in a simple, one-handed motion. Mounting bracket 216 includes pin 264 on a bottom portion thereof dimensioned to be received in one of cylindrical recesses 240 in base portion 212. The length of pin 264 is preferably substantially equivalent to the depth of recess 240 to provide stability to mounting bracket 216. In addition, wedge shaped inner portion 266 of mounting bracket 216 cooperates with beveled inner surface 228 of base 212 to facilitate positioning and to provide resistance against tilting of retractor blade 218. Mounting bracket 216 is further secured in position by tab 270 which includes a flange 272 which engages outer rim 274 of base 212. As illustrated in FIG. 23, removal and placement of mounting bracket 216 is accomplished by deflecting flange 272 of tab 270 clear of outer rim 274. Tab 220 includes rigid lever arm 276 which facilitates such deflection of tab 270.

Turning to FIGS. 24–26, the interaction of retractor blade 218 with respect to mounting bracket 216 is illustrated. Ratchet assembly 223, which includes pawl 246 and sloping teeth 258 function substantially as described above with respect to FIG. 5, and permits retractor blade 218 to be progressively displaced radially outwardly while preventing radially inward displacement. Initially, assist straps 22 (See, FIG. 19) are used by the surgeon to retract a rib. Retracting blade 218 is displaced radially outwardly as far as possible given the strength of the surgeon. Subsequently, additional retraction force can be applied to the rib by rotation of retraction knob 220. Pinion gear 260 disposed on knob 220 engages rack 262 on retraction blade 218 and provides additional leverage to the surgeon. As illustrated in FIG. 25, pawl 246 is normally biased against retraction blade 218 such that ratchet teeth 258 on blade 218 and ratchet steel 248 on pawl 246 engage to prevent radially inward movement. It should be appreciated that knob 220 is optionally removable so it can be used to retract each retractor blade 218.

FIG. 26 illustrates that pawl 246 may be rotated away from retraction blade 218 by pivoting lever 262 to disengage teeth 258 and 248. Unrestricted radial movement of retraction blade 218 is facilitated thereby.

Figure 27:
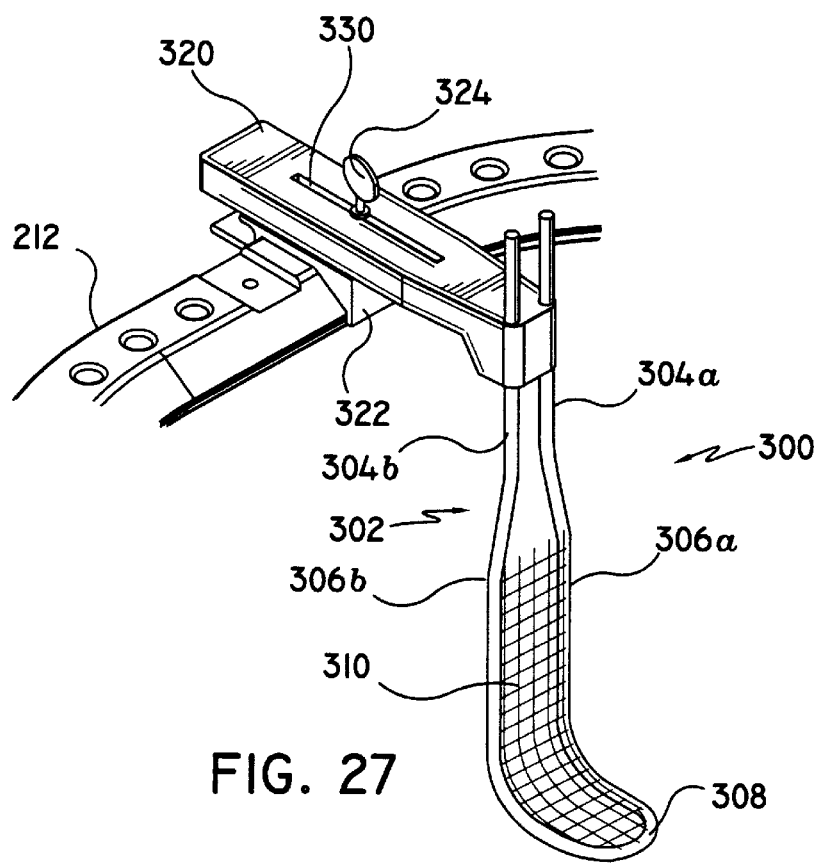
FIG. 27 is a perspective view of a heart manipulator constructed in accordance with yet another embodiment of the subject disclosure.
Figure 28:
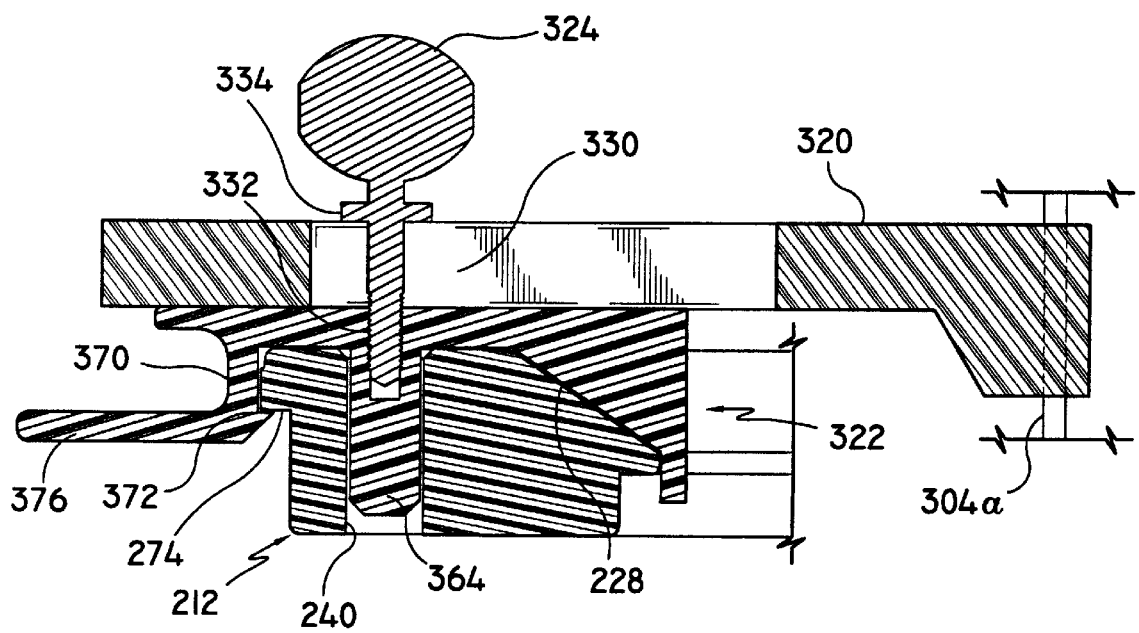
FIG. 28 is an enlarged cross-sectional view of the mounting assembly for the heart manipulator of FIG. 27.

FIGS. 27–28 illustrated another embodiment of a heart manipulator instrument designated by reference number 300. Heart manipulator 300 is used to manipulate the position of the heart and operates substantially as described above with regard to heart manipulator 64, with the differences described below. In particular, hear manipulator 300 includes frame member 302, formed in a modified "U"

configuration having an upright portion wherein the bars are parallel, including closely spaced mounting portions 304a and 304b, more widely spaced mesh supporting portions 306a and 306b, and a curved horizontally extending portion 308. Mesh supporting portions 306a and 306b and horizontally extending portion 308 support a mesh surface 310 therebetween. Mounting portions 304a and 304b are snap fit within bores formed in support bracket 320. It is contemplated that members 304a and 304b may be slidable with respect to bracket 320 and secured with set screws (not shown). Radial positioning of support bracket 320 is achieved by slidable mounting of support bracket 320 on mounting bracket 322. Set screw 324 is used to secure the radial positioning of heart manipulator 300. Elongated slot 330 allows movement of support bracket 320 with respect to set screw 324 and mounting bracket 322.

Turning now to FIG. 28, mounting bracket 322 is configured to mount on base 212 substantially as described with respect to mounting bracket 216 in FIGS. 22–23. Pin 364 of bracket 322 is received in one of openings 240 in base 212. Tab 370 includes flange 372 which removably engages outer rim 274 of base 212 and is disengaged by lever arm 376. Support bracket 320 is slidably mounted on mounting bracket 322 such that a portion of slot 330 is aligned over threaded bore 332. Set screw 324 extends through slot 330 into bore 332 and includes collar 334 which abuts a top surface of support bracket 320 to secure it against radial movement.

Figure 29:
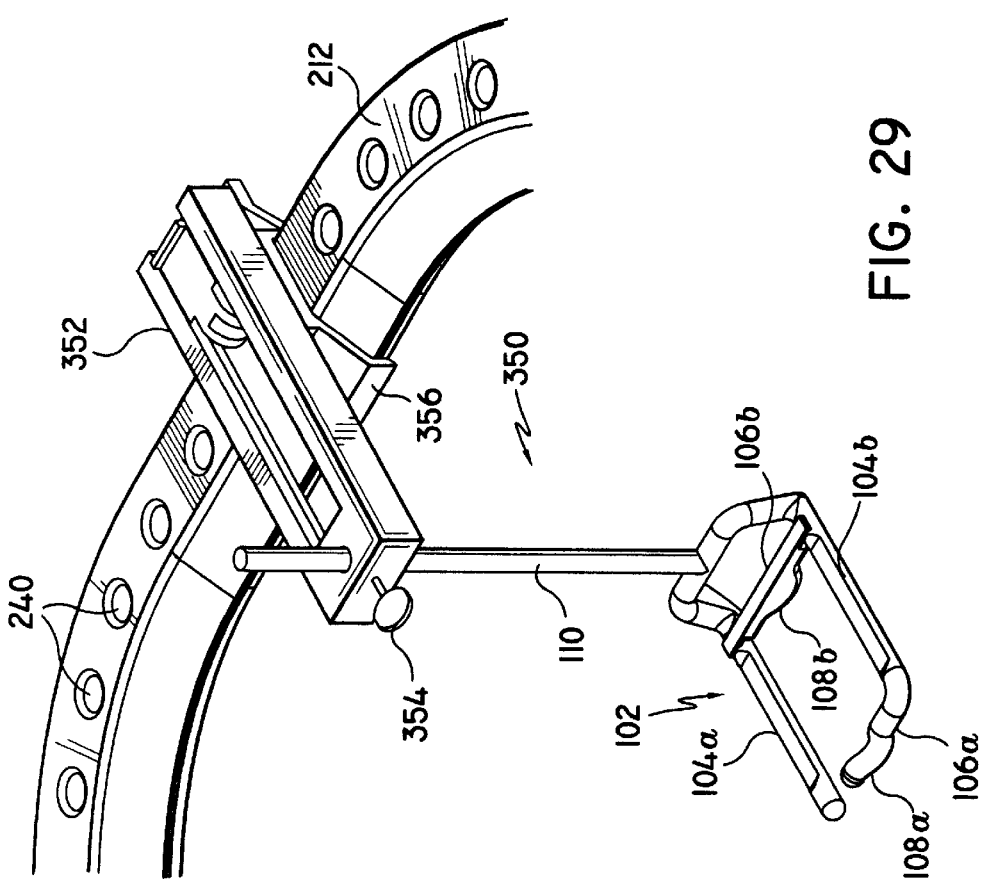
FIG. 29 is a perspective view of a heart stabilizer instrument constructed in accordance with another embodiment of the subject disclosure.

FIGS. 29–32 illustrate a heart stabilizer instrument 350 in accordance with another preferred embodiment of the subject disclosure. With reference to FIG. 29, heart stabilizer instrument 350 includes frame 102 and mounting bar 110. Frame 102 includes legs 104a and 104b and transverse bars 106a and 106b having protrusions 108a and 108b substantially as described with respect to FIG. 10, above. Mounting bar 110 is slidably received in a bore in support bracket 352 and secured with respect thereto by set screw 354. Support bracket 352 is slidable with respect to mounting bracket 356.

As illustrated in FIGS. 30–31, mounting bracket 356 is removably mounted on base portion 212 substantially as described with respect to mounting bracket 216 in FIGS. 22–23. Pin 358 is received in one of cylindrical recesses or openings 240 in base 212. Tab 360 includes flange 362 for removably engaging outer rim 274 of bore 212. Flange 362 is disengaged by actuation of lever arm 364. With reference to FIG. 32 in conjunction with FIGS. 30–31, support bracket 352 includes a pair of vertical walls 364a and 364b and a pair of horizontal walls 366a and 366b which rest on a top surface of mounting bracket 356. A lever mounting rod 368 extends upwardly from mounting bracket 356 between horizontal walls 366a and 366b. A pair of hinge pins 370a and 370b extend from rod 368 and are received in a clevis portion 372 of lever arm 374. Horizontal walls 366a, 366b of support bracket 352 are disposed between mounting bracket 356 and clevis portion 372 of lever arm 374.

With continued reference to FIGS. 30–31, clevis portion 372 is substantially circular or elliptical in lateral cross-section and is eccentrically mounted to hinge pins 370a and 370b. As illustrated in FIG. 30, when lever arm 374 is in a released position, clevis portion 372 is spaced from horizontal walls 366a and 366b and unrestricted radial movement of support bracket 352 is enabled thereby. As illustrated in FIG. 31, pivoting of lever arm 374 causes clevis portion 372 to apply a compressive force on horizontal walls 366a and 366b on top of mounting bracket 356 to thereby fix the radial position of support bracket 352 with respect to mounting bracket 356.

Figure 33:
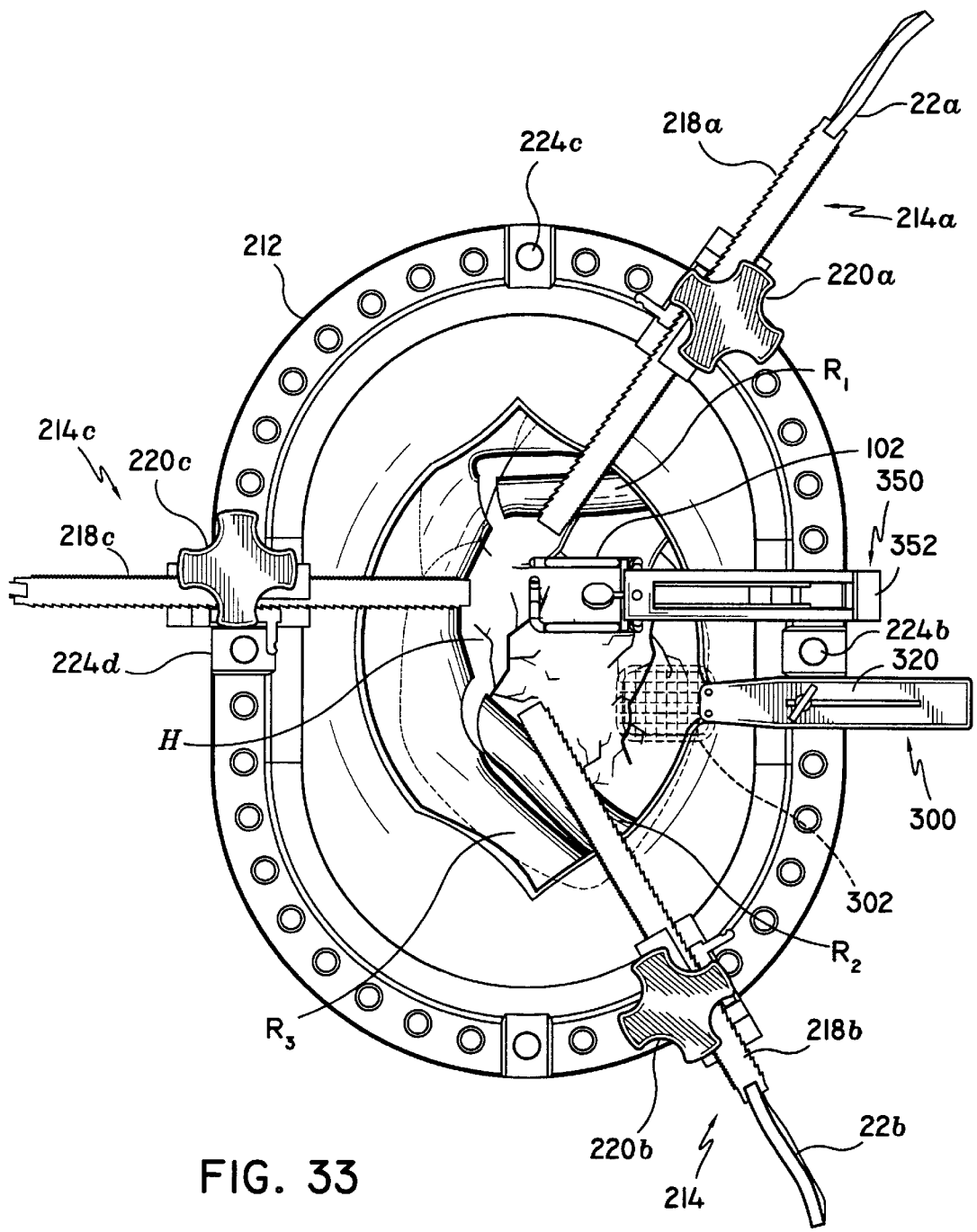
FIG. 33 is a top view of the surgical retractor positioned on the patient's chest, illustrating retractor blade assemblies, a heart manipulator and a heart stabilizer instrument mounted on the base.

Turning to FIG. 33, operation of surgical retractor 200 in conjunction with heart manipulator and heart stabilizer instrument proceeds substantially as described with respect to FIGS. 11–18. As noted above, mounting bracket 216a of retractor blade assembly 214 is placed on base 212 by actuation of lever arm 276a (not shown). Heart manipulator 200 and heart stabilizer instrument 350 are mounted to base 212 in a substantially identical manner as described above. The surgical procedure is carried out substantially as described above. Ribs $R_1$, $R_2$ and $R_3$ are retracted by the pulling of assist straps 22 and by the rotation of retraction knob 220. The position of heart H is stabilized by heart manipulator 300. Heart stabilizer instrument 350 is positioned and lowered onto heart H to apply pressure to the coronary artery and thereby substantially reduce movement (motion) of the heart within the legs. The instrument 350 may be locked with respect to the base. At this time, other surgical procedures, such as coronary bypass or valve surgery may be performed.

Figure 34:
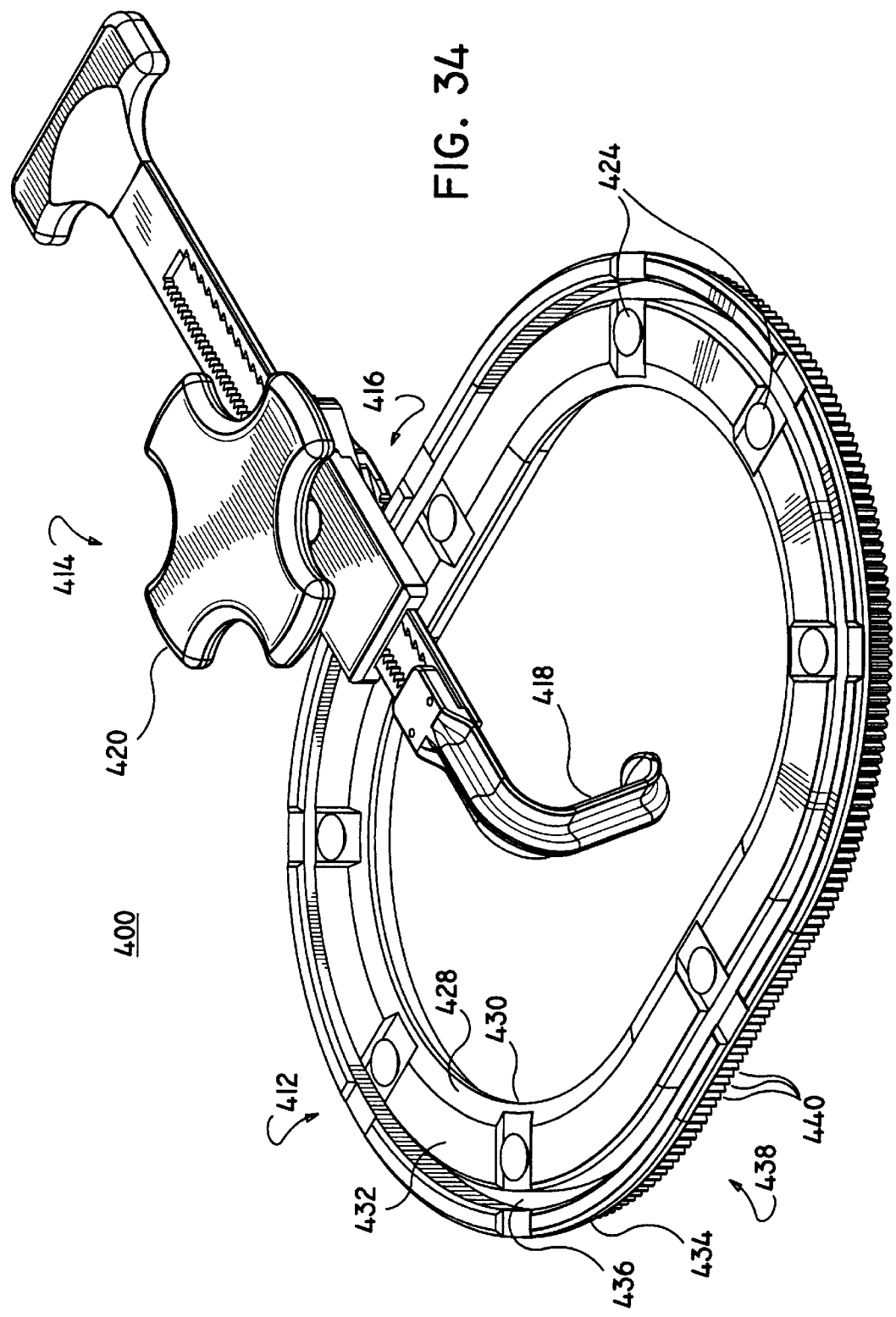
FIG. 34 is a perspective view of a surgical retractor constructed in accordance with another embodiment of the subject disclosure.

Turning now to FIGS. 34–52, another embodiment of the surgical retractor is disclosed at reference number 400. Instrument 400 operates substantially as described with regard to instrument 200, with the differences noted hereinbelow. In particular, FIG. 34 illustrates surgical retractor 400 having base 412 and retractor blade assembly 414, which includes mounting bracket 416, retractor blade 418, and retraction knob 420. The provision of retraction knob 420 enables the surgeon to achieve additional mechanical advantage in retracting a rib.

Base 412 includes suture mounting portions 424 for suture tie down of internal tissue structures. Base 412 further includes beveled inner surface 428 with inner lip or rim 430 and top surface 432, which forms an outer lip or rim 434. A channel or groove 436 is formed in top surface 432. Outer periphery 438 of base 412 includes a series of teeth 440 formed thereon.

Figure 35:
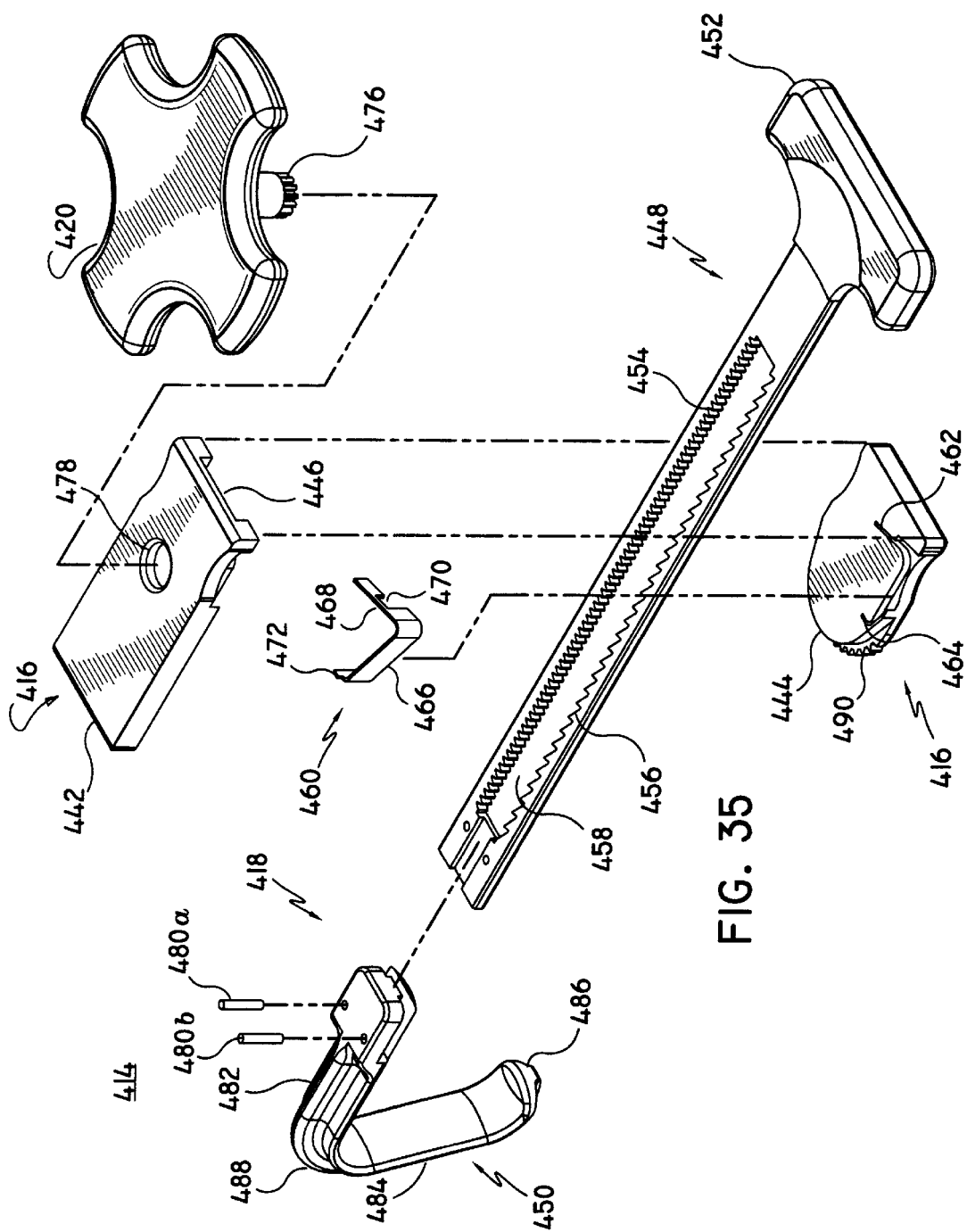
FIG. 35 is a perspective view with parts separated of a retractor blade assembly of the surgical retractor of FIG. 34.

As illustrated in FIG. 35, mounting bracket 416 includes housing 442 and mounting plate 444 which are connected and allow retractor blade 418 to slide within channel 446 defined in a lower surface of housing 442.

Retractor blade 418 includes body portion 448 and rib engaging portion 450. Body portion 448 defines a T handle 452 configured to be grasped by the surgeon in order to slide retractor blade 418 within channel 446. Body portion 448 defines a rack gearing 454 and a series of sloping ratchet teeth 456. Preferably, such gearing 454 and ratchet teeth 456 are respectively disposed along elongated channel 458 defined within body portion 448.

Ratchet teeth 456 are releasably engaged by pawl 460. Mounting plate 444 defines first channel 462 and second channel 464 for receiving pawl 460. Preferably, pawl 460 is a resilient member having a modified U-shaped configuration including crown portion 466, first leg 468 defining cut-out portion 470, and second leg 472. Second leg 472 is fixedly retained within second channel 464 having an elbow configuration. The junction of second leg 472 and crown 466 acts as a hinge or pivot such that first leg 468 is slidable within first channel 462. Pawl 460 is normally biased at this junction of second leg 472 and crown 466 such that first leg 468 is partially disposed in first channel 462. Crown 466 may be pressed by the user towards mounting plate 444 against the normal bias to slide first leg 468 further along first channel 462. Retractor blade 418 is positioned adjacent mounting plate 444, and pawl 460 is placed on top of blade 418 such that cut-out portion 470 of first leg 468 straddles a portion of blade 418 adjacent ratchet teeth 456. (See, FIG.

38) As will be described below, pawl 460 is normally biased such that first leg 468 is in engagement with one of ratchet teeth 456. Pawl 460 and ratchet teeth 456 together define a one-way ratchet mechanism 474.

Rack gearing 454 is engaged by pinion gearing 476 formed on retraction knob 420, which is position in aperture 478 defined in housing 442. As will be described below, rotation of retraction knob 420 provides additional mechanical advantage when used in cooperation with ratchet mechanism 474 to retract and/or advance retractor blade 418.

Rib engaging portion 450 is connected to body portion 448 with a dovetail joint and secured thereto with pins 480a and 480b. Alternatively, retractor blade 418 may be constructed of a single part. Rib engaging portion 450 includes a horizontal portion 482, angularly depending portion 484, and tip portion 486. Angularly depending portion 484 forms an acute angle with horizontal portion 482 to securely engage the rib. Strengthening rib or beading 448 is formed on the outside of rib engaging portion 450 to provide additional strength and to resist bending.

Referring to FIG. 35 in conjunction with FIGS. 36–37, mounting plate 444 includes a gearing 490 on a forward portion thereof to engage peripheral gear teeth 440 on base 412 (See, FIG. 34).

As illustrated in FIG. 36, base 412 is placed at the operative site on patient's chest. Rib engaging portion 450 is positioned adjacent rib R, such that angularly depending portion 484 and tip portion 486 at least partially surround rib R. Housing 442 has a flat bottom portion and is placed on upper surface 432 of base 412.

FIG. 37 illustrates the simultaneous mounting of mounting bracket 416 to base 412 and retraction of rib R towards base 412 as indicated by the arrows. Retractor blade 418 is moved radially outward with respect to base 412 while rib engaging portion 450 engages rib R. Mounting plate 444 is spaced from the bottom portion of housing 442 in order to permit mounting plate 444 to slide under outer rim 434 of base 412, and to allow teeth 490 engage teeth 440 on base 412. Mounting bracket 416 is secured on base 412 by the compression force created between rib engaging portion 450 against rib R and mounting plate 444 against outer rim 434 of base 412. Removal of retractor blade 418 from rib R occurs by sliding retractor blade 418 radially inward, thereby releasing compression sufficiently to allow mounting plate 444 to be released from outer rim 434.

Figure 38:
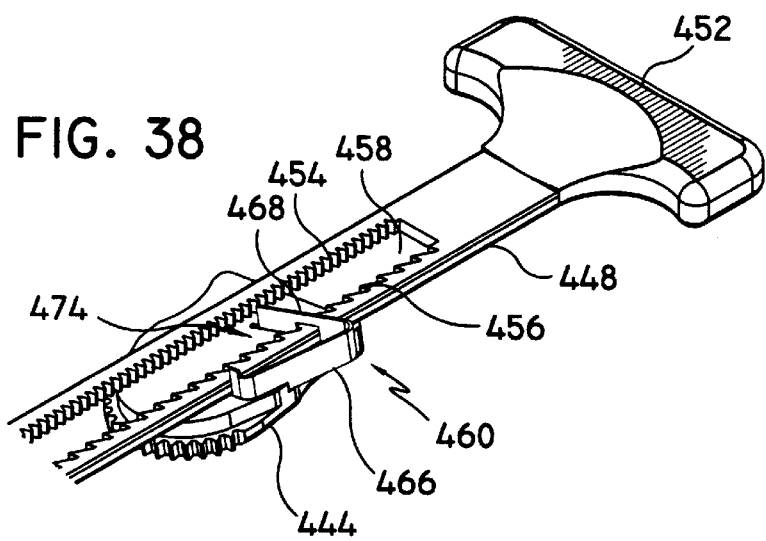
FIG. 38 is a perspective view, illustrating the pawl member and the retractor blade in engagement.
Figure 39:
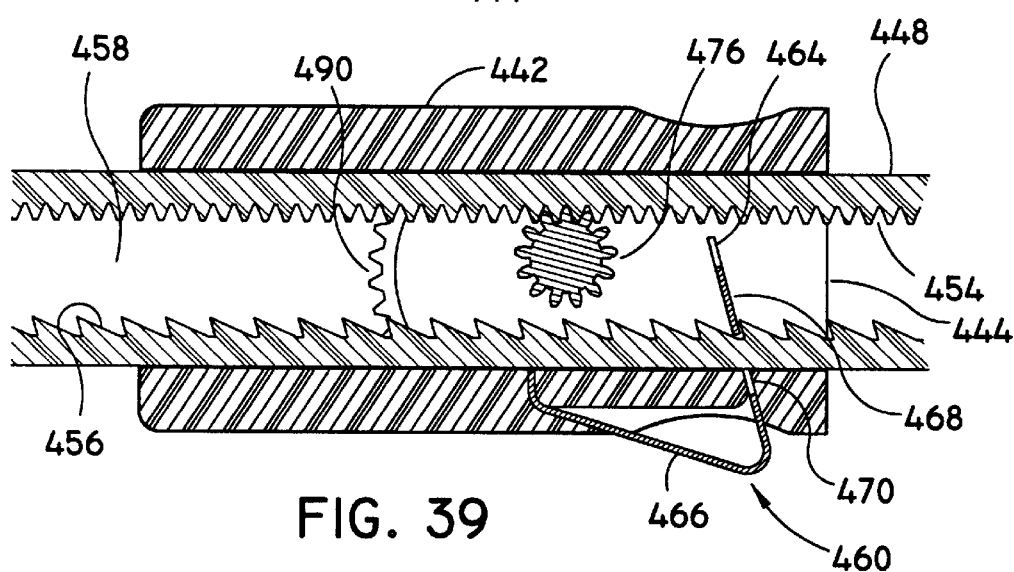
FIG. 39 is an enlarged cross-sectional view taken along line 39—39 of FIG. 37, illustrating the ratchet on the retractor blade in engagement with the pawl member.

One-way ratchet mechanism 474 enables retractor blade 418 to be incrementally moved in one direction, i.e. radially outwardly to retract a rib, while resisting movement in an opposite direction, i.e. radially inward. FIG. 38 illustrates pawl 460 normally biased such that first leg 456 is in engagement with ratchet teeth 456. As shown in FIG. 39, sloping portions 490 of teeth 456 permit retractor blade 418 to incrementally move in a radially outward motion while transverse slopes 492 of teeth 456 inhibit radially inward motion to hold retractor blade 418 and the rib in position. AS described above with respect to retractor 200, additional retraction force can be applied to the rib by rotation of retraction knob 420. Pinion gear 476 disposed on retraction knob 420 engages rack 454 on retraction blade 418 to provide additional leverage to the surgeon. After retracting the rib to create sufficient access for the surgeon, rotation knob 420 may be removed from aperture 478 in housing 442 (See, FIG. 35) and thereby provide greater visibility and access for the surgeon.

Figure 40:
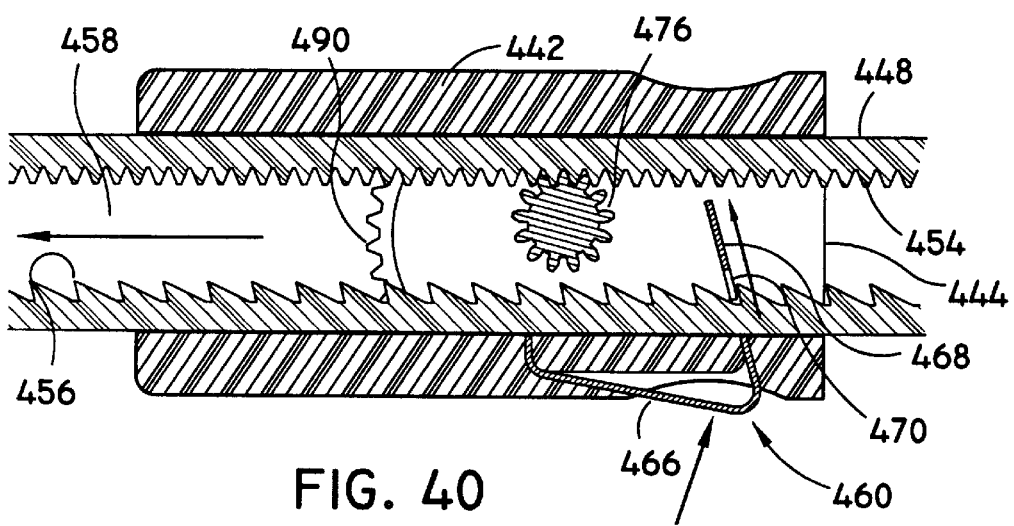
FIG. 40 is an enlarged cross-sectional view, illustrating a pawl member associated with the base moved out of engagement with the retractor blade.

Pawl 460 may be moved against its normal bias by depressing crown 466 towards mounting plate 444, which causes first leg 468 to disengage from ratchet teeth 456 as shown in FIG. 40. Cut-out portion 470 as aligned such that blade 418 may slide therethrough, such that unrestricted radial movement of retraction blade 418 is enabled.

Figure 41:
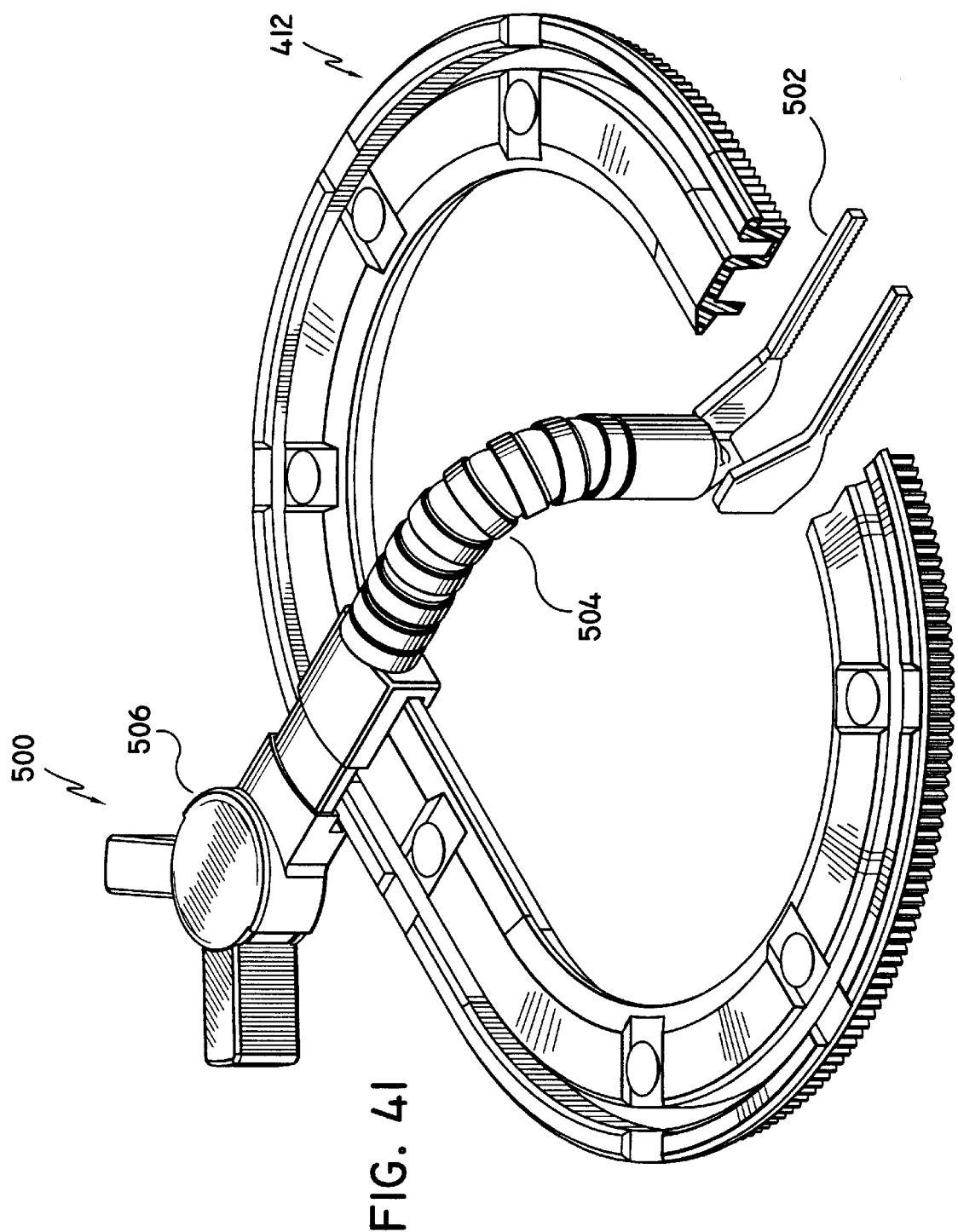
FIG. 41 is a perspective view of another embodiment of a hear stabilizer instrument mounted to the base of FIG. 34.

FIGS. 41–49 illustrate a heart stabilizer instrument 500 in accordance with another preferred embodiment of the subject disclosure. With reference to FIG. 41, heart stabilizer instrument 500 includes frame 502, articulating arm 504, and mounting assembly 506. Articulating arm 504 is configured to allow frame 502 to be positioned at the precise location and orientation with respect to the heart of the patient. Mounting assembly 506 secures articulating arm 504 and frame 502 in a fixed configuration, as will be described below.

Frame 502 is configured to contact the heart and applies pressure to the heart without touching the coronary artery. Frame 502 includes a pair of legs 508a and 508b, each having teeth 510 for atraumatically contacting the heart. Frame 502 is mounted to frame mount 512 by pin 514. The distal end of cable 516 is mounted to frame 502, and passes into frame mount 512 at opening 513.

Articulation arm 504 consists of a plurality of link members 518a, 518b, 518c, 518d, each of which has hemispherical convex distal portion 520, cylindrical body portion 522 including peripheral step 523, and concave proximal end 524. Bore 526 extends longitudinally through each link 518 from convex distal portion 520 to concave proximal end 524. Link members 518 are aligned such that convex distal portion 520 is received in concave proximal end 524 in a ball-and-socket type connection to permit a wide range of pivoting motion between adjoining link members 518. Link members 518 are concatenated by cable 516 passing through each bore 526, and the distalmost link member 518a is fitted adjacent frame mount 512. Articulation arm 504 can be used to mount a light cable to illuminate the surgical site, a suction and/or irrigation device, a blowing device to disperse blood or any other instrument to facilitate the surgery.

Figure 42B:
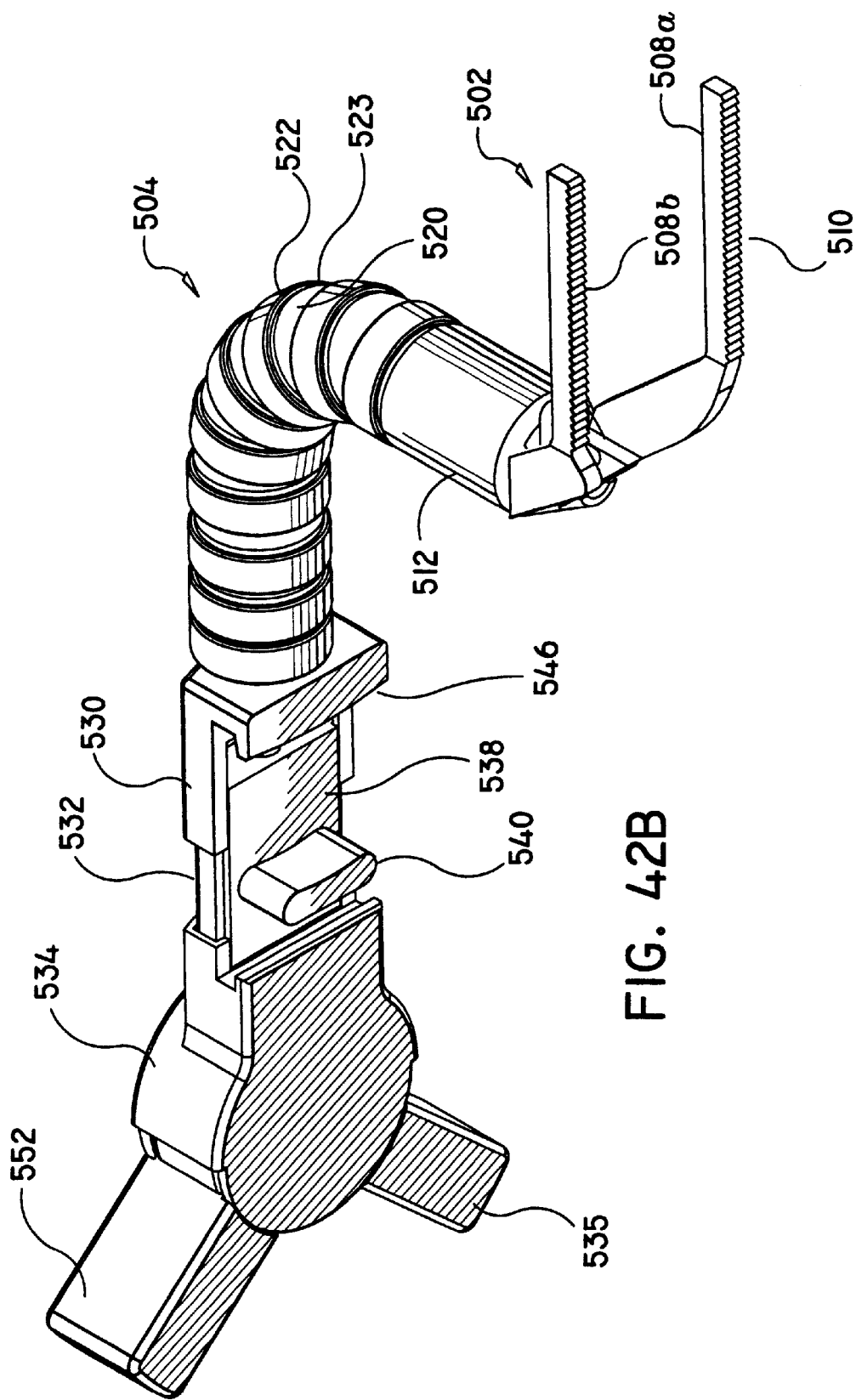
FIG. 42B is a perspective view from below of the heart stabilizer instrument of FIG. 41.

Mounting assembly 506 is mounted adjacent proximalmost link member 518d and includes mounting flange member 530, mounting base 532, toggle housing 534, and toggle 536. As shown in FIG. 42B, mounting base 532 has a flat bottom surface 538 to rest on top surface 432 of base 412 and a protrusion or peg 540 configured and dimensioned to be received in flange 436 of base 412. With continued reference to FIG. 42, mounting flange member 530 and toggle housing 534 are slidably mounted with respect to mounting base 532 by springs 542 and 544, respectively. Mounting flange member 530 has flange 546 for engaging inner rim 430 of base 412. Toggle housing 534 has flange 548 for engaging outer rim 434 of base 412.

Toggle 536 includes cylindrical mounting portion 550 and toggle arm 552. Cylindrical mounting portion 550 is configured to be received within cylindrical recess 554 defined within toggle housing 534 and to be pivotably movable therein. Cable 516 extends through link members 518 and through mounting flange member 530, spring 542, mounting base 532, spring 544, and into cylindrical recess 554 of toggle housing 534. The distal end portion of cable 516 is pinned to toggle 536 by pin 556. As illustrated in FIG. 42A, cylindrical mounting portion 550 defines a laterally offset pie-shaped or arc-section recess 558 to define an "overcenter" type locking mechanism, as will be described below.

Figure 43:
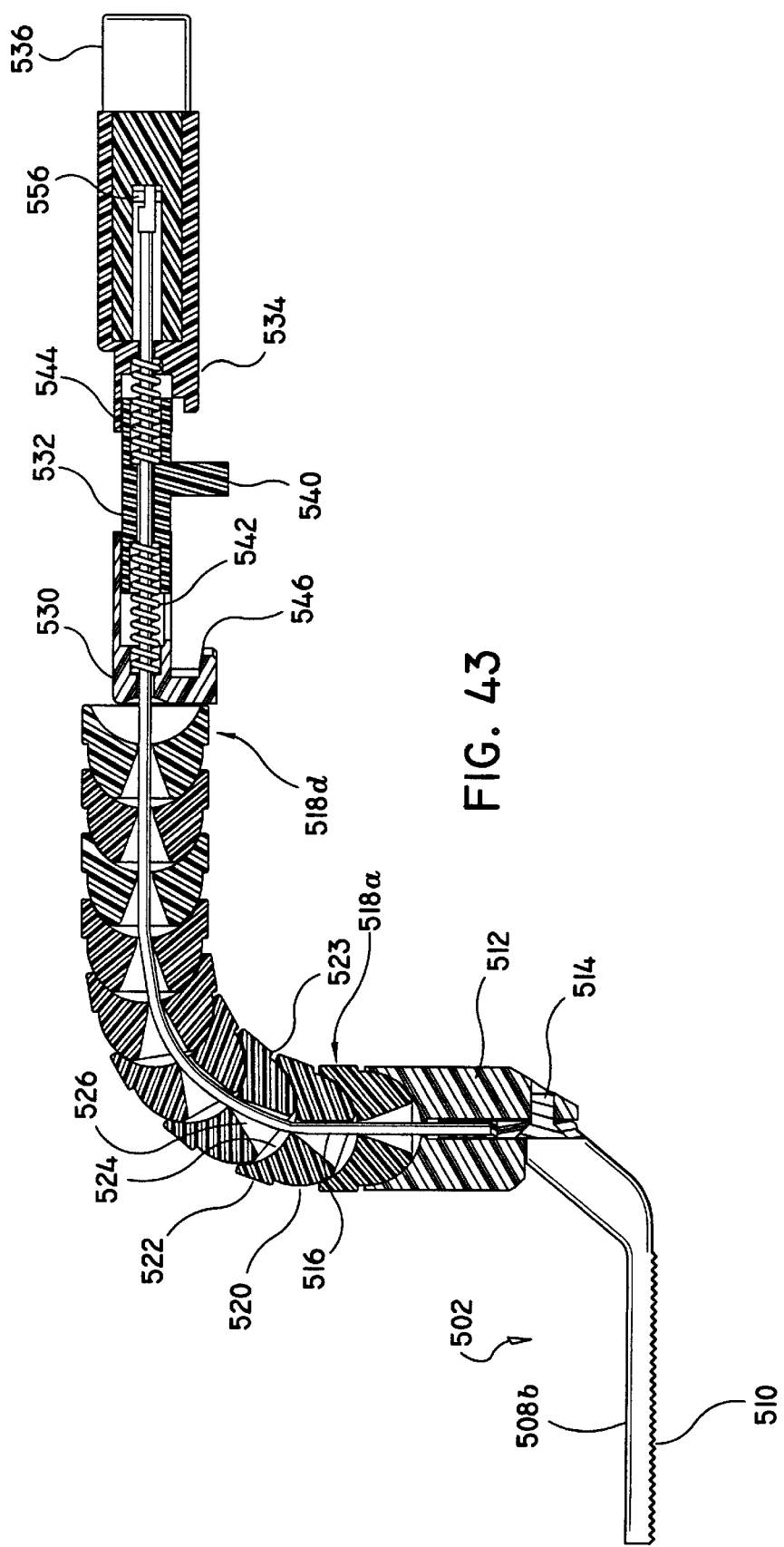
FIG. 43 is a side cross-sections view of the heart stabilizer instrument of FIG. 41.

As illustrated in FIG. 43, heart stabilizer instrument 500 is configured such that cable 516 extends through instrument 500 from frame 502 to toggle 536. Bore 526 in each link member 518 has a tapering diameter which is larger adjacent convex distal portion 520 and is narrower adjacent concave proximal portion 524. This configuration permits relative articulation of link members 518 while cable 516 extends therethrough.

FIGS. 44–46, illustrate heart stabilizer instrument 500 with cable 516 in a relaxed unstressed configuration. As illustrated in FIG. 44, instrument 500 is placed on base 412 such that peg 540 is disposed in groove 436, and mounting flange member 530 and toggle housing 534 are spaced apart sufficiently to allow flanges 546 and 548 to clear inner rim 430 and outer rim 434, respectively.

As illustrated in FIG. 45, toggle 536 is disposed in toggle housing 534 in an unlocked configuration, such that toggle arm 552 and fixed arm 535 are spaced apart. Eccentrically mounted pin 556 is disposed such that cable 516 is loose. FIG. 46 illustrates that cable 516 loosely disposed in tapered bores 526 of link member 518 permit articulation of adjoining link members 518.

Figure 49:
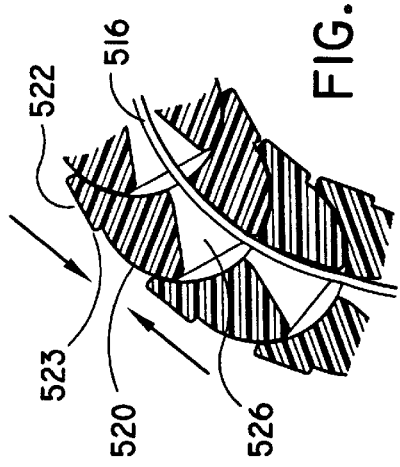
FIG. 49 is an enlarged cross-sectional view of a portion of the articulating arm, illustrating the cable in a tightened configuration corresponding to the locked configuration of FIGS. 47–48.
Figure 47:
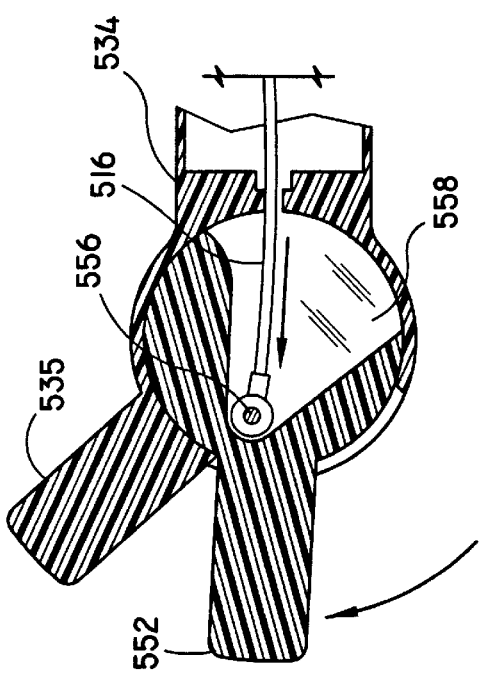
FIG. 47 is an enlarged cross-sectional view of the toggle mechanism in an locked configuration.
Figure 48:
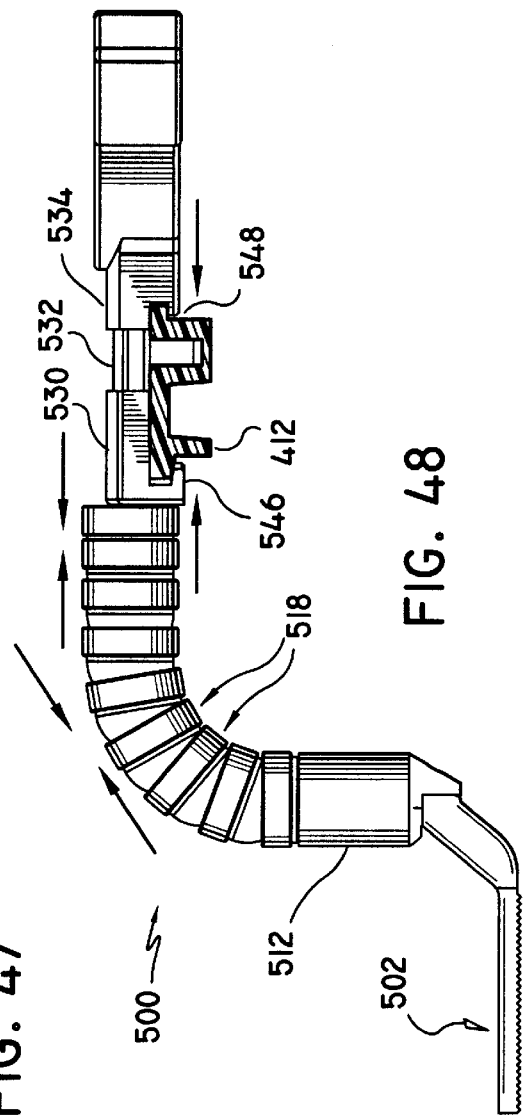
FIG. 48 is a reduced scale side view in partial cross-section of the heart stabilizer instrument in an locked configuration.

FIGS. 47–49 illustrate instrument 500 with cable 516 in a taut, stressed configuration. As depicted in FIG. 47, toggle 536 is pivoted with respect to toggle housing 534 such that toggle arm 552 is approximated with fixed arm 535. Simultaneously, the distal end of cable 516 connected to pin 556 moved into an "over-center" position, thereby stressing cable 516 and locking surgical instrument 500 in position. The surgeon is permitted to perform other procedures without maintaining pressure on the heart.

Another embodiment of the heart stabilizer instrument is illustrated in FIG. 50 and disclosed at reference number 600. Instrument 600 is constructed and operates substantially as described above with regard to instrument 500, with the differences described below. Heart stabilizer instrument 600 includes frame 502, articulating arm 606 and mounting assembly 506. Articulating arm 606 permits frame 502 to be placed at the appropriate height and angle with respect to the heart. Articulating arm 606 is composed of link members 608, and 610 having a series of intermeshing teething to positively engage adjoining link members together.

Figure 50A:
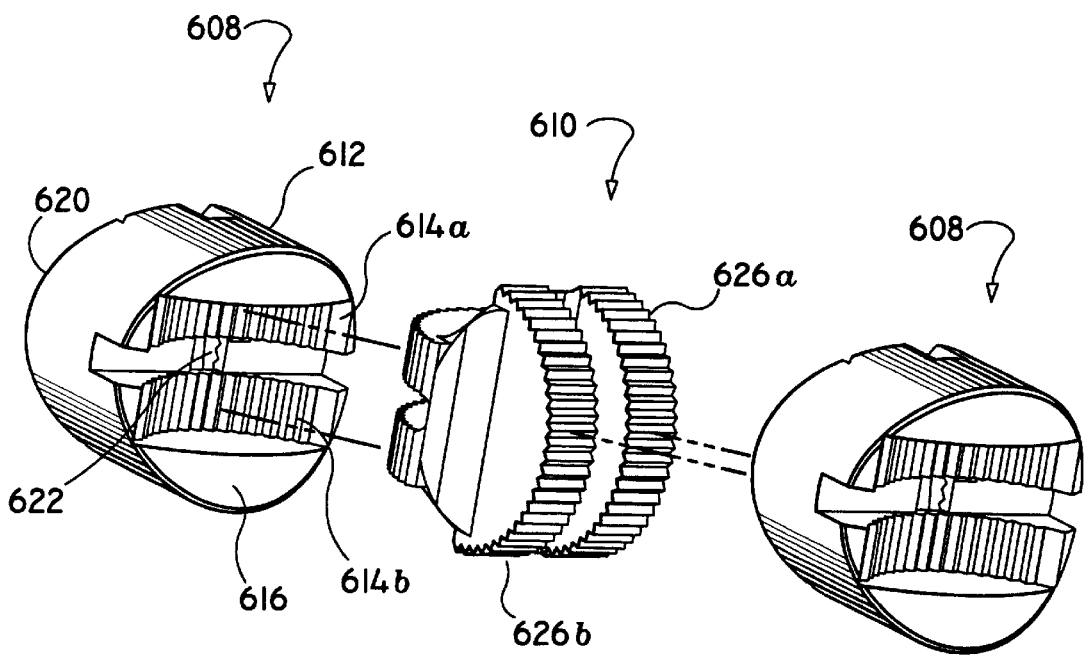
FIG. 50A is an enlarged perspective view of the link members of the heart stabilizer instrument of FIG. 50.
Figure 50B:
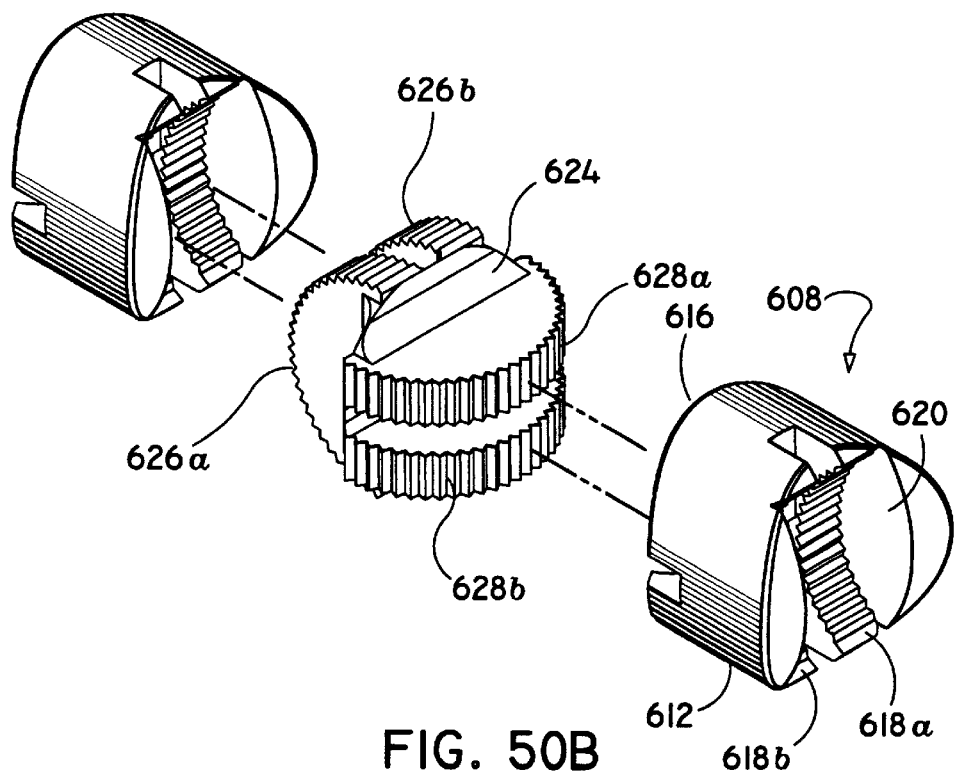
FIG. 50B is an enlarged perspective view of the link members of the heart stabilizer instrument of FIG. 50.

As illustrated in FIGS. 50A and 50B, link members 608 are positioned adjacent link member 610. Link member 608 has generally cylindrical body portion 612. A pair of rows of concave gearing 614a and 614b is disposed on one axial end 616 of link member 608. A second pair of rows of concave gearing 618a and 618b is disposed on the second axial end 620 of link member 608. Gearing 614a and 614b is disposed 90° out of alignment with gearing 616a and 616b. Longitudinal bore 622 extends through link member 608 from axial end 616 to axial end 620 between each pair of gearing.

Link member 610 has body portion 624, to which first pair of gearing 626a and 626b having a convex profile and second pair of convex gearing 628a and 628b are attached to opposite sides thereof. First pair of gearing 626a and 626b is disposed 90° out of alignment with second pair of gearing 628a and 628b. A longitudinal bore (not shown) extends through body portion 624 and between each pair of gearing 626a and 626b and gearing 628a and 628b.

Link member 610 is placed adjacent link member 608. Cable 516 extends through longitudinal bore 622 in link member 608 and longitudinal bore (not shown) in link member 610. When toggle 552 is moved to the "over center" position (See, FIG. 47), thereby tightening cable 516, link members 608 and 610 are approximated such that convex gearing 626a, 626b or 628a, 628b of link member 610 engages concave gearing 614a, 614b and 818a, 618b of link member 608.

Figure 51:
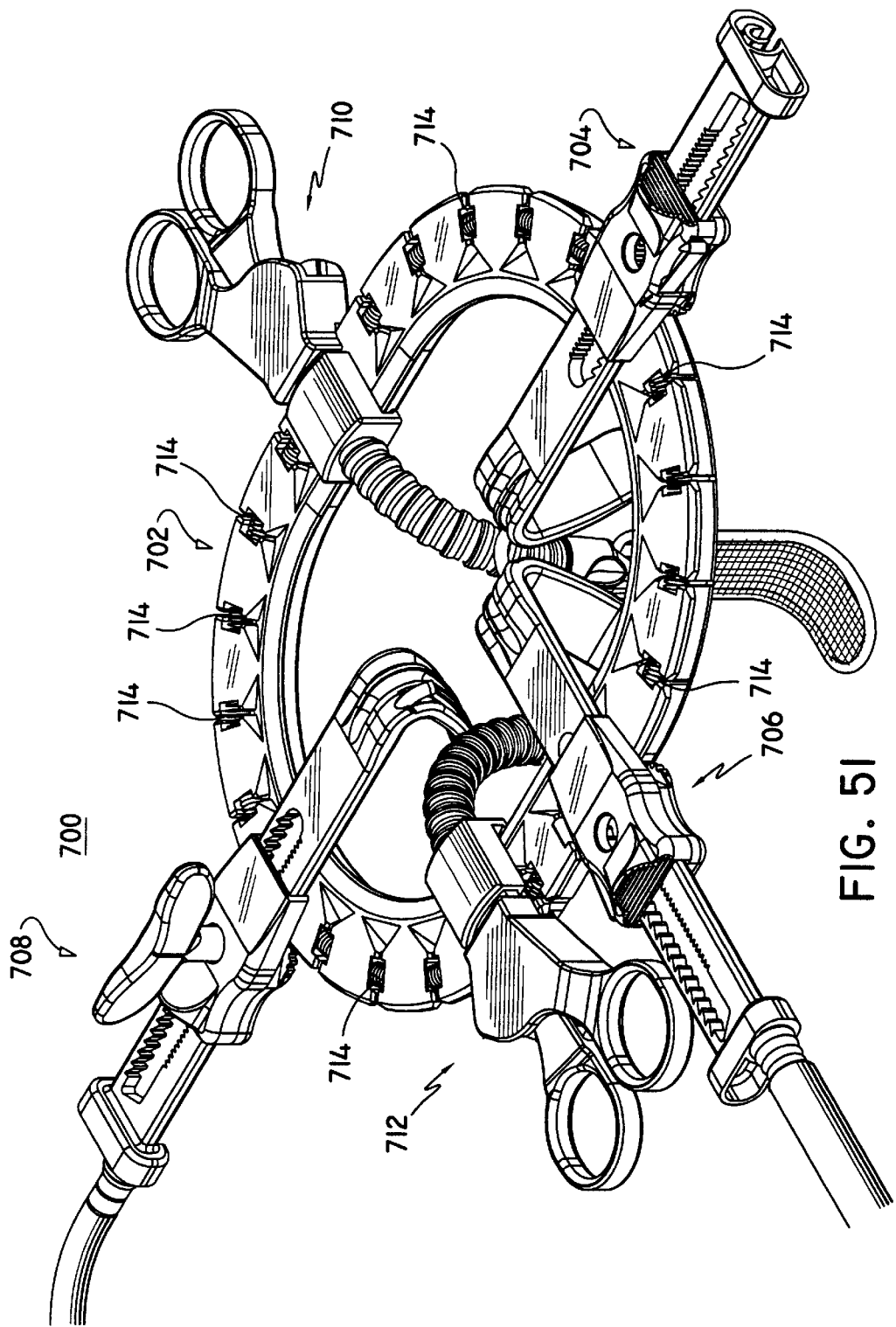
FIG. 51 is a perspective view of a surgical retraction system in accordance with another embodiment of the subject disclosure incorporating a variety of retractors, a heart manipulator and a heart stabilizer, all positioned on a base.

FIG. 51 illustrates another preferred embodiment of the surgical retractor in accordance with the subject disclosure. This surgical retractor, designated generally at 700, includes a base 702 and any one or more of the instruments shown including: retractor blade assembly 704; retractor blade assembly with suction/irrigation structure 706; retractor blade assembly with light 708; heart manipulator 710; and heart stabilizer instrument 712. These instruments are discussed in greater detail hereinbelow.

Figures 52, 53:
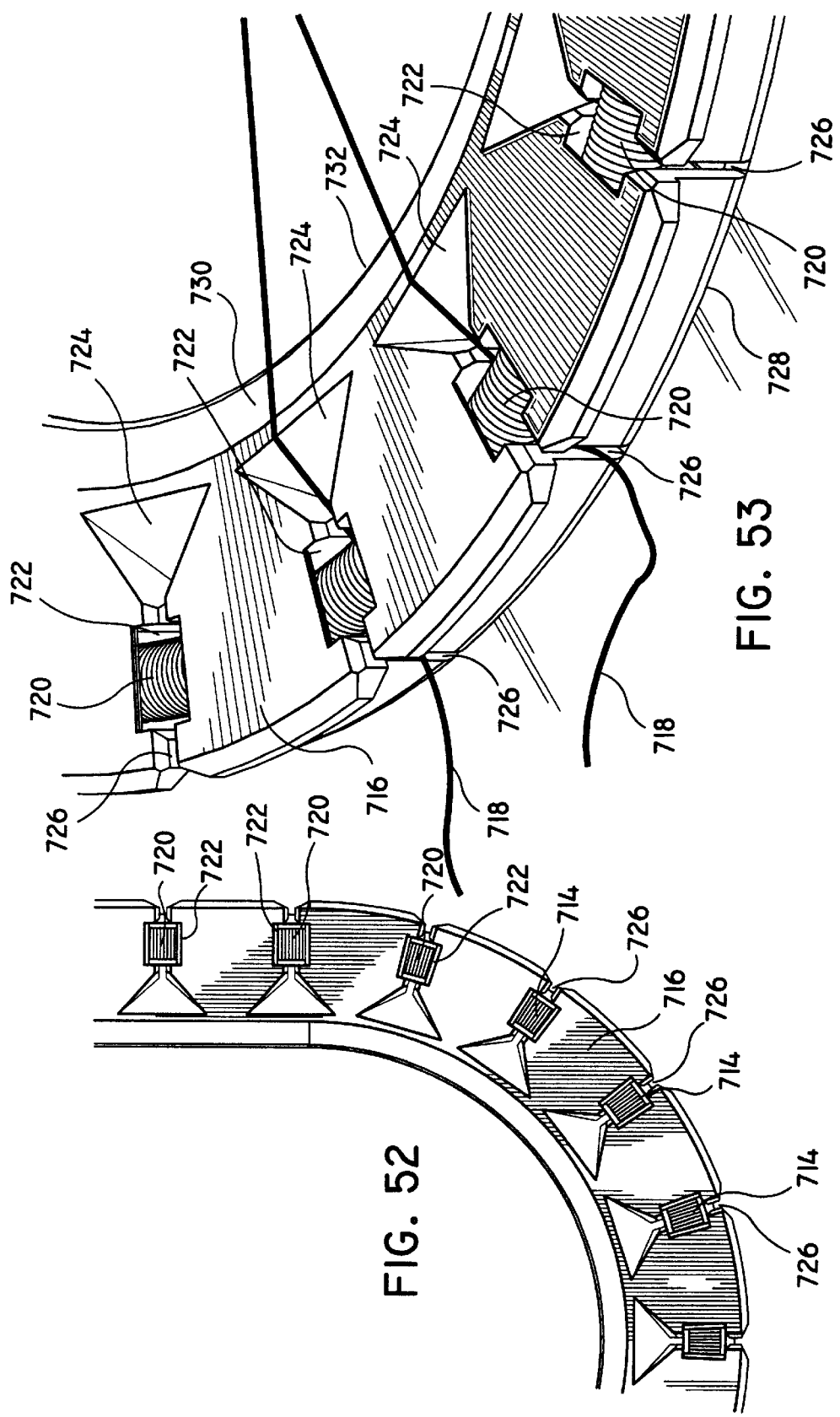
FIG. 52 is a top view of the base of FIG. 51 illustrating suture mounts positioned thereabout.
FIG. 53 is an enlarged perspective view of the suture mounts of FIG. 52.

Base 702 is configured in accordance with the other bases discussed above and provides a low profile mount for instrumentation used in the surgical procedure being performed. A plurality of suture mounts 714 are defined in an upper peripheral portion 716 of base 702 and serve as attachment and anchor points for suture ends 718 from the surgical field. Referring to FIGS. 52 and 53, suture mounts 714 include a tightly wound coil spring 720 positioned in a cavity 722 with the coils oriented substantially transverse to the radians of the base 702. A triangular ramp 724 is formed on an inner radial surface of suture mount 714. A slot 726 is formed on an outer radial surface of suture mount 714 beyond coil spring 720 and in axial alignment with ramp 724. This ramp/slot configuration facilitates easy access to position suture end 718 in coil spring 720.

The balance of base 702 is configured in substantially the same manner as previously described bases and includes teeth 728, beveled inner peripheral surface 730 and inner lip 732.

Figure 54:
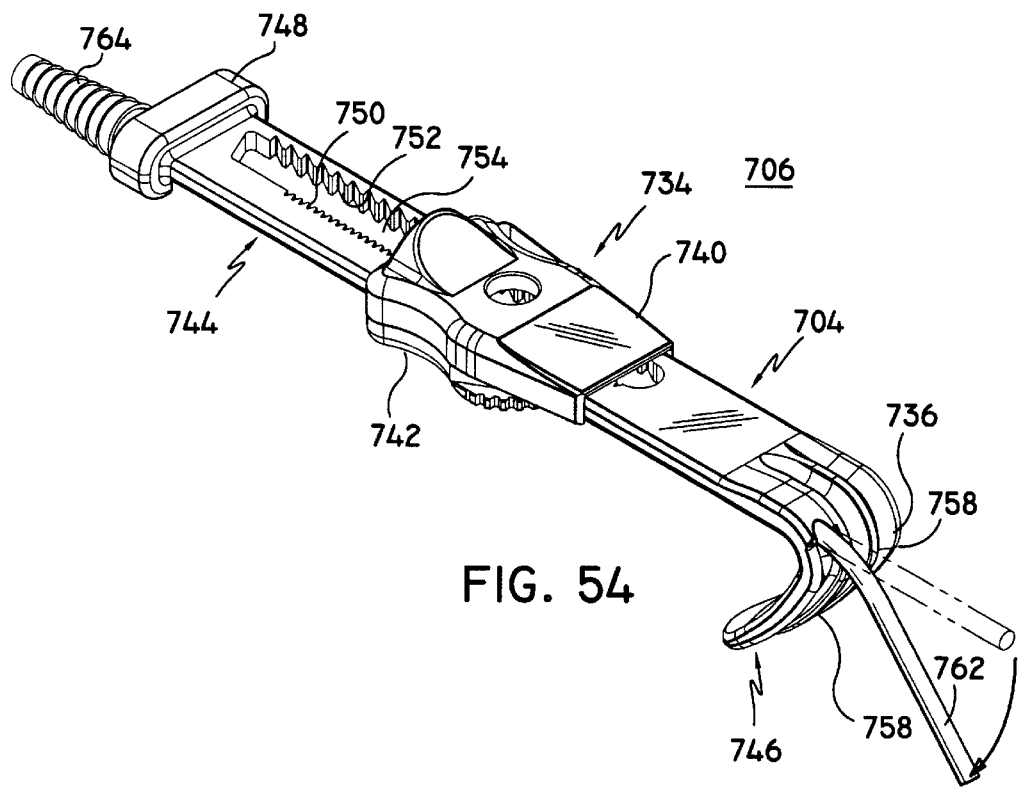
FIG. 54 is a perspective view of a surgical retractor in accordance with the subject disclosure incorporating an integral blowing structure.
Figure 55:
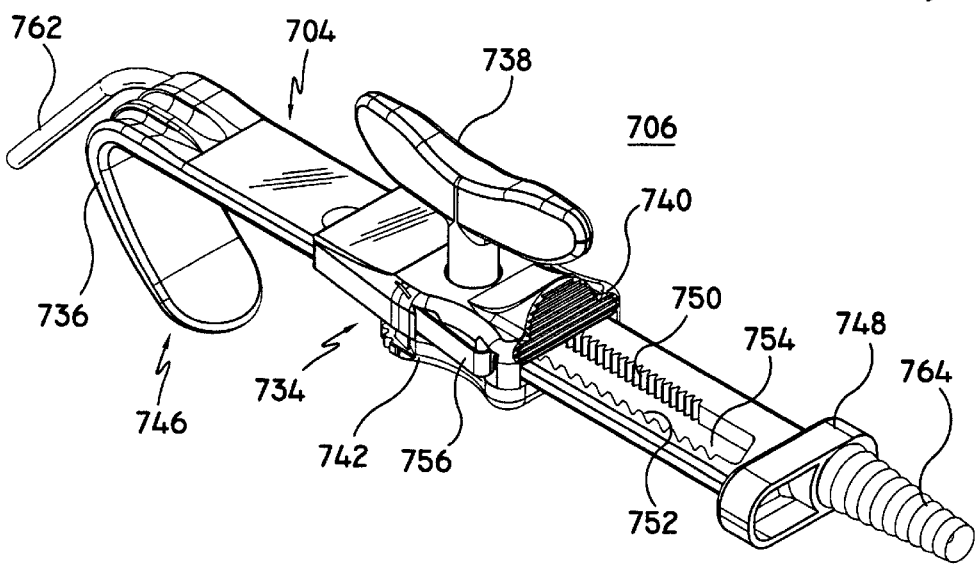
FIG. 55 is a reverse perspective view of the surgical retractor of FIG. 54.
Figure 56:
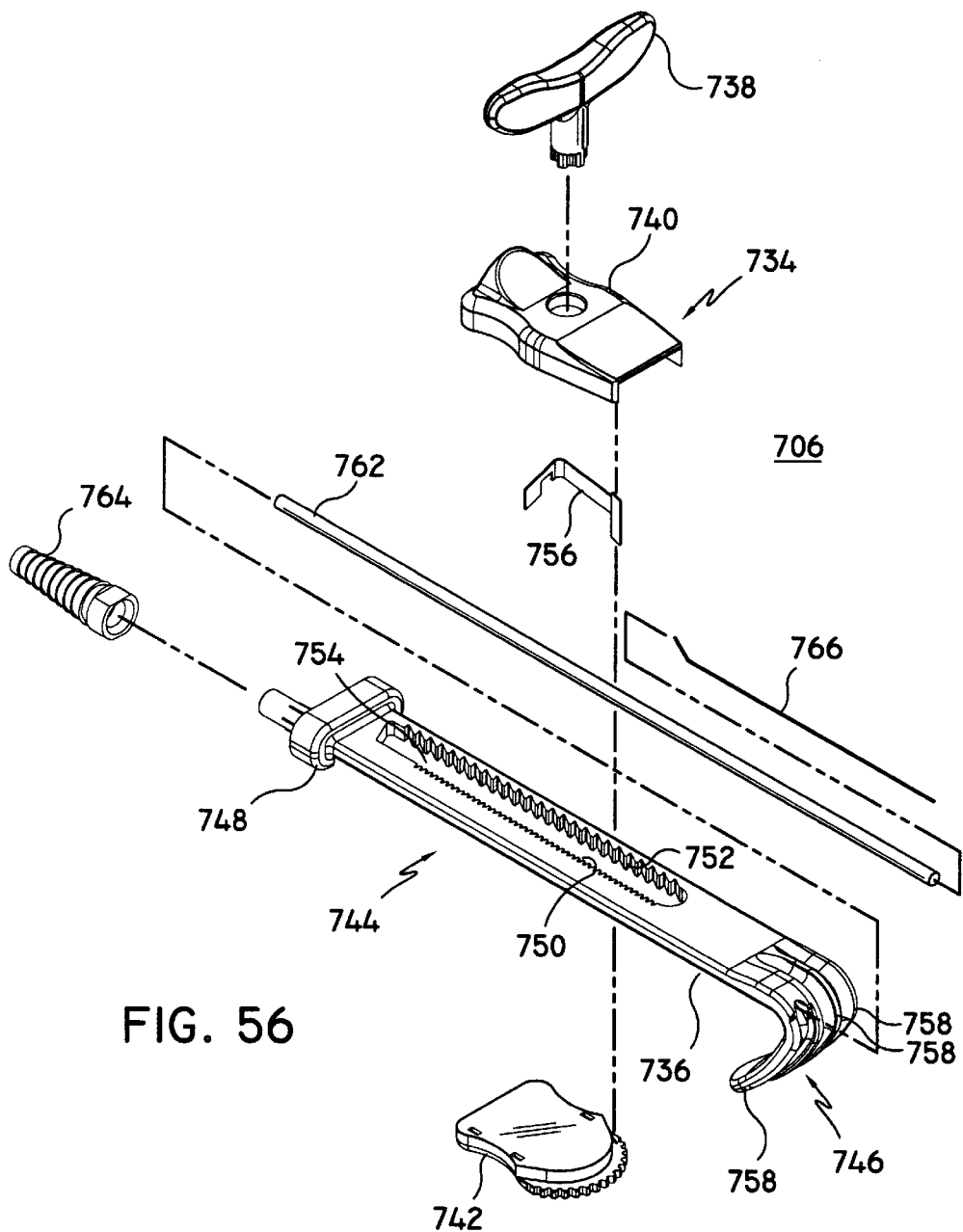
FIG. 56 is an enlarged perspective view with parts separated of the surgical retractor of FIG. 54.

Surgical retractor blade assembly with blowing structure 706 is shown in FIGS. 54–56. Structure 706 can also be used for suction or for irrigation to remove fluids from the surgical sit. The retractor blade assembly 704 is similar to the retractor blade assembly 414 discussed in detail above. Retractor blade assembly 704 includes mounting bracket 734, retractor blade 736 and removable retraction knob 738.

As illustrated in FIG. 56, mounting bracket 734 includes housing 740 and mounting plate 742 which together form a channel through which retractor blade 736 is reciprocally slidable.

Retractor blade 736 includes body portion 744 and rib engaging portion 746. Body portion 744 defines a flanged gripping handle 748 configured to be grasped by the surgeon in order to slide retractor blade 736 relative to mounting bracket 734. Body portion 744 further defines longitudinally oriented rack gearing 750 and a series of sloping teeth 752. Rack gearing 750 and teeth 752 are disposed along elongated cavity 754 defined in body portion 744.

Teeth 752 are releasably engaged by pawl 756 mounted in housing 740. Operation of this pawl 756 is substantially the same as pawl 460 described above in connection with retractor blade assembly 414.

Rib engaging portion 746 extends distally from body portion 744 and includes an angularly depending portion including one or more strengthening ribs 758 to provide additional strength.

Blowing structure 760 is integrally formed into the retractor blade assembly shown in FIGS. 54–56. This structure includes a tube 762 which extends the length of the retractor blade assembly and exits the ring engaging portion 764 to access the surgical site. A tube connector 764 is positioned at a proximal end of tube 762 and connects to an appropriate source such as a vacuum or pressure source (not shown) depending on whether structure 760 is used for blowing, irrigation or suction. Forming wire 766 is positioned adjacent tube 762 and is deformable to configure tube 762 in a desired angular orientation. Alternatively, tube 762 may be remotely oriented or rotated from body portion 744 using known structure.

Figure 57:
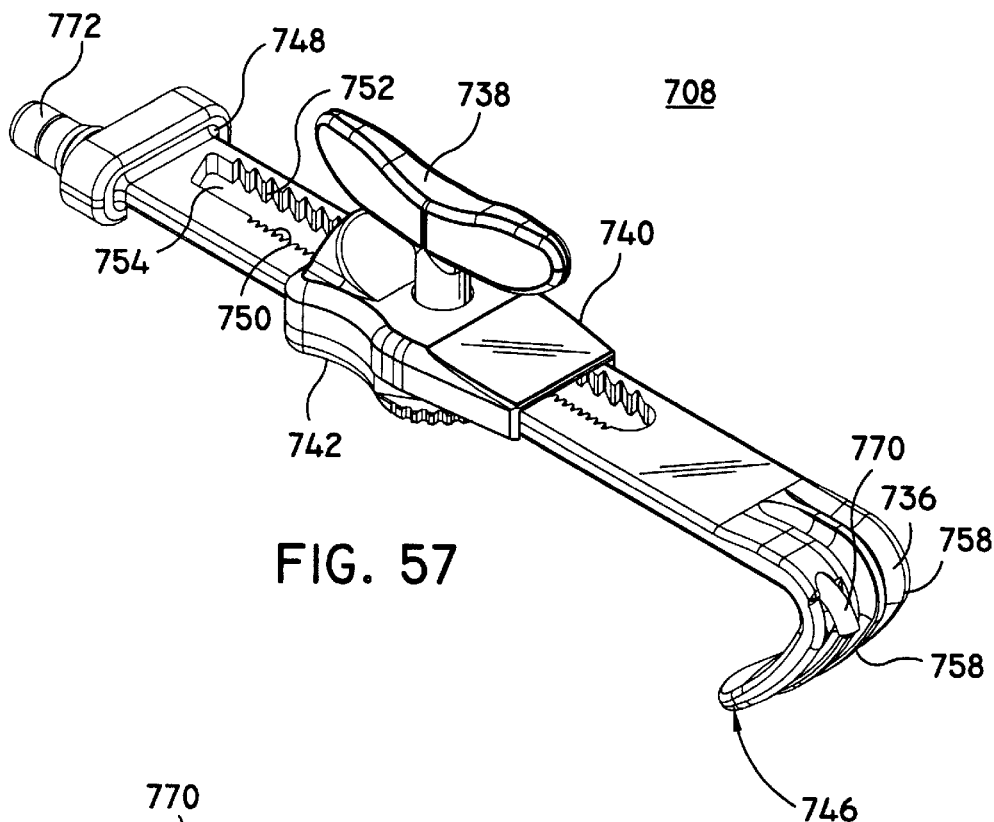
FIG. 57 is a perspective view of a surgical retractor in accordance with the subject disclosure incorporating a light.
Figure 58:
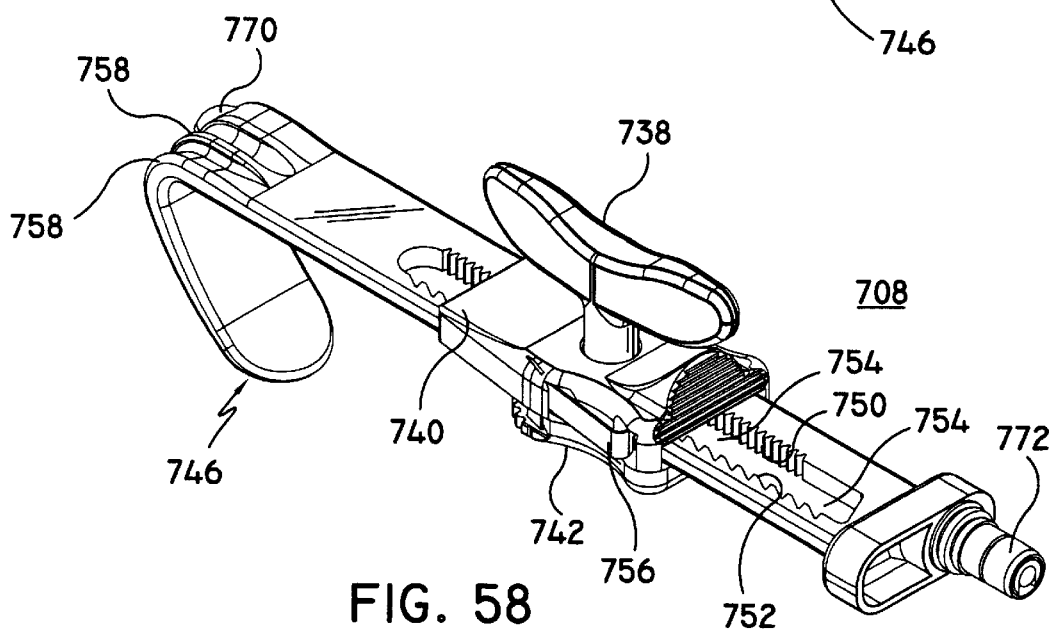
FIG. 58 is a reverse perspective view of the surgical retractor of FIG. 57.

FIGS. 57 and 58 illustrate a retractor blade assembly with an integral light shown generally at 708. The basic configuration and operation of this assembly is identical to that described above with the difference that a light 768 has been substituted for suction/irrigation structure. A wide variety of lights can be accommodated. In the illustrated embodiment, a fiber optic bundle is disposed within a longitudinally extending sheath 770. A fiber optic couple 772 is positioned adjacent the proximal end of the assembly and can be connected to an appropriate light source (not shown). It is also envisioned that a wide variety of divergent and focusing lenses may be used to tailor the light as required by the surgeon.

Figure 58A:
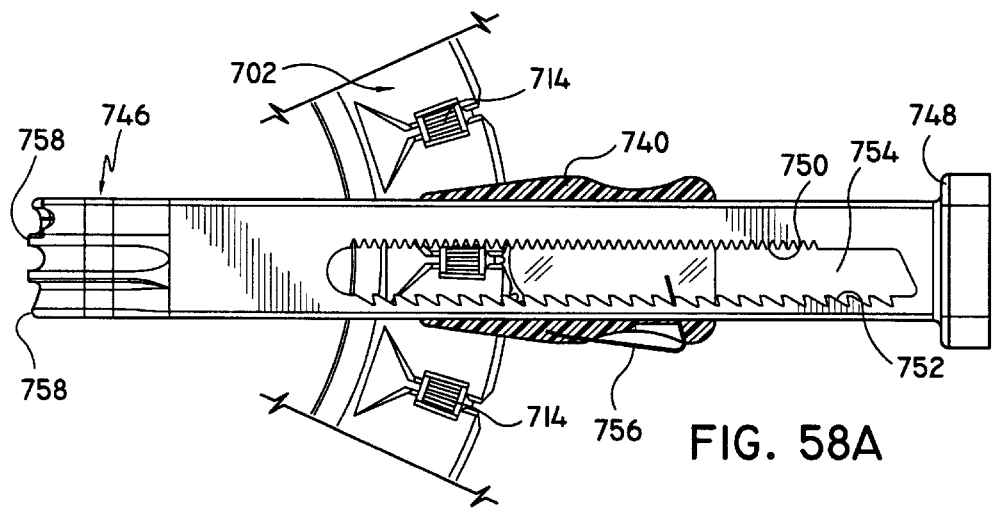
FIG. 58A is a top plan view in partial cross-section of a surgical retractor mounted to the bases of FIG. 52.
Figure 58B:
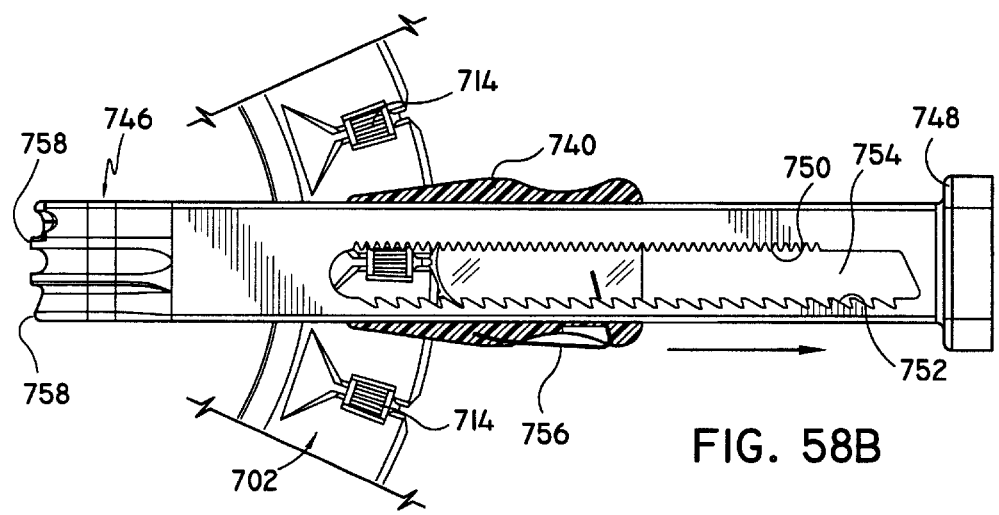
FIG. 58B is a top plan view in partial cross-section of the surgical retractor in FIG. 58A pulled proximally relative to the base.
Figure 58C:
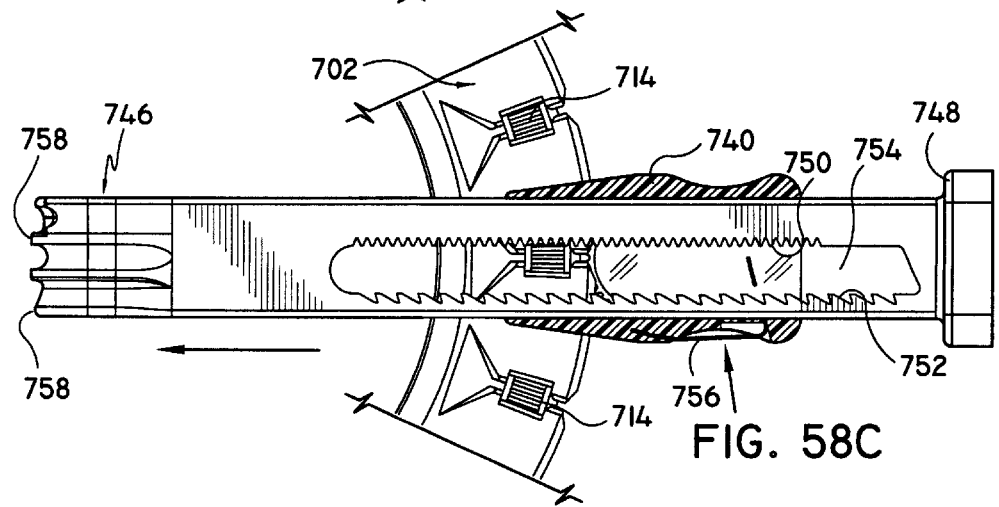
FIG. 58C is a top plan view in partial cross-section of the surgical retractor in FIG. 58A released from engagement with the rack.

The one-way ratchet mechanism used in these embodiments of the retractor blade assembly is shown in FIGS. 58A–C. This ratchet mechanism operates in the same manner as the ratchet mechanism discussed above with respect to FIGS. 39–40. Note that as shown in FIG. 58B, the retractor blade 736 can be pulled in the direction of the arrow to retract the bone and tissue. However, to move the retractor blade 736 in the opposite direction, i.e. the direction of the arrow of FIG. 58C, pawl 756 must be pressed in.

FIGS. 59–63 illustrate another embodiment of a heart stabilizer instrument 800 in accordance with the subject disclosure. Heart stabilizer instrument 800 is substantially the same as heart stabilizer instrument 500 discussed in detail above. The instrument includes frame 802, articulating arm 804 and mounting assembly 806.

Frame 802 is configured in the same manner as frame 502 and includes a pair of legs 808a and 808b, each having teeth 810 for atraumatically contacting the surface of the heart.

Frame 802 is connected to articulating arm 804 by connector 812. A positioning flange 814 is formed on connector 812 and facilitates positioning of frame 802 on the heart surface either by manually grasping the flange 814 or by affixing a grasping instrument (not shown) to the flange 814 and positioning the frame in a desired location.

Mounting assembly 806 is mounted adjacent the articulating arm 804 and includes mounting flange member 830, mounting base 832, toggle housing 834, and toggle 836. As shown in FIGS. 61–62, mounting base 832 has a flat bottom surface 838 to rest on the top of base 702. Mounting flange member 830 and toggle housing 834 are slidably mounted with respect to mounting base 832. Mounting flange member 830 has flange 846 for engaging inner rim of base 702. Toggle housing 834 has flange 848 for engaging outer rim of base 702.

Toggle 836 includes cylindrical mounting pins 850 and finger loop 852. Cylindrical mounting pins 850 are configured to be received within recess 854 defined within toggle housing 834 and to be pivotally movable therein. Cable 816 extends through articulating arm 804. The distal end portion of cable 816 is pinned to toggle 836 by clip 856. Biasing spring 858 is positioned in toggle housing 834 and serves to normally bias mounting flange member 830 distally relative to toggle housing 834.

Handle spring member 860 is integrally formed on toggle 836 and is configured to operatively interact with protrusion 862 formed in cavity 854 of toggle housing 834, as toggle 836 is moved into and out of approximation with toggle housing 834.

FIGS. 64–66, illustrate heart stabilizer instrument 800 with cable 816 in an unlocked, unstressed configuration. As illustrated in FIG. 64, instrument 800 is placed on base 702 with mounting flange member 830 and toggle housing 834 spaced apart sufficiently to allow flanges 846 and 848 to clear inner rim 830 and outer rim 833, respectively.

Toggle 836 is disposed in toggle housing 834 in an unlocked configuration, such that finger loop 852 and finger loop 853 are spaced apart. Cable 816 is loose to permit manipulation of articulating arm 804.

FIG. 65 illustrates the relative position of handle spring 860 relative to protrusion 862 within toggle housing 834.

FIGS. 66–67 illustrate instrument 800 with cable 816 in a first taut, locked, unstressed configuration. As depicted in FIG. 66, toggle 836 is pivoted with respect to toggle housing 834 such that finger loop 852 is moved toward finger loop 853. The distal end of cable 816 is stressed to approximate mounting flange member 832 and mounting base 832 locking surgical instrument 500 in position on base 702. FIG. 67 shows the progressing of toggle 836 relative to toggle housing 834 into the locked, unstressed configuration. In this position, articulating arm 804 can still be manipulated.

The final, locked and stressed configuration is shown in FIGS. 68–69. In this configuration, finger loops 852 and 853 have moved into close approximation simultaneously, further stressing cable 816 to maintain a preset configuration desired by the surgeon, e.g. to lock articulating arm 804 in place. Once locked into this locked-stressed configuration, the surgeon is permitted to perform other procedures without having to manually apply pressure on the heart via the heart stabilizer instrument.

Figure 70:
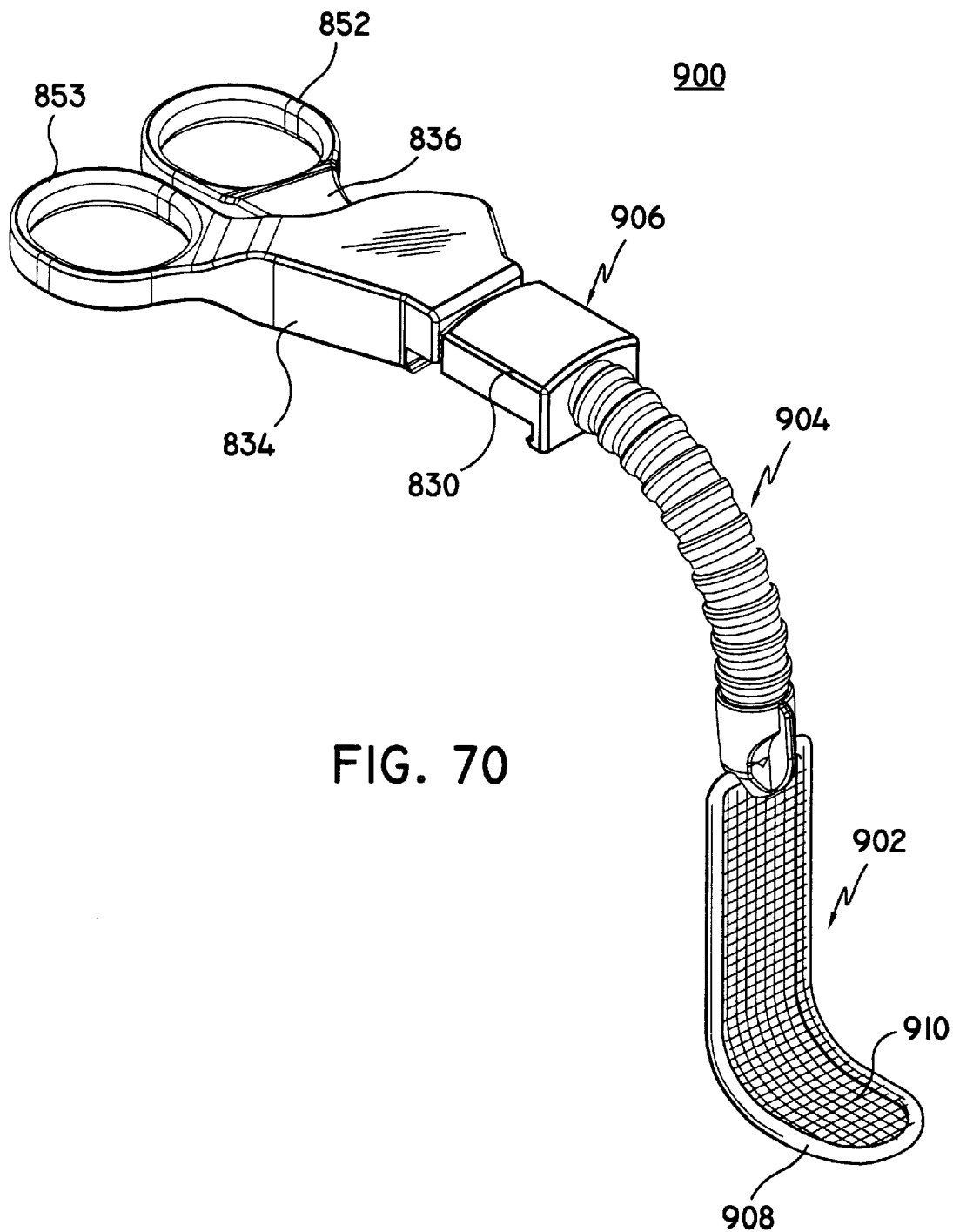
FIG. 70 is a perspective view of another embodiment of a heart manipulator.

Another preferred embodiment of the heart manipulator 900 in accordance with the subject disclosure is shown in FIG. 70. The heart manipulator includes a manipulator portion 902, an articulating arm 904 and a mounting assembly 906. The structure and operation of mounting assembly 906 and articulating arm 904 are substantially the same as the heart stabilizer 800 discussed above.

The manipulator portion 902 includes a frame 908 supporting mesh 910 and is preferably provided with a curved section adjacent a distal end thereof to assist in manipulation of the heart.

Figure 71B:
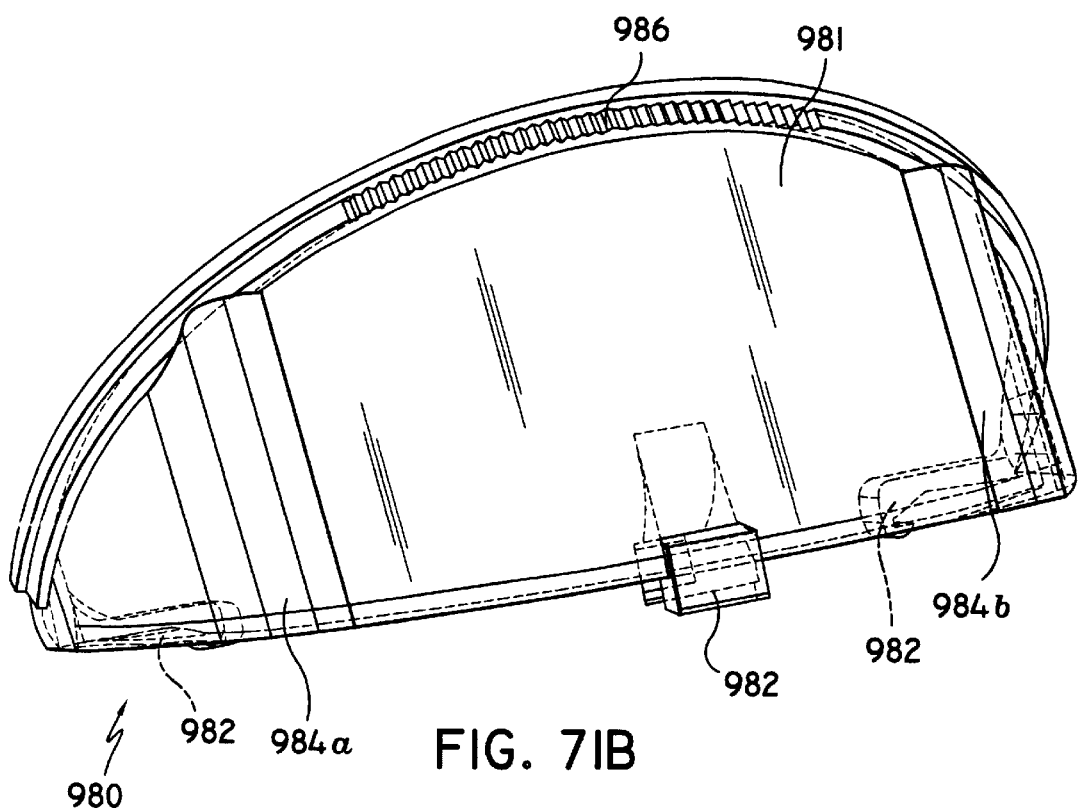
FIGS. 71A and 71B are front and back perspective views of the rib elevator.
Figure 71A:
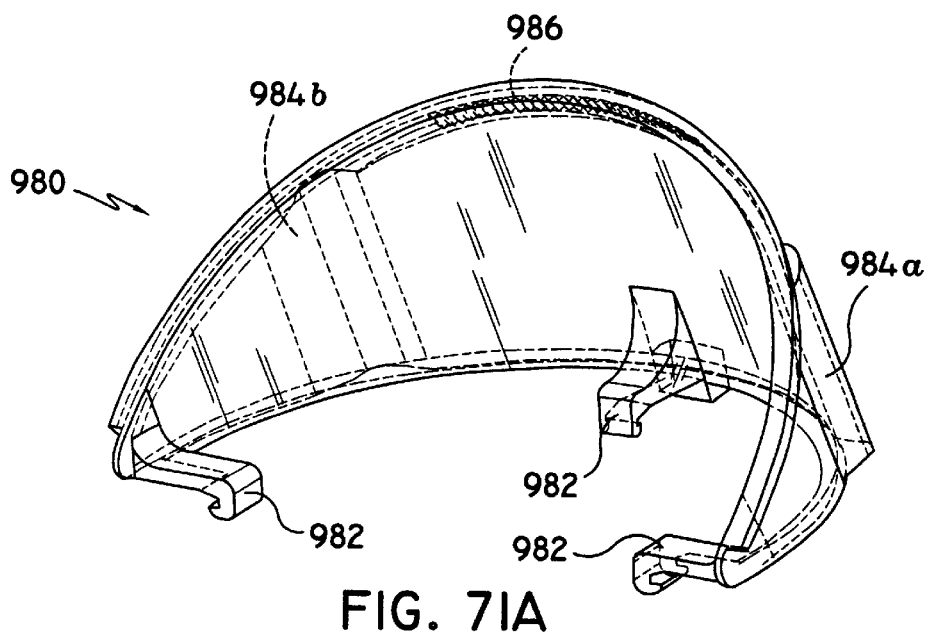

FIGS. 71A and 71B illustrate a rib elevator 980 which can be mounted to the aforedescribed bases to enable the patient's rib to be lifted. Rib elevator 980 includes a set of tabs 982 which engage inner lip 732 for attachment to the base. Reinforcement ribs 984a, 984b formed on the rear surface 981, increase the rigidity of rib elevator 980 and also provide a gripping surface fur the user to flex the rib elevator 980 to facilitate attachment and removal from the base. Teeth 986 function in the same manner as the teeth 728 of base 702, i.e. for mounting one or more of retractor assemblies 704, 706, 708. As can be appreciated, when rib elevator 980 is mounted to base 702, the mounted retractor assembly will be angled towards the rib so that a retraction force will be applied to the rib partially in an upward direction. This is advantageous, for example, for access and severing of the IMA. The rib elevator 980 can subsequently be removed and a retractor assembly mounted directly to the base 702 in the manner described above.

Figure 72:
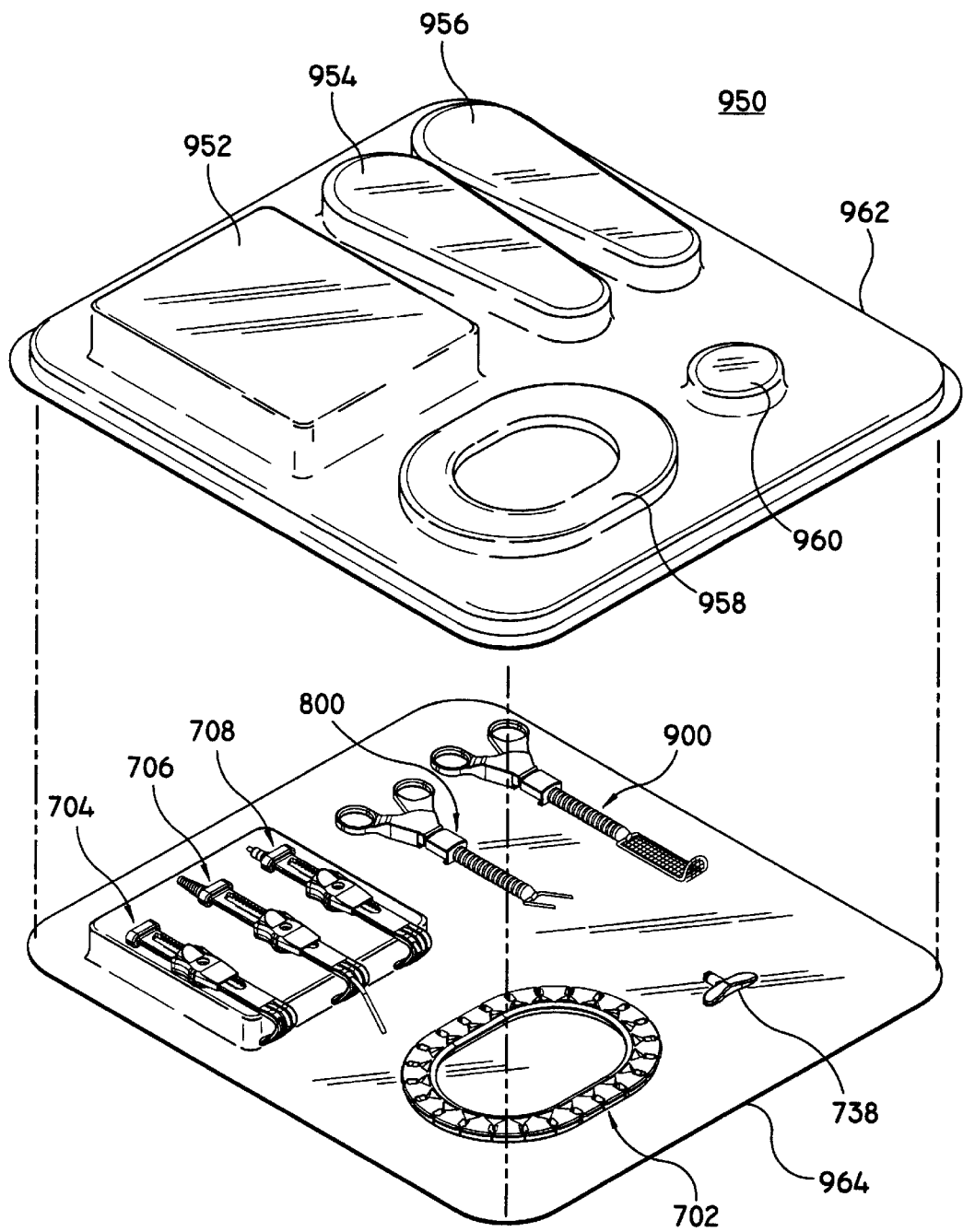
FIG. 72 is a perspective view of a kit assembly having a base, three retractors, a retractor knob, a heart manipulator and a heart stabilizer instrument.
Figure 73:
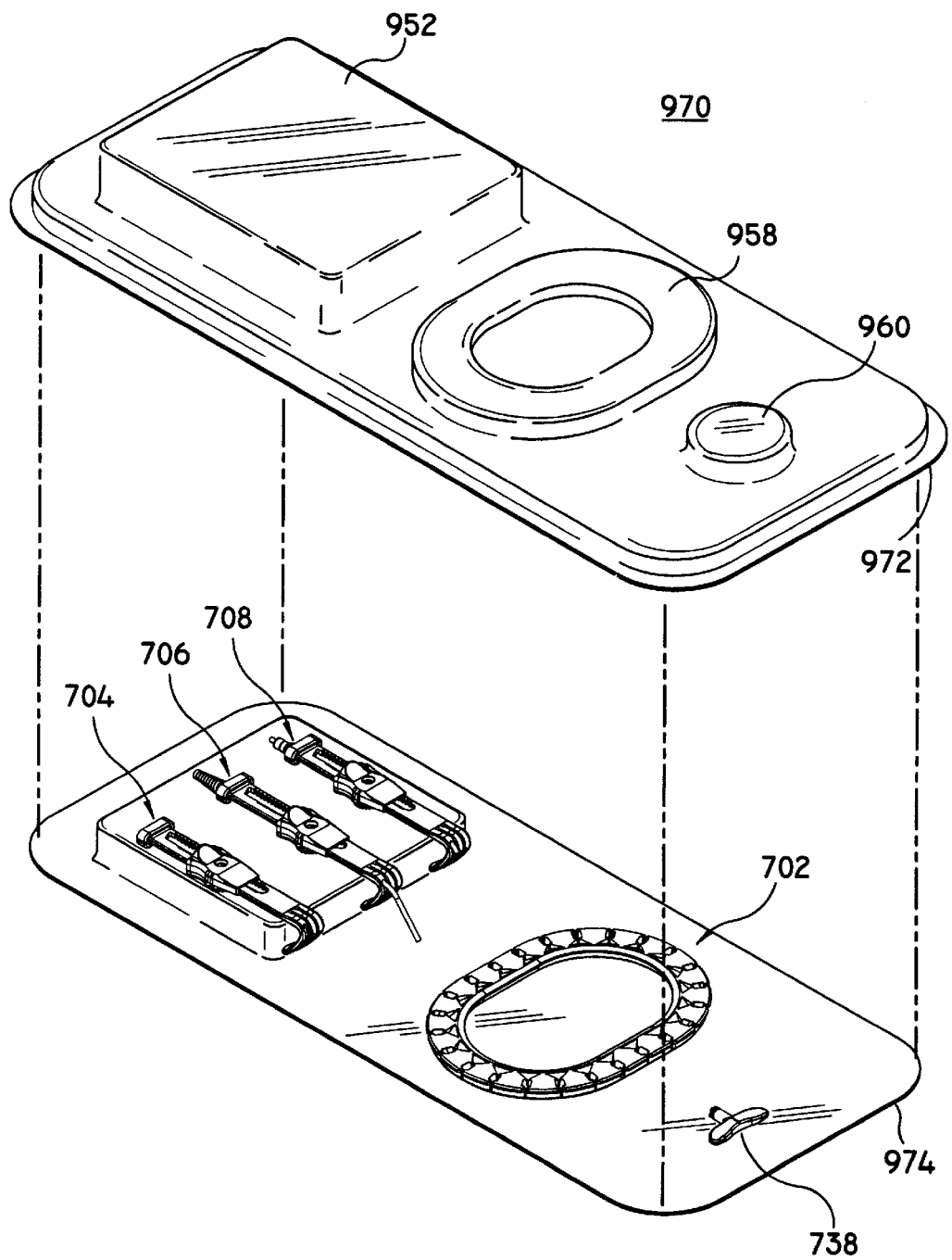
FIG. 73 is a perspective view of a kit assembly having a base, a retraction knob and three retractors.

FIGS. 71 and 72 illustrate two preferred kit configurations in accordance with the subject disclosure. Kit 950 (FIG. 71) is formed to accommodate a basic blade retractor assembly 704, a blade retractor assembly with suction irrigation 706, a blade retractor assembly with light 708, a base 702, a retraction knob 738, a heart stabilizer instrument 800 and/or a heart manipulator 900 therein. Cavities 952, 954, 956, 958 and 960 are formed in cover 962 to accommodate these elements. Cover 962 may be fixed to bottom 964 by adhesive, ultrasonic welding, heating, etc.

Kit 970 is substantially similar to kit 950 except that the heart stabilizer instrument 800 and the heart manipulator 900 are excluded. Cover 972 includes cavities 952, 958 and 960 to accommodate retractors 704, 706, 708, base 702 and retraction knob 738. Cover 972 and bottom 974 may be joined in the same manner as disclosed for kit 950 above.

Rib elevator 980 can optionally be included in the kits.

It will be understood that various modifications may be made to the embodiments shown herein. Therefore, the above description should not be construed as limiting, but merely as exemplifications of preferred embodiments. Those skilled in the art will envision other modifications within the scope and spirit of the claims appended hereto.

What is claimed is:

1. A surgical retractor base comprising:

a frame structure defining an opening for effecting a surgical procedure therethrough; and at least one suture mount disposed adjacent a peripheral portion of the frame structure, the suture mount including at least one cavity define therein housing a coil spring configured to retain a suture end portion therein.

2. A surgical retractor base as in claim 1, wherein the at least one cavity defined in the frame structure is configured to house the coil spring in an orientation substantially transverse to a radian of the frame structure.

3. A surgical retractor base as in claim 2, further comprising a ramp defined in the frame structure adjacent the cavity.

\* \* \* \* \*